US006306598B1

(12) United States Patent
Charych et al.

(10) Patent No.: US 6,306,598 B1
(45) Date of Patent: Oct. 23, 2001

(54) NUCLEIC ACID-COUPLED COLORIMETRIC ANALYTE DETECTORS

(75) Inventors: Deborah H. Charych, Albany, CA (US); Ulrich Jonas, Mainz (DE)

(73) Assignee: Regents of the University of California, Oakland, CA (US)

(*) Notice: Subject to any disclaimer, the term of this patent is extended or adjusted under 35 U.S.C. 154(b) by 0 days.

(21) Appl. No.: 09/337,973

(22) Filed: Jun. 21, 1999

Related U.S. Application Data

(60) Continuation-in-part of application No. 09/461,509, filed on Dec. 14, 1999, which is a division of application No. 08/592,724, filed on Jan. 26, 1996, now Pat. No. 6,001,556, which is a continuation-in-part of application No. 08/159,927, filed on Nov. 30, 1993, which is a continuation-in-part of application No. 07/976,697, filed on Nov. 13, 1992, and a continuation-in-part of application No. 09/500,295, filed on Feb. 8, 2000, which is a division of application No. 08/920,501, filed on Aug. 29, 1997, now Pat. No. 6,022,748, and a continuation-in-part of application No. 09/103,344, filed on Jun. 23, 1998, and a continuation-in-part of application No. 08/609,312, filed on Mar. 1, 1996, which is a continuation-in-part of application No. 08/389,475, filed on Feb. 13, 1995, now abandoned, which is a continuation-in-part of application No. 08/289,384, filed on Aug. 11, 1994, now abandoned, and a continuation-in-part of application No. 08/328,237, filed on Oct. 24, 1996, now abandoned, and a continuation-in-part of application No. 08/944,323, filed on Oct. 8, 1997, which is a division of application No. 08/389,475, filed on Feb. 13, 1995, now abandoned, which is a continuation-in-part of application No. 08/289,384, filed on Aug. 11, 1994, now abandoned, and a continuation-in-part of application No. 09/023,898, filed on Feb. 13, 1998, and a continuation-in-part of application No. 09/033,557, filed on Mar. 2, 1998

(60) Provisional application No. 60/090,266, filed on Jun. 22, 1998, provisional application No. 60/050,496, filed on Jun. 23, 1997, provisional application No. 60/039,749, filed on Mar. 3, 1997, and provisional application No. 60/038,383, filed on Feb. 14, 1997.

(51) Int. Cl.[7] .............................. C12Q 1/68; C07H 19/00; G01N 33/543; G01N 21/00
(52) U.S. Cl. .............................. 435/6; 435/7.1; 435/7.2; 536/22.1; 536/23.1; 536/24.3; 536/25.33; 536/24.33; 436/518; 436/528; 422/55; 422/67; 422/82.05; 422/82.09
(58) Field of Search ................................ 435/6, 7.1, 7.2; 536/22.1, 23.1, 24.3, 24.33, 25.33; 436/518, 528; 422/55, 67, 82.05, 82.09

(56) References Cited

U.S. PATENT DOCUMENTS 6,001,556 * 2/2000 Charych et al. ..................... 435/5
6,022,748 * 2/2000 Charych et al. ..................... 436/527

FOREIGN PATENT DOCUMENTS

WO 92/14843 * 9/1992 (WO).

* cited by examiner

Primary Examiner—Jezia Riley
(74) Attorney, Agent, or Firm—Medlen & Carroll, LLP

(57) ABSTRACT

The present invention relates to methods and compositions for the direct detection of analytes and membrane conformational changes through the detection of color changes in biopolymeric materials. In particular, the present invention provide for the direct colorimetric detection of analytes using nucleic acid ligands at surfaces of polydiacetylene liposomes and related molecular layer systems.

23 Claims, 53 Drawing Sheets

| SOLUBILITY IN WATER | ABILITY TO FORM FILMS AND LIPOSOMES | FILM AND LIPOSOME COLOR | BASIC COLORIMETRIC RESPONSE |
|---|---|---|---|
| HIGH | YES | BLUE | YES |
| LOW | NO | NA | NA |
| LOW | NO | NA | NA |
| HIGH | YES | BLUE | YES |
| HIGH | YES | BLUE | YES |
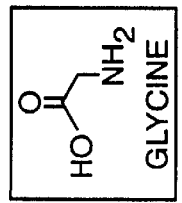
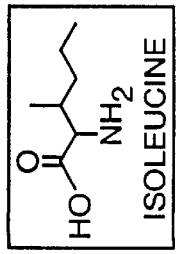
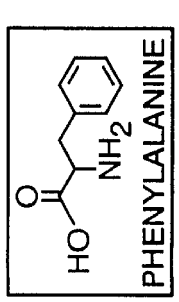
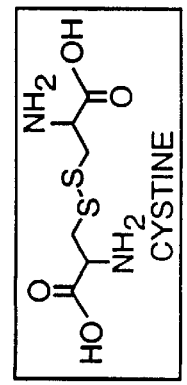
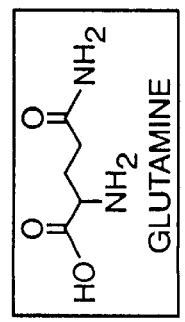
FIG. 10A

| SOLUBILITY IN WATER | ABILITY TO FORM FILMS AND LIPOSOMES | FILM AND LIPOSOME COLOR | BASIC COLORIMETRIC RESPONSE |
|---|---|---|---|
| HIGH | YES | BLUE | YES |
| HIGH | YES | DARK BLUE | YES |
| VERY HIGH | YES | DARK BLUE | NO |
| VERY HIGH | NA | NA | NA |

PROPERTIES AND COLORIMETRIC RESPONSE OF GM1 BIOSENSING MONOLAYER ASSEMBLY

| FILM COMPOSITION | INITIAL ABSORBANCE | MONOLAYER TRANSFER RATE | CR IN BUFFER | CR IN ANALYTE |
|---|---|---|---|---|
| 100% PDA | 0.052 | 0.94 | 0.02 | 0.02 |
| 5% GM1/95% PDA | 0.049 | 0.89 | 0.03 | 0.03 |
| 20% GM1/80% PDA | 0.018 | 0.34 | 0.03 | 0.04 |
| 5% SA-PDA/95% PDA | 0.038 | 0.77 | 0.06 | 0.07 |
| 20% SA-PDA/80% PDA | 0.032 | 0.62 | 0.14 | 0.15 |
| 5% GM1/5% SA-PDA/90% PDA | 0.036 | 0.87 | 0.06 | 0.28 |
| 20% GM1/5% SA-PDA/75% PDA | 0.014 | 0.33 | 0.10 | 0.13 |

FIG. 21

LIPOSOME COLOR BEFORE E.COLI TOXIN

FIG. 30 LIPOSOME COLOR AFTER E. COLI TOXIN

ACIDIC HEAD GROUP
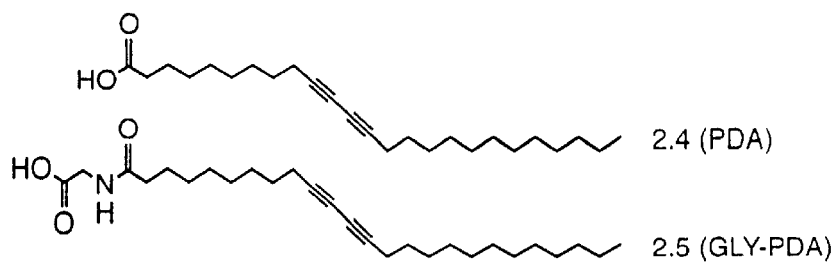
2.4 (PDA)
2.5 (GLY-PDA)
NEUTRAL HEAD GROUP
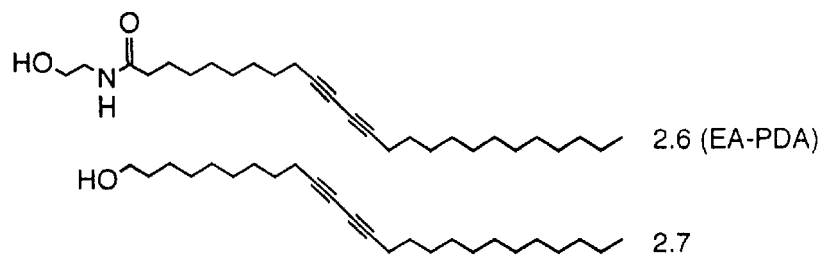
2.6 (EA-PDA)
2.7
BASIC HEAD GROUP
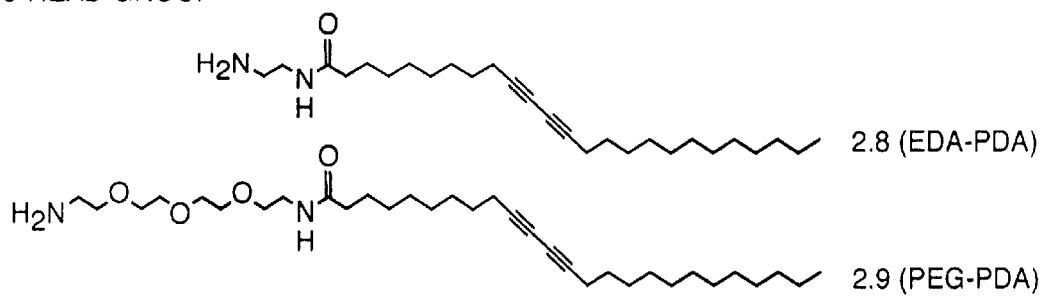
2.8 (EDA-PDA)
2.9 (PEG-PDA)
ZWITTERIONIC HEAD GROUP
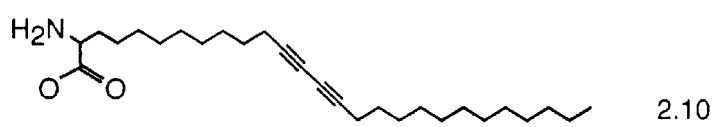
2.10
HYDROPHOBIC HEAD GROUP
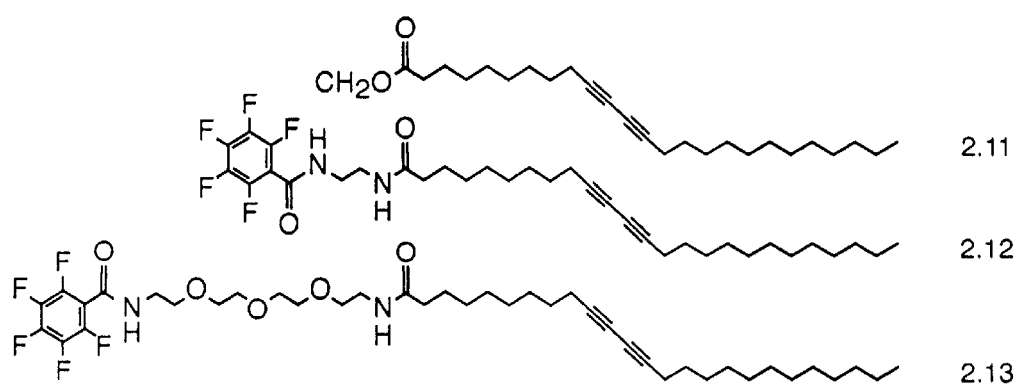
2.11
2.12
2.13
FIG. 37

DIACETYLENE LIPIDS AND PHOTOPOLYMERIZATION SCHEME

SEQUENCE LISTING

<160> NUMBER OF SEQ ID NOS: 5

<210> SEQ ID NO 1
<211> LENGTH: 27
<212> TYPE: DNA
<213> ORGANISM: Artificial Sequence
<220> FEATURE:

```
-continued

<223> OTHER INFORMATION: Description of Artificial Sequence:  Synthetic
<220> FEATURE:
<223> OTHER INFORMATION: First base is modified 5'-amino functionalized
      27-mer.

<400> SEQUENCE: 1
gaatgtatta gaatgtaatg aacttta                                              27

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:  Synthetic

<400> SEQUENCE: 2
gggaattcgt                                                                 10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence:  Synthetic

<400> SEQUENCE: 3
cccttaagca                                                                 10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence:  Synthetic

<400> SEQUENCE: 4
gggaattcgt                                                                 10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence:  Synthetic

<400> SEQUENCE: 5
gggaattcgt                                                                 10
```

NUCLEIC ACID-COUPLED COLORIMETRIC ANALYTE DETECTORS

This application claims the benefit of U.S. Provisional Application No. 60/090,266, filed Jun. 22, 1998. The present application is also a Continuation-in-Part Application of U.S. patent application Ser. No. 09/461,509, filed Dec. 14, 1999, which is a Divisional application of U.S. patent application Ser. No. 08/592,724, filed Jan. 26, 1996, now U.S. Pat. No. 6,001,556, issued Dec. 14, 1999, which is a Continuation-in-Part Application of U.S. patent application Ser. No. 08/159,927, filed Nov. 30, 1993, which is a Continuation-in-Part Application of U.S. patent application Ser. No. 07/976,697, filed Nov. 13, 1992. The present application is also a Continuation-in-Part Application of U.S. patent application Ser. No. 09/500,295, filed Feb. 8, 2000, which is a Divisional application of U.S. patent application Ser. No. 08/920,501, filed Aug. 29, 1997, now U.S. Pat. No. 6,022,748, issued Feb. 8, 2000. The present application is also a Continuation-in-Part Application of U.S. patent application Ser. No. 09/103,344, filed Jun. 23, 1998, which claims the benefit of U.S. Provisional Application No. 60/050,496, filed Jun. 23, 1997, and is also a Continuation-in-Part Application of U.S. patent application Ser. No. 08/609,312, filed Mar. 1, 1996, which is a Continuation-in-Part Application of U.S. patent application Ser. No. 08/389,475, filed Feb. 13, 1995, now abandoned, which is a Continuation-in-Part Application of U.S. patent application Ser. No. 08/289,384, filed Aug. 11, 1994, now abandoned, and U.S. patent application Ser. No. 08/328,237, filed Oct. 24, 1994, now abandoned. The present application is also a Continuation-in-Part Application of U.S. patent application Ser. No. 08/944,323, filed Oct. 8, 1997, which is a Divisional application of U.S. patent application Ser. No. 08/389,475, listed above, which is a Continuation-in-Part Application of U.S. patent application Ser. No. 8/289,384, listed above, and U.S. patent application Ser. No. 08/328,237, listed above. The present application is also a Continuation-in-Part Application of U.S. patent application Ser. No. 09/023,898, filed Feb. 13, 1998, which claims priority to U.S. Provisional Application No. 60/038,383, filed Feb. 14, 1997. The present application is also a Continuation-in-Part Application of U.S. patent application Ser. No. 09/033,557, filed Mar. 2, 1998, which claims the benefit of U.S. Provisional Application No. 60/039,749, filed Mar. 3, 1997.

This invention was made in part during work partially supported by the U.S. Department of Energy under DOE Contract No.: DE-AC03-76SF00098. The government has certain rights in the invention.

FIELD OF THE INVENTION

The present invention relates to methods and compositions for the direct detection of analytes using color changes that occur in biopolymeric material in response to selective binding of analytes.

BACKGROUND OF THE INVENTION

DNA synthesis via the automated solid-phase method, whereby the DNA fragment is built up by the sequential addition of activated nucleotides to a growing chain that is linked to an insoluble support, has provided for the synthesis of DNA chains of up to 100 nucleotides long at an approximate rate of 10 minutes per base. Such artificial DNA strands with known sequence, the single stranded probe DNA, have been used to find the complementary counterpart in DNA samples by hybridization. Above a certain temperature ($T_m$) the DNA double helix "melts" to form two complementary single strands which recombine upon cooling. If a single strand from the sample has the complementary sequence to the probe DNA they can hybridize to form a double helix. Detection of the DNA hybridization process is important for the development of methods and compositions for DNA synthesis and detection of specific nucleic acid sequences (e.g., detection of mutations, pathogens, and particular alleles). One approach for detecting DNA hybridization utilizes a quartz crystal microbalance, which is a very sensitive device to measure mass changes in the nanogram regime (Okahata et al., J. Am. Chem. Soc. 114:8299 [1992]. Another method of detecting DNA hybridization at surfaces employed the electrogenerated chemiluminescence (ECL) by intercalating an ECL marker into the double helix of the sample-probe DNA tethered to a surface (Xu et al., J. Am. Chem. Soc. 117:2627 [1995]). However, both methods are rather sensitive to interferences, such as chemical, pH, temperature, etc., and require sophisticated equipment.

There has been an increasing interest in the field of DNA sensors due to the impact of such devices on diverse areas of medical, environmental, and biological applications. (See e.g., Fodor et al., Science 251:767–773 [1991]; Maeda et al., Anal. Sciences 8:83–34 [1992]; Sakurai et al., Anal. Chem. 64:1996–1997 [1992]; Okahata et al., J. Am. Chem. Soc. 114:8299–8300 [1992]; Xu et al., J. Am. Chem. Soc. 117:2627–2631 [1995]; and Wang et al., Anal. Chem. 68:2629–2634 [1996]). Besides pure sequencing applications, such DNA sensors could help detect infectious or inherited diseases, or as RNA sensors, aid in monitoring expression levels of specific metabolic pathways to determine environmental pollution. DNA hybridization between a synthetic oligodeoxynucleotide of known sequence and its complement in a given sample provides a powerful tool for the detection and sequencing of DNA and RNA. The hybridization event itself is usually monitored by introducing fluorescent markers and radioactive labels or by applying antibody assays and enzyme reactions to the specifically modified DNA (or RNA) pair, which generally requires labor intensive and time consuming multistep procedures.

Thus, there remains a need of analyte detectors that provide for DNA detection that can be visually monitored by the naked eye, thus, making any further detection procedures ancillary or unnecessary.

SUMMARY OF THE INVENTION

The present invention relates to methods and compositions for the direct detection of analytes using color changes that occur in biopolymeric material in response to selective binding of analytes. In one embodiment, the biopolymeric material comprises self-assembling monomers. In another embodiment, the self-assembling monomers are lipids.

The present invention contemplates biopolymeric materials comprising a plurality of polymerized self-assembling monomers and one or more nucleic acid ligands, wherein said biopolymeric materials change color in the presence of an analyte. In some embodiments, the nucleic acids have affinity for an analyte. In other embodiments, the nucleic acid ligands are single stranded nucleic acid sequences. In a further embodiment, the nucleic acid ligands are linked to said polymerized self-assembling monomers through one or more covalent bonds. In yet another embodiment, the covalent bonds are selected from the group consisting of amine bonds, thiol bonds, and aldehyde bonds.

In a preferred embodiment of the present invention, the biopolymeric materials contains nucleic acids as ligands that have affinity for an analyte. In one embodiment, the nucleic acid ligands have affinity for an analyte selected from the group of nucleic acid molecules, enzymes, pathogens, drugs, receptor ligands, antigens, ions, proteins, hormones, blood components, antibodies, and lectins. In further embodiments, the analytes are nucleic acid molecules are from any organism (including microorganisms, including, but not limited to bacteria, fungi, viruses, etc.), cell, plasmid, or expression vector. In another embodiment, the analytes which are nucleic acid molecules are selected from ribosomal RNA, transfer RNA, messenger RNA, intron RNA, double stranded RNA, single stranded RNA, single stranded DNA, double stranded DNA, DNA-RNA hybrid molecules, PNA, PNA-DNA or PNA-RNA hybrid molecules, nucleic acid sequences characteristic of human pathogens, nucleic acid sequences characteristic of non-human pathogens, and nucleic acid sequences characteristic of genetic abnormalities (e.g., cystic fibrosis, Tay-Sachs disease, cretinism, phenylketonuria (PKU), sickle-cell anemia, diabetes insipidus, retinoblastoma, hemophilia, Deuchenne-type muscular dystrophy, Klinefelter's syndrome, Turner's syndrome, and trisomy-21 (i.e., Down's syndrome)). In additional embodiments, the analytes are enzymes including, but not limited to, polymerases, nucleases, ligases, telomerases, and transcription factors.

The present invention also contemplates biopolymeric materials comprising nucleic acid ligands that have affinity for analytes that are pathogens. It is not intended that the present invention be limited to any particular pathogen analyte(s), as a variety of pathogen analytes are contemplated. In one embodiment, the pathogens are selected from viruses, bacteria, parasites, and fingi. In further embodiments, the pathogens are viruses selected from influenza, rubella, varicella-zoster, hepatitis A, hepatitis B, other hepatitis viruses, herpes simplex, polio, smallpox, human immunodeficiency virus, vaccinia, rabies, Epstein Barr, retroviruses, and rhinoviruses. In another embodiment, the pathogens are bacteria selected from *Escherichia coli*, *Mycobacterium tuberculosis*, Salmonella, Chiamydia and Streptococcus. In yet a further embodiment, the pathogens are parasites selected from Plasmodium, Trypanosoma, *Toxoplasma gondii*, and Onchocerca. However, it is not intended that the present invention be limited to the specific genera and/or species listed above.

In certain embodiments, the biopolymeric materials comprise biopolymeric films. In other embodiments, the biopolymeric materials comprise biopolymeric liposomes. In yet other embodiments, the biopolymeric materials are selected from the group consisting of tubules, braided assemblies, lamellar assemblies, helical assemblies, fiber-like assemblies, solvated rods, and solvated coils.

In some embodiments, the self-assembling monomers of the biopolymeric material of the present invention comprise diacetylene monomers. In certain embodiments, the diacetylene monomers are selected from the group consisting of 5,7-docosadiynoic acid, 5,7-pentacoadiynoic acid, 10,12-pentacosadiynoic acid, and combinations thereof, although all diacetylene monomers are contemplated by the present invention. In other embodiments, the self-assembling monomers are selected from the group consisting of acetylenes, alkenes, thiophenes, polythiophenes, imides, acrylamides, methacrylates, vinylether, malic anhydride, urethanes, allylamines, siloxanes anilines, pyrroles, vinylpyridinium, and combinations thereof. In certain embodiments, the self-assembling monomers contain head groups selected from the group consisting of carboxylic acid, hydroxyl groups, amine groups, amino acid derivatives, and hydrophobic groups, although other head groups are also contemplated by the present invention.

The present invention also contemplates biopolymeric materials further comprising dopant materials. However, it is not intended that the present invention be limited to certain dopant materials, as a variety of dopant materials are contemplated. In one embodiment the dopant materials are selected from the group consisting of surfactants, polysorbate, octoxynol, sodium dodecyl sulfate, polyethylene glycol, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cholesterol, steroids, cerebroside, lysophosphatidylcholine, D-erythroshingosine, sphingomyelin, dodecyl phosphocholine, and N-biotinyl phosphatidylethanolamine. In another embodiment, the dopant material is a diacetylene derivative selected from the group consisting of sialic acid-derived diacetylene, lactose-derived diacetylene, and amino-derived diacetylene.

The present invention also contemplates biopolymeric materials further comprising one or more non-nucleic acid ligands. However, it is not intended that the present invention be limited to certain non-nucleic acid ligands, as a variety of non-nucleic acid ligands are contemplated. In one embodiment the non-nucleic acid ligands are selected from the group consisting of carbohydrates, proteins, drugs, chromophores, antigens, chelating compounds, molecular recognition complexes, ionic groups, polymerizable groups, linker groups, electron donors, electron acceptor groups, hydrophobic groups, hydrophilic groups, receptor binding groups, trisaccharides, tetrasaccharides, ganglioside $G_{M1}$, ganglioside $G_{T1b}$, sialic acid, and combinations thereof.

In some embodiments of the present invention, the biopolymeric materials further comprise a support, wherein the biopolymeric materials are immobilized to the support. In certain embodiments, the support is selected from the group consisting of polystyrene, polyethylene, teflon, mica, sephadex, sepharose, polyacrynitriles, filters, glass, gold, silicon chips, and silica. In other embodiments, the support comprises porous silica glass, wherein the biopolymeric materials are immobilized within the porous silica glass, although the present invention contemplates a variety of other supports.

The present invention also provides devices comprising one or more of the biopolymeric materials described above, wherein the biopolymeric materials are immobilized to the device.

The present invention further provides methods for detecting the presence of an analyte. In particularly preferred embodiments, the methods comprise the steps of providing biopolymeric materials comprising a plurality of polymerized lipid monomers and one or more ligands wherein the biopolymeric materials change color in the presence of analyte, and a sample suspected of containing an analyte; contacting the biopolymeric materials with the sample; and detecting a color change in the biopolymeric materials. In some embodiments, the ligands are nucleic acid ligands.

Furthermore, the present invention provides biopolymeric materials for analyses such as methods to calorimetrically detect DNA hybridization. The present invention also provides methods for detecting the presence of nucleic acid hybridization. In particularly preferred embodiments, the methods comprise the steps of providing one or more nucleic acid hybrids to be detected, and biopolymeric materials comprising a plurality of polymerized lipid monomers and one or more ligands with affinity for the nucleic acid to be detected; contacting the biopolymeric materials with the nucleic acid to be detected; and detecting the presence of nucleic acid.

DESCRIPTION OF THE FIGURES

FIG. 10A shows the properties of biopolymeric materials composed of amino acid-derivated diacetylene monomers.

FIG. 21 shows the properties of polydiacetylene monolayers with and without sialic acid-derived PDA and ganglioside $G_{M1}$.

FIG. 37 shows derivations of PDA for use in detection arrays.

FIGS. 40–50 show various embodiments of nucleic acid-coupled biopolymeric material generation and use. In particular.

DEFINITIONS

Figure 1:
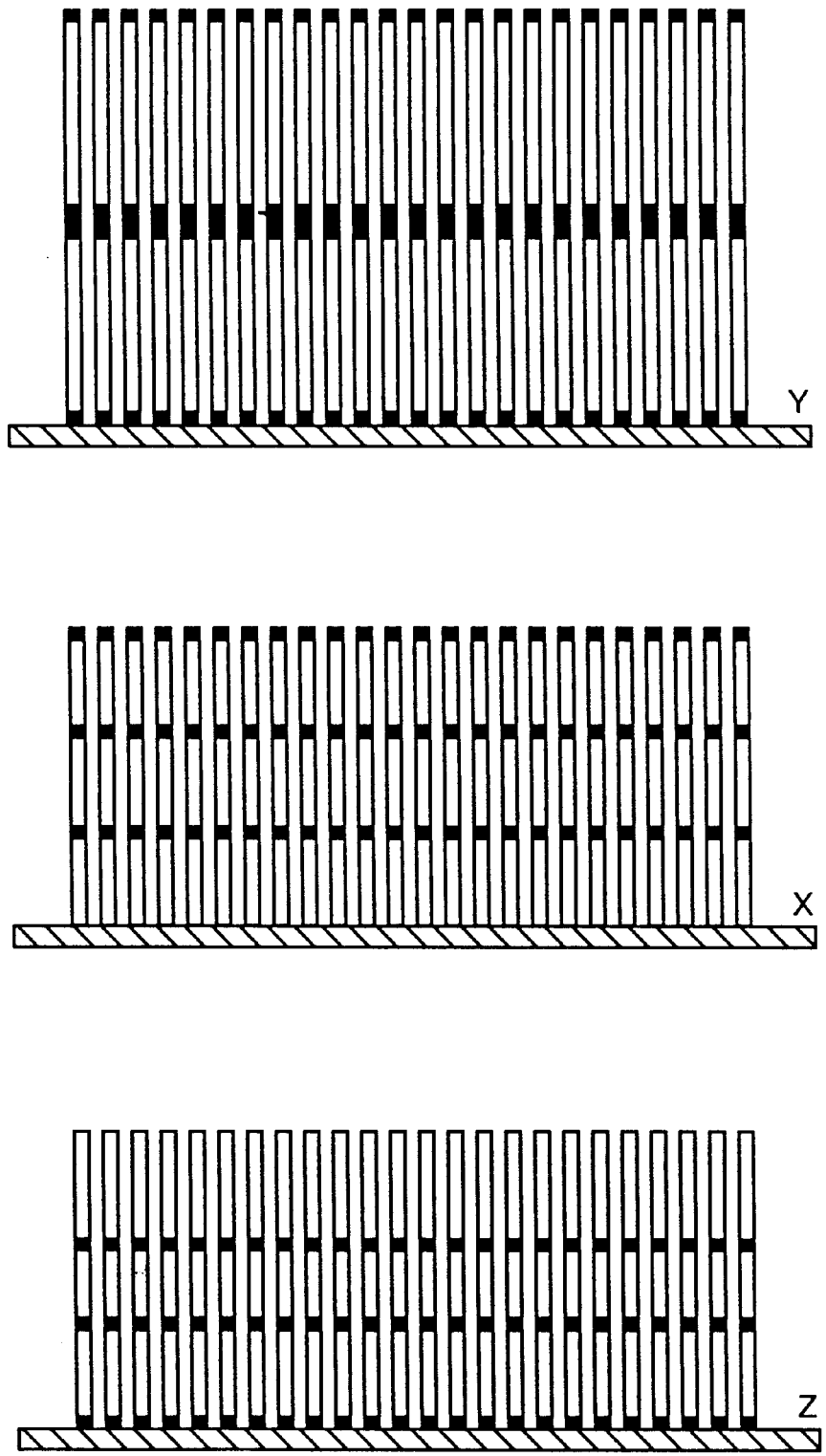
FIG. 1 shows a schematic representation of biopolymeric films. Y is a centrosymmetric multilayer film, while films X and Z are noncentrosymmetric multilayers.

To facilitate an understanding of the present invention, a number of terms and phrases are defined below:

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition below for "stringency").

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "polymerase chain reaction" ("PCR") refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "antisense" is used in reference to DNA or RNA sequences that are complementary to a specific DNA or RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "non-synthetic synthesis" refers to the synthesis of biopolymeric materials, whereby one or more components of the assembly is not part of the polymer backbone. For example, in some embodiments of the present invention, ganglioside is used as a ligand for the direct detection of analytes (e.g., cholera toxin), where the ganglioside ligands are incorporated into the assemblies, but are not part of the polymerized network.

As used herein, the term "reaction" refers to any change or transformation in which a substance (e.g., molecules, membranes, and molecular assemblies) combines with other substances, interchanges constituents with other substances, decomposes, rearranges, or is otherwise chemically altered. As used herein, the term "reaction means" refers to any means of initiating and/or catalyzing a reaction. Such reaction means include, but are not limited to, enzymes, temperature changes, and pH changes. The phrase "affinity for said reaction means" refers to compounds with the ability to specifically associate (e.g., bind) to a given reaction mean, although not necessarily a substrate for the reaction means. For example, a $PLA_2$ antibody has affinity for $PLA_2$, but is not the substrate for the enzyme.

As used herein, the term "immobilization" refers to the attachment or entrapment, either chemically or otherwise, of material to another entity (e.g. a solid support) in a manner that restricts the movement of the material.

As used herein, the terms "material" and "materials" refer to, in their broadest sense, any composition of matter.

As used herein, the term "biopolymeric material" refers to materials composed of polymerized biological molecules (e.g., lipids, proteins, carbohydrates, and combinations thereof). Such materials include, but are not limited to, films, vesicles, liposomes, multilayers, aggregates, membranes, and solvated polymers (e.g., polythiophene aggregates such as rods and coils in solvent). In some embodiments, biopolymeric material comprises molecules that are not part of the polymerized matrix (i.e., molecules that are not polymerized).

As used herein the term "protein" is used in its broadest sense to refer to all molecules or molecular assemblies containing two or more amino acids. Such molecules include, but are not limited to, proteins, peptides, enzymes, antibodies, receptors, lipoproteins, and glycoproteins.

As used herein the term "antibody" refers to a glycoprotein evoked in an animal by an immunogen (antigen). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., VH and VL respectively), which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "biopolymeric films" refers to polymerized organic films that are used in a thin section or in a layer form. Such films can include, but are not limited to, monolayers, bilayers, and multilayers. Biopolymeric films mimic biological cell membranes (e.g., in their ability to interact with other molecules such as proteins or analytes).

As used herein, the term "sol-gel" refers to preparations composed of porous metal oxide glass structures. Such structures can have biological or other material entrapped within the porous structures. The phrase "sol-gel matrices" refers to the structures comprising the porous metal oxide glass with or without entrapped material. The term "sol-gel material" refers to any material prepared by the sol-gel process including the glass material itself and any entrapped material within the porous structure of the glass. As used herein, the term "sol-gel method" refers to any method that results in the production of porous metal oxide glass. In some embodiments, "sol-gel method" refers to such methods conducted under mild temperature conditions. The terms "sol-gel glass" and "metal oxide glass" refer to glass material prepared by the sol-gel method and include inorganic material or mixed organic/inorganic material. The materials used to produce the glass can include, but are not limited to, aluminates, aluminosilicates, titanates, ormosils (organically modified silanes), and other metal oxides.

As used herein, the term "direct colorimetric detection" refers to the detection of color changes without the aid of an intervening processing step (e.g. conversion of a color change into an electronic signal that is processed by an interpreting device). It is intended that the term encompass visual observing (e.g., observing with the human eye) as well as detection by simple spectrometry.

As used herein, the term "analytes" refers to any material that is to be analyzed. Such materials include, but are not limited to, ions, molecules, antigens, bacteria, compounds, viruses, cells, antibodies, and cell parts.

As used herein, the term "selective binding" refers to the binding of one material to another in a manner dependent upon the presence of a particular molecular structure (i.e., specific binding). For example, a receptor will selectively bind ligands that contain the chemical structures complementary to the ligand binding site(s). This is in contrast to "non-selective binding," whereby interactions are arbitrary and not based on structural compatibilities of the molecules.

As used herein, the term "biosensors" refers to any sensor device that is partially or entirely composed of biological molecules. In a traditional sense, the term refers to "an analytical tool or system consisting of an immobilized biological material (such as enzyme, antibody, whole cell, organelle, or combination thereof) in intimate contact with a suitable transducer device which will convert the biochemical signal into a quantifiable electrical signal" (Gronow, Trends Biochem. Sci. 9: 336 [1984]).

As used herein, the term "transducer device" refers to a device that is capable of converting a non-electrical phenomenon into electrical information, and transmitting the information to a device that interprets the electrical signal. Such devices include, but are not limited to, devices that use photometry, fluorimetry, and chemiluminescence; fiber optics and direct optical sensing (e.g., grating coupler); surface plasmon resonance; potentiometric and amperometric electrodes; field effect transistors; piezoelectric sensing; and surface acoustic wave.

As used herein, the term "miniaturization" refers to a reduction in size, such as the size of a sample to increase utility (e.g., portability, ease of handling, and ease of incorporation into arrays).

As used herein, the term "stability" refers to the ability of a material to withstand deterioration or displacement and to provide reliability and dependability.

As used herein, the term "conformational change" refers to the alteration of the molecular structure of a substance. It is intended that the term encompass the alteration of the structure of a single molecule or molecular aggregate (e.g., the change in structure of polydiacetylene upon interaction with an analyte).

As used herein, the term "small molecules" refers to any molecule with low molecular weight (i.e., less than 10,000 atomic mass units and preferably less than 5,000 atomic mass units) that binds to ligands, interacts with ligands, or interacts with biopolymeric material in a manner that creates a conformational change.

As used herein, the term "pathogen" refers to disease causing organisms, microorganisms, or agents including, but not limited to, viruses, bacteria, parasites (including, but not limited to, organisms within the phyla Protozoa, Platyhelminthes, Aschehninithes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), C V Mosby St. Louis, pp 13–15).

As used herein, the term "membrane" refers to, in its broadest sense, a sheet or layer of material. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterols and/or other components. As used herein, the term "membrane fragment" refers to any portion or piece of a membrane. The term "polymerized membrane" refers to membranes that have undergone partial or complete polymerization.

As used herein, the terms "membrane rearrangement" and "membrane conformational change" refer to any alteration in the structure of a membrane. Such alterations can be caused by physical perturbation, heating, enzymatic and chemical reactions, among other events. Reactions that can result in membrane rearrangement include, but are not limited to lipid cleavage, polymerization, lipid flipping, transmembrane signalling, vesicle formation, lipidation, glycosylation, ion channeling, molecular rearrangement, and phosphorylation. Enzymatic catalysis that results in membrane rearrangement can result from free enzymes interacting with the biopolymeric material (e.g., reacting with an enzyme substrate in the biopolymeric material) and can result from enzymatic activity present in certain analytes (e.g., viruses, bacteria, and toxins among others).

As used herein, the term "lipid cleavage" refers to any reaction that results in the division of a lipid or lipid-comprising material into two or more portions. "Lipid cleavage means" refers to any means of initiating and/or catalyzing lipid cleavage. Such lipid cleavage means include, but are not limited to enzymes, free radical reactions, and temperature changes.

As used herein, the term "polymerization" encompasses any process that results in the conversion of small molecular monomers into larger molecules consisting of repeated units. Typically, polymerization involves chemical crosslinking of monomers to one another.

As used herein, the term "membrane receptors" refers to constituents of membranes that are capable of interacting with other molecules or materials. Such constituents can include, but are not limited to, proteins, lipids, carbohydrates, and combinations thereof.

As used herein, the term "volatile organic compound" or "VOC" refers to organic compounds that are reactive (i.e., evaporate quickly, explosive, corrosive, etc.), and typically are hazardous to human health or the environment above certain concentrations. Examples of VOCs include, but are not limited to, alcohols, benzenes, toluenes, chloroforms, and cyclohexanes.

As used herein, the term "enzyme" refers to molecules or molecule aggregates that are responsible for catalyzing chemical and biological reactions. Such molecules are typically proteins, but can also comprise short peptides, RNAs, ribozymes, antibodies, and other molecules.

As used herein, the term "substrate," in one sense, refers to a material or substance on which an enzyme or other reaction means acts. In another sense, it refers to a surface on which an sample grows or is attached. The term "reaction substrate" refers to the substrate for a reaction means (e.g., a "substrate lipid" reacted by a lipid cleavage means). As used herein, the term "analyte substrate" refers to a material or substance upon which an analyte reacts. For example, the analyte can be an enzyme and the analyte substrate is an enzyme substrate. In another sense, the analyte can be a pathogen and the analyte substrate comprises a material or sample that is altered by a "reaction means" associated with the pathogen.

As used herein, the term "lipase" refers to any of a group of hydrolytic enzymes that acts on ester bonds in lipids. Such lipases include, but are not limited to, pancreatic lipase that catalyses the hydrolysis of triacylglycerols, lipoprotein lipase that catalyzes the hydrolysis of triacylglycerols to glycerol and free fatty acids, and phospholipases, among others. The term "phospholipase" refers to enzymes that cleave phospholipids by the hydrolysis of carbon-oxygen or phosphorus-oxygen bonds. Phospholipases include, but are not limited to, phospholipases $A_1$, $A_2$, C, and D.

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the term "peptide" refers to any substance composed of two or more amino acids.

As used herein, the term "carbohydrate" refers to a class of molecules including, but not limited to, sugars, starches, cellulose, chitin, glycogen, and similar structures. Carbohydrates can also exist as components of glycolipids and glycoproteins.

As used herein, the term "chromophore" refers to molecules or molecular groups responsible for the color of a compound, material, or sample.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the term "chelating compound" refers to any compound composed of or containing coordinate links that complete a closed ring structure. The compounds can combine with metal ions, attached by coordinate bonds to at least two of the nonmetal ions.

As used herein, the term "molecular recognition complex" refers to any molecule, molecular group, or molecular complex that is capable of recognizing (i.e., specifically interacting with) a molecule. For example, the ligand binding site of a receptor would be considered a molecular recognition complex.

As used herein, the term "ambient condition" refers to the conditions of the surrounding environment (e.g., the temperature of the room or outdoor environment in which an experiment occurs).

As used herein, the term "room temperature" refers, technically, to temperatures approximately between 20 and 25 degrees centigrade. However, as used generally, it refers to the any ambient temperature within a general area in which an experiment is taking place.

As used herein, the terms "home testing" and "point of care testing" refer to testing that occurs outside of a laboratory environment. Such testing can occur indoors or outdoors at, for example, a private residence, a place of business, public or private land, in a vehicle, under water, as well as at the patient's bedside.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

As used herein, the phrase "free floating aggregates" refers to aggregates that are not immobilized.

As used herein, the term "encapsulate" refers to the process of encompassing, encasing, or otherwise associating two or more materials such that the encapsulated material is immobilized within or onto the encapsulating material.

As used herein, the term "optical transparency" refers to the property of matter whereby the matter is capable of transmitting light such that the light can be observed by visual light detectors (e.g., eyes and detection equipment).

As used herein, the term "biologically inert" refers to a property of material whereby the material does not chemically react with biological material.

As used herein, the term "organic solvents" refers to any organic molecules capable of dissolving another substance. Examples include, but are not limited to, chloroform, alcohols, phenols, and ethers.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, exist as solvated polymers in aggregate forms such as rods and coils.

As used herein, the term "films" refers to any material deposited or used in a thin section or in a layer form.

As used herein, the term "vesicle" refers to a small enclosed structures. Often the structures are membranes composed of lipids, proteins, glycolipids, steroids or other components associated with membranes. Vesicles can be naturally generated (e.g., the vesicles present in the cytoplasm of cells that transport molecules and partition specific cellular functions) or can be synthetic (e.g. liposomes).

As used herein, the term "liposome" refers to artificially produced spherical lipid complexes that can be induced to segregate out of aqueous media. The terms "liposome" and "vesicle" are used interchangeably herein.

As used herein, the term "biopolymeric liposomes" refers to liposomes that are composed entirely, or in part, of biopolymeric material.

As used herein, the term "tubules" refers to materials comprising small hollow cylindrical structures.

As used herein, the terms "solvated polymer," "solvated rod," and "solvated coil" refer to polymerized materials that are soluble in aqueous solution.

As used the term "multilayer" refers to structures comprised of two or more monolayers. The individual monolayers may chemically interact with one another (e.g., through covalent bonding, ionic interactions, van der Waals' interactions, hydrogen bonding, hydrophobic or hydrophilic assembly, and stearic hindrance) to produce a film with novel properties (i.e., properties that are different from those of the monolayers alone).

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g. a single lipid molecule) and small molecular assemblies (e.g., polymerized lipids), whereby the individual small molecular assemblies can be further aggregated (e.g., assembled and polymerized) into larger molecular assemblies. "Surfactant molecular assemblies" refers to an assembly of surface active agents that contain chemical groups with opposite polarity, form oriented monolayers at phase interfaces, form micelles (colloidal particles in aggregation colloids), and have detergent, foaming, wetting, emulsifying, and dispersing properties.

As used herein, the term "homopolymers" refers to materials comprised of a single type of polymerized molecular species. The phrase "mixed polymers" refers to materials comprised of two or more types of polymerize molecular species.

As used herein, the term "ligands" refers to any ion, molecule, molecular group, or other substance that binds to another entity to form a larger complex. Examples of ligands include, but are not limited to, peptides, carbohydrates, nucleic acids (e.g., DNA and RNA), antibodies, or any molecules that bind to receptors.

As used herein, the term "dopant" refers to molecules that are added to biopolymeric materials to change the material's properties. Such properties include, but are not limited to, calorimetric response, color, sensitivity, durability, robustness, amenability to immobilization, temperature sensitivity, and pH sensitivity. Dopant materials include, but are not limited to, lipids, cholesterols, steroids, ergosterols, polyethylene glycols, proteins, peptides, or any other molecule (e.g., surfactants, polysorbate, octoxynol, sodium dodecyl sulfate, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cerebroside, lysophosphatidylcholine, D-erythroshingosine, sphingomyelin, dodecyl phosphocholine, N-biotinyl phosphatidylethanolamine, and other synthetic or natural components of cell membranes) that can be associated with a membrane (e.g., liposomes and films).

As used herein, the terms "organic matrix" and "biological matrix" refer to collections of organic molecules that are assembled into a larger multi-molecular structure. Such structures can include, but are not limited to, films, monolayers, and bilayers. As used herein, the term "organic monolayer" refers to a thin film comprised of a single layer of carbon-based molecules. In one embodiment, such monolayers can be comprised of polar molecules whereby the hydrophobic ends all line up at one side of the monolayer. The term "monolayer assemblies" refers to structures comprised of monolayers. The term "organic polymetric matrix" refers to organic matrices whereby some or all of the molecular constituents of the matrix are polymerized.

As used herein, the terms "head group" and "head group functionality" refer to the molecular groups present an the ends of molecules (e.g., the carboxylic acid group at the end of fatty acids).

As used herein, the term "hydrophilic head-group" refers to ends of molecules that are substantially attracted to water by chemical interactions including, but not limited to, hydrogen-bonding, van der Waals' forces, ionic interactions, or covalent bonds. As used herein, the term "hydrophobic head-group" refers to ends of molecules that self-associate with other hydrophobic entities, resulting in their exclusion from water.

As used herein, the term "carboxylic acid head groups" refers to organic compounds containing one or more carboxyl (—COOH) groups located at, or near, the end of a molecule. The term carboxylic acid includes carboxyl groups that are either free or exist as salts or esters.

As used herein, the term "detecting head group" refers to the molecular group contained at the end of a molecule that is involved in detecting a moiety (e.g., an analyte).

As used herein, the term "linker" or "spacer molecule" refers to material that links one entity to another. In one sense, a molecule or molecular group can be a linker that is covalent attached two or more other molecules (e.g. linking a ligand to a self-assembling monomer).

As used herein, the phrase "polymeric assembly surface" refers to polymeric material that provides a surface for the assembly of further material (e.g., a biopolymeric surface of a film or liposome that provides a surface for attachment and assembly of ligands).

As used herein, the term "formation support" refers to any device or structure that provides a physical support for the production of material. In some embodiments, the formation support provides a structure for layering and/or compressing films.

As used herein, the term "diacetylene monomers" refers to single copies of hydrocarbons containing two alkyne linkages (i.e., carbon/carbon triple bonds).

As used herein, the terms "standard trough" and "standard Langmuir-Blodgett trough" refer to a device, usually made of teflon, that is used to produce Langmuir films. The device contains a reservoir that holds an aqueous solution and moveable barriers to compress film material that are layered onto the aqueous solution (See e.g., Roberts, *Langmuir-Blodgett Films*, Plenum, N.Y., [1990]).

As used herein, the term "crystalline morphology" refers to the configuration and structure of crystals that can include, but are not limited to, crystal shape, orientation, texture, and size.

As used herein, the term "domain boundary" refers to the boundaries of an area in which polymerized film molecules are homogeneously oriented. For example, a domain boundary can be the physical structure of periodic, regularly arranged polydiacetylene material (e.g., striations, ridges, and grooves).

As used herein, the term "domain size" refers to the typical length between domain boundaries.

As used the terms "conjugated backbone" and "polymer backbone" refer to the ene-yne polymer backbone of polymerized diacetylenic films that, on a macroscopic scale, appears in the form of physical ridges or striations. The term "polymer backbone axis" refers to an imaginary line that runs parallel to the conjugated backbone. The terms "intrabackbone" and "interbackbone" refer to the regions within a given polymer backbone and between polymer backbones, respectively. The backbones create a series of lines or "linear striations," that extend for distances along the template surface.

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., $C_8$–$C_9$). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used the term "absorption" refers, in one sense, to the absorption of light. Light is absorbed if it is not reflected from or transmitted through a sample. Samples that appear colored have selectively absorbed all wavelengths of white light except for those corresponding to the visible colors that are seen.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "ultraviolet irradiation" refers to exposure to radiation with wavelengths less than that of visible light (i.e., less than approximately 360 nM) but greater than that of X-rays (i.e., greater than approximately 0.1 nM). Ultraviolet radiation possesses greater energy than visible light and is therefore, more effective at inducing photochemical reactions.

As used herein, the term "chromatic transition" refers to the changes of molecules or material that result in an alteration of visible light absorption. In some embodiments, chromatic transition refers to the change in light absorption of a sample, whereby there is a detectable color change associated with the transition. This detection can be accomplished through various means including, but not limited to, visual observation and spectrophotometry.

As used herein, the term "thermochromic transition" refers to a chromatic transition that is initiated by a change in temperature.

As used herein, the term "solid support" refers to a solid object or surface upon which a sample is layered or attached. Solid supports include, but are not limited to, glass, metals, gels, and filter paper, among others. "Hydrophobized solid support" refers to a solid support that has been chemically treated or generated so that it attracts hydrophobic entities and repels water.

As used herein, the term "film-ambient interface" refers to a film surface exposed to the ambient environment or atmosphere (i.e., not the surface that is in contact with a solid support).

As used herein, the term "formation solvent" refers to any medium, although typically a volatile organic solvent, used to solubilize and distribute material to a desired location (e.g., to a surface for producing a film or to a drying receptacle to deposit liposome material for drying).

As used herein, the term "micelle" refers to a particle of colloidal size that has a hydrophilic exterior and hydrophobic interior.

As used herein, the term "topochemical reaction" refers to reactions that occur within a specific place (e.g., within a specific portion of a molecule or a reaction that only occurs when a certain molecular configuration is present).

As used herein, the term "molding structure" refers to a solid support used as a template to design material into desired shapes and sizes.

As used herein, the terms "array" and "patterned array" refer to an arrangement of elements (i.e., entities) into a material or device. For example, combining several types of biopolymeric material with different analyte recognition groups into an analyte-detecting device, would constitute an array.

As used herein the term "interferants" refers to entities present in an analyte sample that are not the analyte to be detected and that, preferably, a detection device will not identify, or would differentiate from the analyte(s) of interest.

As used herein, the term "badge" refers to any device that is portable and can be carried or worn by an individual working in an analyte detecting environment.

As used herein, the term "device" refers to any apparatus (e.g., multi-well plates and badges) that contain biopolymeric material. The biopolymeric material may be immobilized or entrapped in the device. More than one type of biopolymeric material can be incorporated into a single device.

As used herein, the term "halogenation" refers to the process of incorporating or the degree of incorporation of halogens (i.e., the elements fluorine, chlorine, bromine, iodine and astatine) into a molecule.

As used herein, the term "aromaticity" refers to the presence of aromatic groups (i.e., six carbon rings and derivatives thereof) in a molecule.

As used herein, the phrase "water-immiscible solvents" refers to solvents that do not dissolve in water in all proportions. The phrase "water-miscible solvents" refers to solvents that dissolve in water in all proportions.

As used herein, the terms "positive," "negative," and "zwitterionic charge" refer to molecules or molecular groups that contain a net positive, negative, or neutral charge, respectively. Zwitterionic entities contain both positively and negatively charged atoms or groups whose charges cancel (i.e., whose net charge is 0).

As used herein, the term "biological organisms" refers to any carbon-based life forms.

As used herein, the term "in situ" refers to processes, events, objects, or information that are present or take place within the context of their natural environment.

As used the term "aqueous" refers to a liquid mixture containing water, among other components.

As used herein, the term "solid-state" refers to reactions involving one or more rigid or solid-like compounds.

As used herein, the term "regularly packed" refers to the periodic arrangement of molecules within a compressed film.

As used herein, the term "filtration" refers to the process of separating various constituents within a test sample from one another. In one embodiment, filtration refers to the separation of solids from liquids or gasses by the use of a membrane or medium. In alternative embodiments, the term encompasses the separation of materials based on their relative size.

As used herein, the term "inhibitor" refers to a material, sample, or substance that retards or stops a chemical reaction. The term "reaction means inhibitor" refers to inhibitors that are capable of retarding or stopping the action or activity of a given reaction means (e.g., an enzyme).

As used herein, the term "inhibitor screening" refers to any method used to identify and/or characterize inhibitors. Preferably, inhibitor screening methods provide "high throughput screening," the ability to screen a large number of samples suspected of containing inhibitors in a short period of time. It may also be desired that the inhibitor screening method provide quantifiable results to provide comparisons of inhibitor efficiency.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

GENERAL DESCRIPTION OF THE INVENTION

The present invention relates to methods and compositions for the direct detection of membrane conformational changes through the detection of color changes in biopolymeric materials. In one embodiment of the present invention, the polydiacetylene sensors composed of fully conjugated polymer backbones embedded in lipid bilayers, undergo colorimetric transitions upon a specific binding event between a surface bound ligand and a receptor or host molecule in the sample specimen. The chromophoric detection unit is built into the sensor and can be visually monitored by the naked eye, making any further detection procedures unnecessary. In one embodiment of the present invention, attachment of synthetic oligodeoxynucleotides to such sensor surfaces provides devices that allow direct detection of nucleic acid hybridization events by calorimetric transition.

In preferred embodiments of the present invention, ligands that allow direct colorimetric detection of nucleic acid hybridization are incorporated into polymerized biosensors. In particular, the present invention provides methods and compositions related to the specific detection of nucleic acid hybridization via recognition of a single stranded sample nucleic acid with a single stranded probe nucleic acid, which is covalently attached to the surface of the biopolymeric material of the present invention. A visible transition from blue to the red form of the biopolymeric material allows specific detection of nucleic acid hybridization. This colorimetric response upon nucleic acid hydribidization provides a quick and simple detection of specific nucleic acid fragments (e.g., produced by the PCR) or as a diagnostic tool in medicine. Additionally, the nucleic acid-linked biopolymeric material provides a means to detect the presence and activity of enzymes or other molecule that associate with or alter nucleic acid samples. In some embodiments, the present invention provide compositions and methods related to the construction, characterization and optimization of patterned nucleic acid sensors based on the photochromic transition in biopolymeric materials upon nucleic acid hybridization.

In some embodiments of the present invention, an array of patterned nucleic acid assays are incorporated into a single device, such that parallel detection of many different hybridization events occurs simultaneously. Such arrays are designed so that the presence of a given analyte produces a color change in a known location in the device, or that produces a color change specific to the given analyte (e.g. purple to orange for analyte 1 and blue to red for analyte 2). It is also contemplated that other arrays are used with the present invention, including such easily understood patterns as a "+" sign to indicate that presence of a particular substance or compound. It is not intended that the present invention be limited to any particular array design or configuration.

DETAILED DESCRIPTION OF THE INVENTION

The present invention comprises methods and compositions related to biopolymeric materials that change color in response to membrane rearrangements through ligand analyte binding or other rearrangements. These biopolymeric materials comprise many forms including, but not limited to, films, vesicles, tubules, multilayered structures, and solvated rods and coils. These biopolymeric materials are comprise polymerized self-assembling monomers. In some embodiments, the biopolymeric materials comprise more than one species of self-assembling monomer. Some of these self-assembling monomers may lack polymerizable groups. In other embodiments, the materials further comprise dopant material(s) that alter the properties of the sensor. Dopants include, but are not limited to, polymerizable self-assembling monomers, non-polymerizable self-assembling monomers, lipids, sterols, membrane components, and any other molecule that optimizes the biopolymeric material (e.g., material stability, durability, colorimetric response, and immobilizability). The biopolymeric material may further comprise ligands (e.g., proteins, antibodies, carbohydrates, and nucleic acids). The ligands provide attachment sites for recruiting molecules to the biopolymeric surface or are used as binding sites for analytes, whereby the binding event causes a colorimetric change in the biopolymeric material. The various embodiments of the present invention provide the ability to colorimetrically detect a broad range reactions and analytes. With certain biopolymeric materials, a color transition in response to a reaction is viewed by simple visual observation or, if desired, by color sensing equipment. The present invention further provides a variety of means of immobilizing the biopolymeric material to provide stability, durability, and ease of handling and use. In some embodiments, a variety of different polymeric materials are combined into a single device to produce an array. The array is designed to detect and differentiate differing types or quantities of reactions or analytes (i.e., the array can provide quantitative and/or qualitative data). The methods and compositions of the present invention find use in a broad range of analyte detection circumstances and are particularly amenable to situations where simple, rapid, accurate, and cost-efficient detection is required.

The description of the invention is divided into: I. Forms of Biopolymeric Materials; II. Self-Assembling Monomers; III. Dopants; IV. Ligands; V. Detection of Colorimetric Changes; VI. Detection of Membrane Conformational Changes; VII. Immobilization of Biopolymeric Materials; and VIII. Arrays. The biopolymeric materials described in these sections can be designed to detect the presence of analytes (e.g., pathogens, chemicals, nucleic acids, and proteins) and can be designed to detect membrane rearrangements (e.g., lipid cleavage events and modification of nucleic acids). In some embodiments, it may be desired to have biopolymeric materials that accomplish both of these functions. The optimization of the biopolymeric materials (e.g., optimization of colorimetric response, color, and stability) with regards to the detection of analytes or membrane rearrangements is often generally applicable to both scenarios. Where there are differences, it is noted.

I. FORMS OF BIOPOLYMERIC MATERIALS

The biopolymeric material of the presently invention can take many physical forms including, but not limited to, liposomes, films, and multilayers, as well as braided, lamellar, helical, tubular, and fiber-like shapes, and combinations thereof. In some embodiments, the biopolymeric materials are solvated polymers in aggregate forms such as rods and coils. Each of these classes is described below, highlighting their advantages and the difficulties overcome during the development of these materials.

A. Films

In some embodiments, the biopolymeric material used in the present invention comprise biopolymeric film. As described in Example 1, biopolymeric films were prepared by layering the desired matrix-forming material (e.g., self-assembling organic monomers) onto a formation support. In preferred embodiments, the formation support was a standard Langmuir-Blodgett trough and the matrix-forming material was layered onto an aqueous surface created by filling the trough with an aqueous solution. The material was then compressed and polymerized to form a biopolymeric film. In preferred embodiments, the compression was conducted in a standard Langmuir-Blodgett trough using moveable barriers to compress the matrix-forming material. Compression was carried out until a tight-packed monolayer of the matrix-forming material was formed. Films provide a very sensitive calorimetric screen for analytes.

As described in Example 1, in some embodiments, the matrix-forming material, located within the formation support, was polymerized by ultra-violet irradiation. However, all methods of polymerization are contemplated by the present invention and include, but are not limited to, gamma irradiation, x-ray irradiation, chemical crosslinking, and electron beam exposure.

In some embodiments, lipids comprising diacetylene monomers (DA) were used as the self-assembling monomer. The diacetylene monomers (DA) were polymerized to polydiacetylene (p-PDA or PDA) using ultraviolet irradiation. In preferred embodiments, the ultraviolet radiation source is kept sufficiently far from the film to avoid causing heat damage to the film. The crystalline morphology of the polymerized film can be readily observed between crossed polarizers in an optical microscope, although this step is not required by the present invention. The conjugated backbone of alternating double and triple bonds (i.e., ene-yne) that was generated following polymerization, gave rise to intense absorptions in the visible spectrum and led to a distinct blue/purple appearance of the polymerized diacetylene film.

In certain embodiments the visibly blue films were then transferred to hydrophobized solid supports, such that the carboxylic acid head groups were exposed at the film-ambient interface (Charych et al., Science 261: 585 [1993]) to undergo further analysis, although the method of the present invention does not require this step. Linear striations typical of PDA films can be observed in the polarizing optical microscope. The material may also be characterized using atomic force microscopy or other characterization means (See e.g., Example 2).

The present invention contemplates all other means of making films, as several other methods are known in the art. For example, films can be made by solvent casing (i.e., slow evaporation of the solvent). Also, lipid monomers can be made with silane or thiol anchoring groups, which allows dipping of solid supports into the solution to form a coated solid support. In one embodiment of the present invention, diacetylene monomers are anchored by the silane and thiol groups and are then polymerized. This method eliminates the need for a trough.

B. Liposomes

In other embodiments, the biopolymeric material used in the present invention comprises biopolymeric liposomes. Liposomes were prepared using a probe sonication method (New, *Liposomes: A Practical Approach*, Oxford University Press, Oxford, pp 33–104 [1990]), although any method that generates liposomes is contemplated by the present invention. Self-assembling monomers, either alone, or associated with a desired ligand, were dried to remove the formation solvents and resuspended in deionized water. The suspension was probe sonicated and polymerized. The resulting liposome solution contained biopolymeric liposomes.

Figure 2B:
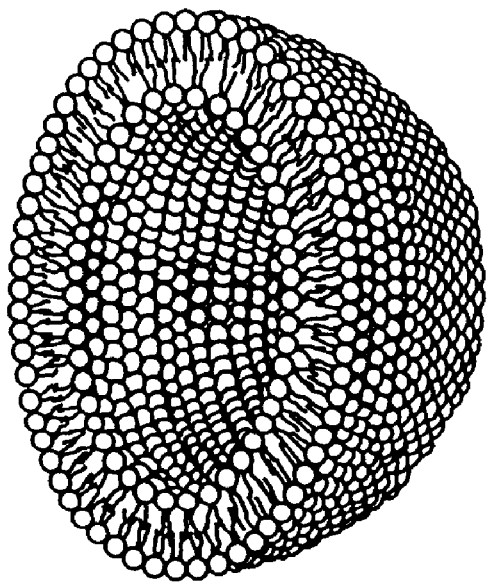
FIG. 2 shows a schematic representation of biopolymeric liposomes. Part A is a cross-section two-dimensional view and part B is a three-dimensional view of half of a liposome.
Figure 2A:
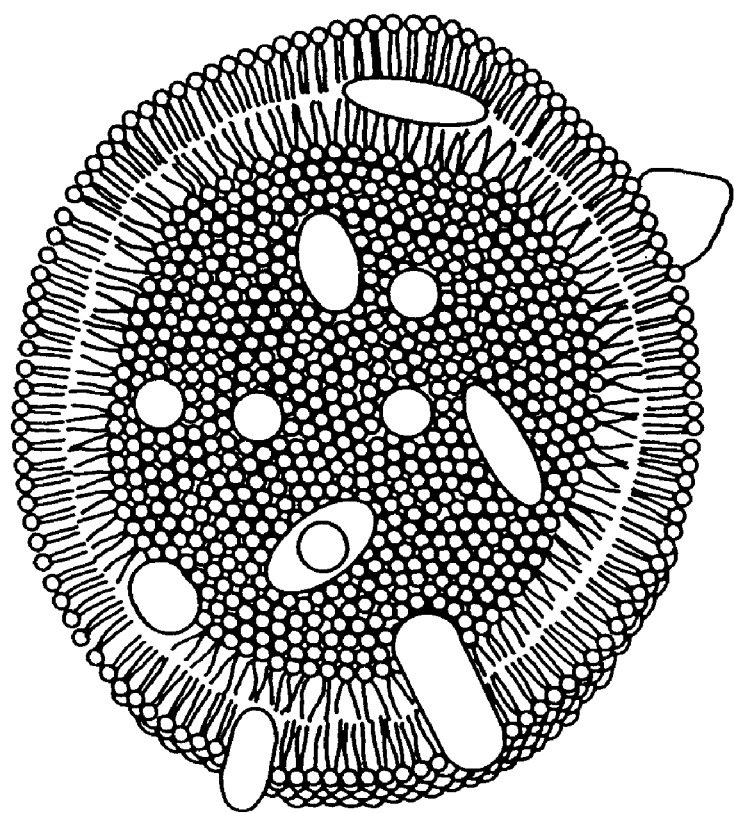

Liposomes differ from monolayers and films in both their physical characteristics and in the methods required to generate them. Monolayers and films (or multilayers) made from amphiphilic compounds are planar membranes and form a two-dimensional architecture. Monolayers and films, in this context, are solid state materials that are supported by an underlying solid substrate as shown in FIG. 1. Film Y is a centrosymmetric multilayer film, while films X and Z are noncentrosymmetric multilayers. Such materials are described in numerous articles and have been reviewed in text such as Ulman (Ulman, *An Introduction to Ultrathin Organic Films: From Langmuir-Blodgett to Self-Assembly*, Academic Press, Inc., Boston, [1991]) and Gaines (Gaines, *Insoluble Monolayers at Liquid-Gas Interfaces*, Interscience Publishers, New York, [1966]). In contrast to films and monolayers, liposomes are three-dimensional vesicles that enclose an aqueous space as shown in FIG. 2. FIG. 2 shows A) a cross-section two-dimensional view; and B) a three-dimensional view of half of a liposome. These materials are described in numerous articles and have been reviewed in texts such as New (New, *Liposomes: A Practical Approach*, IRL Press, Oxford, [1989]), and Rosoff (Rosoff, *Vesicles*, Marcel Dekker, Inc., New York, [1996]) among others. Liposomes can be constructed so that they entrap materials within their aqueous compartments. Films and monolayers do not enclose an aqueous space and do not entrap materials within a compartment. The liposomes are typically more stable and robust than the films made of the same material.

Liposomes and films are prepared using different methods. Liposomes are prepared by dispersal of amphiphilic molecules in an aqueous media and remain in the liquid phase. In contrast, monolayers and films are prepared by immobilizing amphiphilic molecules at the air-water interface. A solid support is then passed through the interface to transfer the film to the solid support. Liposomes exist within homogenous aqueous suspensions and may be created in a variety of shapes such as spheres, ellipsoids, squares, rectangles, and tubules. Thus, the surface of a liposome is in contact with liquid only—primarily water. In some respects, liposomes resemble the three-dimensional architecture of natural cell membranes. If liposomes are dried to their solid state, they may lose their shape and no longer exist in a liposomal state (i.e., are no longer "liposomes"). In contrast, films exist as planar heterogeneous coatings, immobilized onto a solid support. The surface of a monolayer or film can be in contact with air, other gases, or other liquids. Films can be dried in air and maintain their planar monolayer or multilayer structure and thus remain as "films."

Figure 3A:
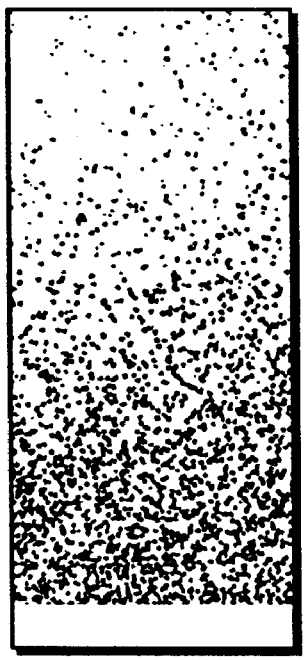
FIG. 3 shows biopolymeric 1) liposomes and 2) films comprising the same biopolymeric material and exposed to the same analyte.
Figure 3B:
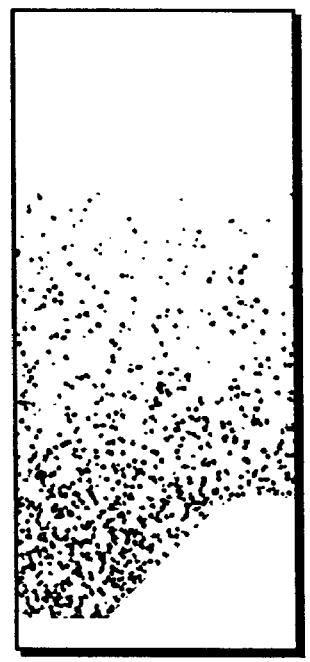

A much higher concentration of polymerized material can be achieved with liposome solutions compared to monolayer assemblies, due to their greater cross-sectional density. Liposomes have the advantage, generally, of making the color change more visually striking and increasing the colorimetric response (See e.g. FIG. 3 showing the calorimetric response of immobilized sialic-acid-containing liposomes (1) and films (2) to the presence of influenza virus).

In designing methods to generate the liposomes of the present invention, several difficulties had to be overcome. While it was initially hoped that liposomes could be generated with the self-assembling monomer material (e.g. diacetylenes) used in various film embodiments (i.e., film embodiments of the present invention discussed above and in Example 1), it was not known whether this would be possible, largely due to the differences in liposomal and film architecture. Liposomes are three-dimensional instead of two-dimensional. Therefore, it was not clear whether 1) the diacetylenic lipids would actually form liposomes at all; 2) whether they would polymerize if they were capable or forming liposomes; and/or 3) whether they would exhibit colorimetric properties even if they could be polymerized.

Regarding the first point, it was not clear that the single-chained diacetylenic lipids would actually form liposomes. This is because the majority of the literature shows that single chain molecules tend to form micelles (i.e., loosely packed single-bilayer suspensions), whereas only double chain molecules can form liposomes. Furthermore, as described by New (New, supra), the double chain molecules typically used in liposome formation are derived from natural cell membranes and usually have a classical phospholipid structure incorporating such molecular components as phosphodiglycerides and sphingolipids, unlike the diacetylenic lipids of the present invention.

Figure 4:
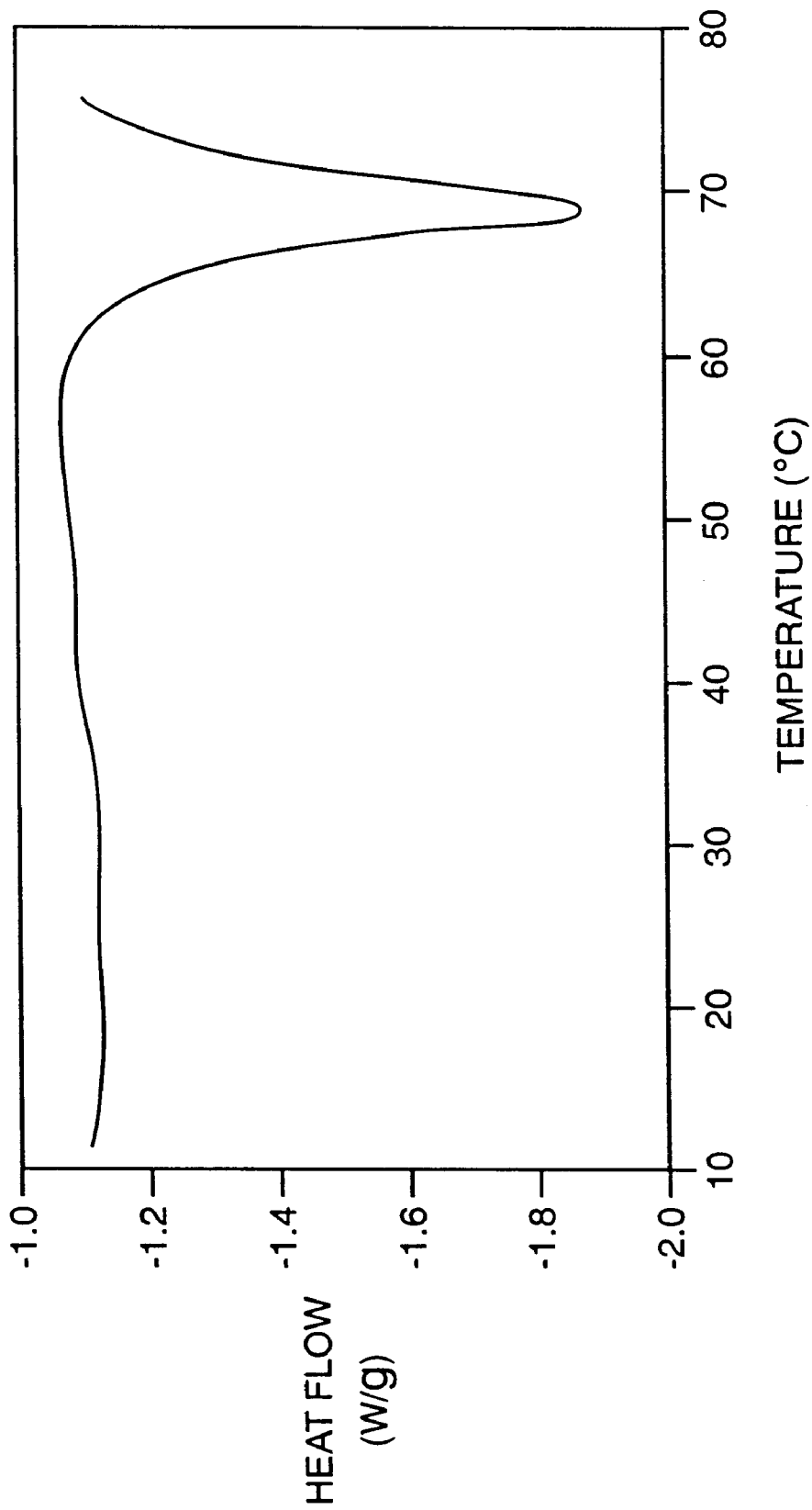
FIG. 4 shows a heating curve depicting the large main phase transition for unpolymerized liposomes prepared from PDA monomer.

Initially, attempts to form liposomes with diacetylenic lipids using standard methods such as vortexing or bath sonications were tried (i.e., methods that are similar to those commonly applied to phospholipids). These methods failed to form liposomes and resulted in the formation of an insoluble, non-dispersed, non-characterizable mixture. This mixture did not exhibit colorimetric properties. Applying differential scanning calorimetry, it was determined that the $T_m$ (main phase transition temperature) of the lipids was much higher than their natural phospholipid counterparts. For example, FIG. 4 shows a heating curve depicting the large main phase transition for unpolymerized liposomes prepared from lysine-derivated PDA monomer. Therefore, it was necessary to employ higher energy methods such as ultrasonic probe sonication and beating, to raise the temperature above $T_m$ and to disperse the lipid. Under these conditions (e.g., as described in Example 1) liposomes were formed, as evidenced by light scattering and transmission electron microscopy with a size in accordance with a liposome (i.e., approximately 100 nm).

Figure 5:
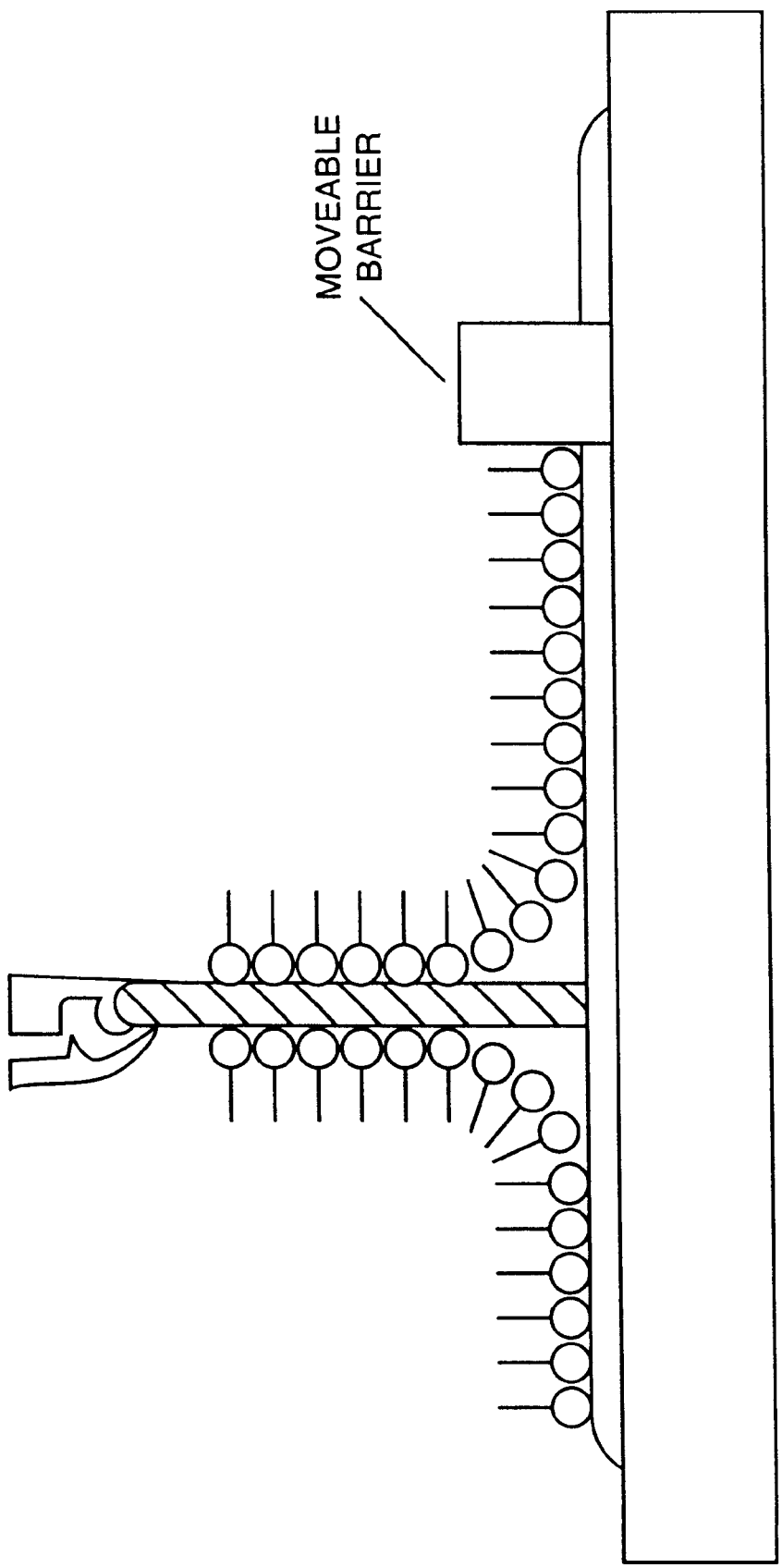
FIG. 5 shows a schematic representation of a Langmuir Blodgett apparatus where a compressed film is being transferred to a vertical plate.

Regarding the second point, polymerization requires that the lipids pack in a precise distance and orientation with respect to one another. The polymerization of polydiacetylene is therefore a "solid state" or topochemical polymerization. This is why the molecules must be closely packed to allow cross-linking. This precise packing can be controlled in monolayer and films at the air-water interface using moveable barriers of Langmuir apparatus that can compress the film to the desired packing as shown in FIG. 5, in which a compressed film is being transferred to a vertical plate. In the case of liposome formation, no such external compression is possible. The lipids assemble and occupy an equilibrium distance and orientation with respect to one another. Therefore, prior to the development of the present invention, it was not clear that the distance and packing between the molecules in the liposome material would be sufficient to allow the polymerization reaction to take place.

Figure 6:
FIG. 6 shows a micrograph of liposomes cooled only to room temperature.
Figure 7:
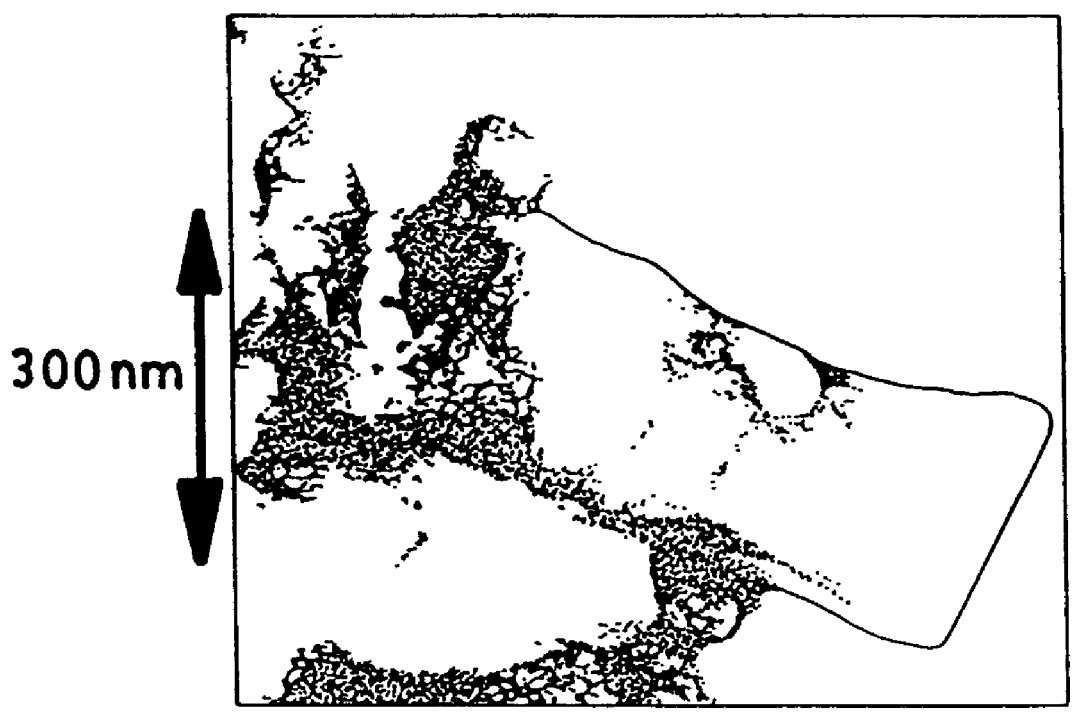
FIG. 7 shows a micrograph of liposomes prepared with cooling to 4° C.

Initially, the most difficult aspect was cross-linking the liposome diacetylenic monomeric lipids, to generate a polydiacetylene conjugated polymer (i.e., polymerized liposomes). It is the conjugated polymer backbone that provides the liposomes with the desired color, and potentially allows the detection of biological analytes through an observable color change produced by the binding of the analyte to the liposomes. However, after the liposomes were formed (i.e., using the methods described above) and cooled to room temperature, it was found that they did not polymerize at all upon exposure to ultraviolet light. This was surprising because, in principle, the lipids should have crystallized and returned to their solid-like state when cooled to room temperature (i.e., once the lipids returned to this state, they should have undergone the topochemical polymerization as described above). However, they did not, as apparently the lipids were still fluid. Further analysis by transmission electron microscopy (TEM) proved that the liposomes were not crystallized. These room temperature liposomes aggregated into larger globules, characteristic of non-stabilized fluid phase liposomes as shown in the micrograph of FIG. 6. Based upon these observations, it was hypothesized that there was a hysteresis effect in the heating/cooling curve of these materials. This proved to be correct, leading to the development of "supercooling" methods. For Example, in these methods, the liposomes were cooled to 4° C., resulting in the successful crystallization of the lipids. After the cooling step was carried out, it was found that the liposomes could be polymerized, even when raised back to room temperature. Polymerization was evidenced by the blue color of the material, and the absorbance at approximately 630 nm. In contrast to the liposomes that were not supercooled, these liposomes crystallized into squares, rectangles, ellipses, or spheres that maintained their structure indefinitely, as shown in the micrograph of FIG. 7.

All of the above experimentation for production of suitable liposomes for various embodiments of the present invention (i.e., experimentation described above), is in direct contrast to the methods used to produce films. Films can be formed and polymerized at the same (i.e., ambient) temperature.

Regarding the third point, even with the polymerized liposomes, prior to the development of the present invention, it was not known whether they would exhibit color changes in response disruption of the biopolymeric membrane. For instance, it was not known whether the different lipid packing architecture of liposomes would permit the color changes observed with the film embodiments. It was only through further experimentation that optimal liposomes were developed for colorimetric detection of analytes.

C. Other Forms

In other embodiments, it is contemplated that variations in the heating and cooling rates, agitation methods, and materials of the biopolymeric material will provide other nanostructures. Such nanostructures include, but are not limited to, multilayers, braided, lamellar, helical, tubular, and fiber-like shapes, and combinations thereof. Such structures can, in some embodiments, be solvated polymers in aggregate forms such as rods and coils. For example, it has been shown that the chain length of the monomers effects the type of aggregate that forms in solution (Okahata and Kunitake, J. Am. Chem. Soc. 101: 5231 [1979]). Generation of these other forms with surfactant materials has been described for double chains (Kuo et al., Macromolecule 23: 3225 [1990]), lamellae (Rhodes et al., Langmuir 10: 267 [1994]), hollow tubules and braids (Frankel et al., J. Am. Chem. Soc. 116 [1994]). In some embodiments, colorimetric tubules were generated. As described in Example 1, tubules were prepared similarly to liposome, except that 1–10% of an organic solvent (e.g., ethanol) was added to the solution prior to sonication. The present invention also contemplates other shapes suitable for particular uses as desired.

Figure 39:
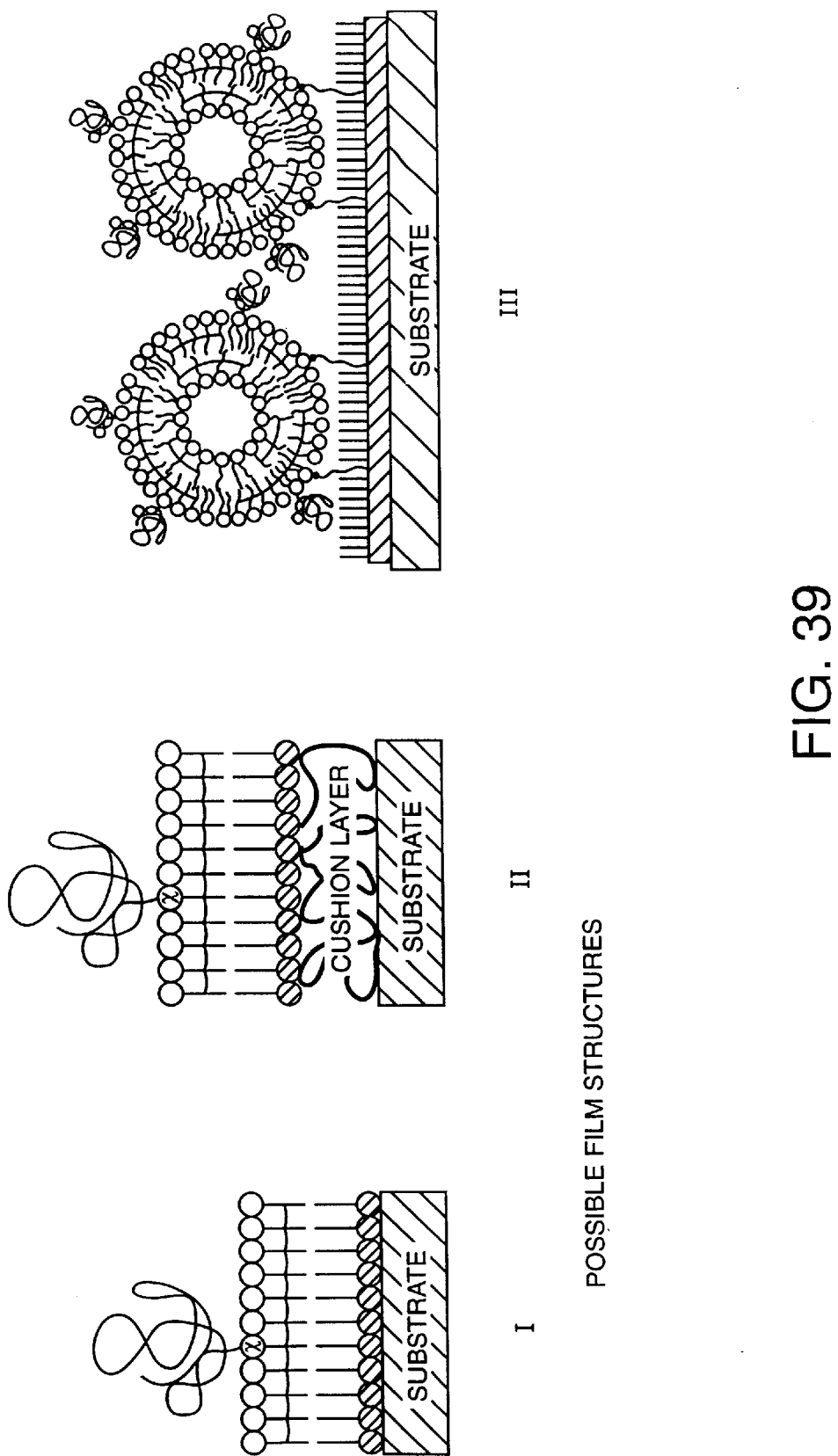
FIG. 39 shows several embodiments of biopolymeric assemblies.

Other bilayer systems of polydiacetylene lipids can be prepared to serve as colorimetric detectors. Such structures include molecular double layers on solid supports created by LB, Langmuir-Schaefer transfer, or by adsorption and unrolling of monomeric liposomes, followed by photopolymerization (FIG. 39[I]). A related system is the tethered supported bilayer (FIG. 39[II]) with a 'cushion' layer sandwiched between the substrate surface and the bilayer. This 'cushion' layer decouples the flexible bilayer from the immobile solid support and allows, for example, incorporation of membrane proteins. A third structural variation is the covalent fixation of polymeric liposomes at planar surfaces of self-assembled monolayers (FIG. 39[III]).

In other embodiments, soluble polymers of polythiophenes are generated. In some embodiments, sugar groups, peptides, or other ligands can be synthesized as thiophene derivatives and then polymerized as co-polymers. Alternately, NHS derivatives of thiophene can be polymerized and ligand groups can be attached after the polymer has formed (described below). The thiophene polymers are rendered water soluble by the addition of acid groups. Thus they are synthesized to freely dissolve in aqueous solution, creating a calorimetric solution.

II. SELF-ASSEMBLING MONOMERS

In certain embodiments, the present invention contemplates a variety of self-assembling monomers that are suitable for formation of biopolymeric materials. Such monomers include, but are not limited to, acetylenes, diacetylenes (e.g. 5,7-docosadiynoic acid, 5,7-pentacosadiynoic acid, and 10,12-pentacosadiynoic acid), alkenes, thiophenes, polythiophenes, imides, acrylamides, methacrylates, vinylether, malic anhydride, urethanes, allylamines, siloxanes, poly-silanes, anilines, pyrroles, polyacetylenes, poly (para-phylenevinylene), poly (para-phylene), and vinylpyridinium. Lipids containing these groups can be homopolymers or mixed polymers. Furthermore, monomers with a variety of head groups are contemplated, including, but not limited to carboxylic acid, hydroxyl groups, primary amine functionalities, amino acid derivatives, and hydrophobic groups. Certain head groups may act as recognition sites for binding to analytes, allowing direct colorimetric detection, simply through exposure of the biopolymeric material to the analyte.

The biopolymeric material of the present invention may comprise a single species of self-assembling monomer (e.g., may be made entirely of 5,7-pentacosadiynoic acid) or may comprise two or more species. To produce biopolymeric material with more than one type of self-assembling monomer, solvents containing the individual monomers are combined in the desired molar ratio. This mixture is then prepared as described above (e.g., layering onto the aqueous surface of a Langmuir-Blodgett device for film preparation or evaporated and resuspended in aqueous solution for liposome preparation). In some embodiments the self-assembling monomers may be chemically linked to another molecule (e.g. a ligand).

In preferred embodiments, lipid monomers comprising diacetylene were used as the self-assembling monomers of the biopolymeric material of the present invention. The present invention contemplates a variety of diacetylene-containing lipids including, but not limited to 5,7-docosadiynoic acid (5,7-DCDA), 5,7-pentacosadiynoic acid (5,7-PCA), and 10,12-pentacosadiynoic acid (10,12-PCA).

Figure 8:
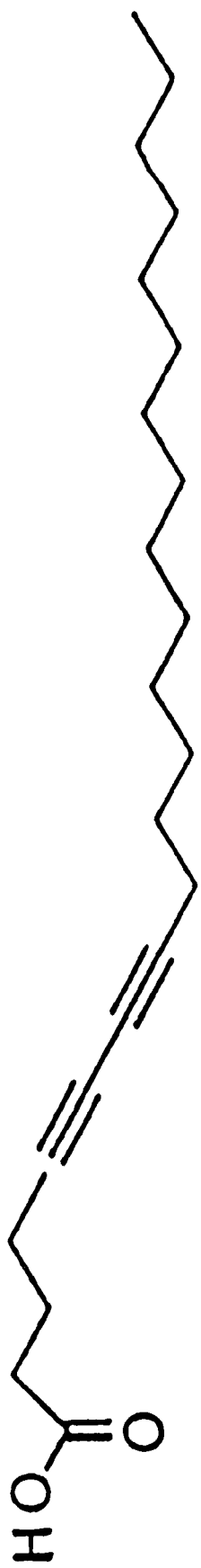
FIG. 8 shows the chemical structure of 5,7-pentacosadiynoic acid.

The present invention further contemplates the optimization of the biopolymeric material to maximize response to given reaction conditions. Although it is not necessary to understand the mechanism in order to use the present invention, and it is not intended that the present invention be so limited, it is contemplated that the chemistry of the particular lipid used in the biopolymeric material plays a critical role in increasing or decreasing the sensitivity of the calorimetric transition. For example, a positional variation of the chromophoric polymer backbone can alter sensitivity to a given analyte. This may be accomplished by moving the diacetylene group closer to the interfacial region as illustrated in FIG. 8, showing 5,7-pentacosadiynoic acid (as opposed to 10,12-pentacosadiynoic acid). Altering the placement of the polymerizable group to the 5,7 position in the monomer, dramatically improved calorimetric sensitivity in some embodiments (See e.g., Example 3). In addition, shorter or longer chain lengths of PDA were shown to have an effect on the sensitivity of the biopolymeric material for analyte detection, presumably due to changes in packing. In some analyte-detecting embodiments, such improved sensitivity allowed detection of small analytes (e.g., bacterial toxins such as cholera toxin from *Vibrio cholerae* and pertussis toxin, as well as antibodies). It is contemplated that further optimization will generate sensitive materials for the detection of many reactions, rearrangements, and analytes.

A. Polymerizable Group Placement in Monomer Carbon Chain

The carbon chain length that positions the head group a specific distance from the polymer backbone in the final polymerized material is dependent on the position of the polymerizable group in an unassembled monomer. In the case of diacetylene liposomes, some embodiments of the present invention demonstrated that a diacetylene group positioned from between the 18–20 positions to the 3–5 position in the monomers produced progressively more sensitive liposomes when used for the detection of analytes. Liposomes produced from monomers with the diacetylene groups from the 10–12 position to the 4–6 position provided particularly efficient control of sensitivity. Diacetylene groups positioned in about the 5–7 position are preferred for certain embodiments, such as cholera toxin detection. The production protocol for the monomer determines at which position the diacetylene group is placed in the final monomer product.

B. Total Carbon Chain Length

Experiments conducted during the development of the present invention demonstrated that the total carbon chain length in the unassembled monomer also influenced the level of sensitivity of the liposome product, although to a lesser extent than the position of the polymerizable group in the monomer carbon chain. The shorter chain length typically provided for greater sensitivity for, as determined in analyte-detecting embodiments. The monomers that are ideally useful in construction of the inventive colorimetric liposomes range from between $C_{12}$ to $C_{25}$ in length, although both longer and shorter chain lengths are contemplated by the present invention. A preferred range of monomer carbon chain length in the present invention is $C_{20}$ to $C_{23}$.

The influence of monomer chain lengths and positioning of the polymerizable group on the chain has been demonstrated in several experiments. It was shown that in the case of 10,12-diacetylene derivative, $C_{23}$ chains provided a final colorimetric liposomes product that changed color at a lower analyte level than those produced from monomers with a $C_{25}$ chain. In the case of 5,7-diacetylene derivatives, the $C_{22}$ length chain provided a greater sensitivity than the $C_{24}$ length chain. Thus, the chain length is designed so as to be suitable for the optimal detection conditions of interest, in view of other desired characterisitcs of the biopolymeric materials (e.g. stability).

III. DOPANTS

The biopolymeric materials of the present invention may further comprise one or more dopant materials. Dopants are included to alter and optimize desire properties of the biopolymeric materials. Such properties include, but are not limited to, colorimetric response, color, sensitivity, durability, robustness, amenability to immobilization, temperature sensitivity, and pH sensitivity. Dopant materials include, but are not limited to, lipids, cholesterols, steroids, ergosterols, polyethylene glycols, proteins, peptides, or any other molecule (e.g., surfactants, polysorbate, octoxynol, sodium dodecyl sulfate, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cerebroside, lysophosphatidylcholine, D-erythroshingosine, sphingomyelin, dodecyl phosphocholine, N-biotinyl phosphatidylethanolamine, and other synthetic or natural components of cell membranes) that is associated with a membrane (e.g., liposomes and films). For example, the embodiments provided in Example 4 demonstrate that the addition of sialic acid-derived diacetylene monomers to liposomes comprising ganglioside and PDA provided a dramatic increase in colorimetric sensitivity and quantifiability to the detection of low levels of analyte. This improvement in colorimetric response using dopant is extremely beneficial when un-doped materials produce only weak signals. Such is often the case when the target lipids (e.g., lipids that contain the ligand or that are the substrate of an enzymatic reaction) are not covalently linked to the polymer backbone (e.g., ganglioside ligands).

In some embodiments, dopants are added to alter the color of the biopolymeric material. For example, the present invention provides liposomes that change from blue to red, but also blue to orange, purple to red, purple to orange, green to red, and green to orange. For example, glutamine-derivatized PDA produced very dark blue (i.e., almost black) liposomes. In other embodiments, green liposomes were produced with cycles of annealing (i.e., heating to approximately 80° C.) and cooling (i.e., to ambient temperatures) prior to polymerization. The advantage with the multi-color approach is that sensors can be made where a specific reaction turns the material a specific color.

In other embodiments, different dopant materials are combined in a single biopolymeric material preparation. For example, the present invention provides a dopant cocktail that is a mix of glucose and sialic acid-derived polydiacetylene. The glucose component of the dopant mixture appears to act primarily to prevent non-specific adhesion to the surface of the inventive liposome and may also enhance sensitivity. The polydiacetylene bound sialic acid component appears to functionally destabilize the surface to provide a dramatic increase in sensitivity for analyte detection. By using this co-dopant approach, both specificity of adhesion and sensitivity can be optimized, without unduly compromising the structural integrity of the biopolymeric material.

Although it is not necessary to understand the mechanism in order to use the present invention, and it is not intended that the present invention be so limited, it is contemplated that the addition of dopant lowers the activation barrier of the chromatic transition and/or provides a connection between the ligands (i.e., if ligands are present) and the conjugated backbone, enabling the reactions to induce the colorimetric transition. One theory elucidated during the development of the present invention is that dopants with bulky headgroups (e.g., sialic acid-derived lipid monomers) are subject to various solvent interactions at the matrix surface, destabilizing the structure of the blue film and thus allowing relatively small perturbations provided by the localized membrane rearrangements to complete the colorimetric transition. Another possible explanation for the improved colorimetric response observed using dopants with bulky headgroups is that the stearic effects induced by the molecular recognition event (i.e., the interaction of an analyte or other molecule with the biopolymeric material) may interfere with the headgroups of the dopants, thus propagating the perturbation caused by the analyte.

In certain embodiments, the dopant comprises a diacetylene or a modified diacetylene (e.g., sialic acid derived diacetylene). It should be noted that in this case, the derivatized lipid is used to modify the properties of the biopolymeric material and is not used as a molecular recognition site for an analyte detection (e.g., as in the case of sialic acid ligand used to detect influenza virus). For example, a diacetylene-based polymeric material containing only sialic acid derivatized monomer or lactose derivatized monomer did not respond to neurotoxins (e.g., botulinum neurotoxin), indicating that there was an insufficient interaction between the neurotoxins and the derivatized diacetylene lipid to induce the color change. However, when the same material was provided with a ligand having affinity for neurotoxin (e.g., ganglioside $G_{M1}$), a calorimetric response was detected in the presence of neurotoxin. In this example, the sialic acid and lactose derived lipids are "dopants" and the ganglioside $G_{M1}$ is a ligand.

It is contemplated that a wide variety of dopant materials will find use in optimizing the properties of the biopolymeric material used in various embodiments of the present invention. Materials that are constituents of cell membrane structures in nature are generally useful as dopants in the present invention. For instance, steroids (e.g., cholesterols) represent potential dopants that can provide desired degrees of destabilization or stabilization to the biopolymeric material. Surfactant type compounds also may serve as dopants, whether or not they are polymerized to self-assembling monomers that make up the polymer back bone. For example, the detergent TWEEN 20, which does not contain a polymerizable group, has been shown to provide a very dramatic intensity to the blue color of the liposomes of certain embodiments of the present invention. An alternative surfactant that can be used as dopants are peptide-detergents (i.e., small amphipathic molecules that have a hydrophobic region mimicking the membrane spanning regions of membrane proteins). These small peptides (typically 20–25 amino acids in length) can be incorporated into the biopolymeric material to alter the stability or sensitivity of the colorimetric response of the material. Since peptide-detergents are bulkier in the hydrophobic region of the material, they are capable of producing a more pronounced effect on film stability or sensitivity than many other surfactant molecules.

The most appropriate percentage of dopant incorporated into the structure of the biopolymeric material is dependent on the particular system being developed, and the needs of the testing situation. For instance, sensitivity may be compromised to some extent in the favor of long shelf life, or to accommodate rigorous field conditions. The acceptable percentage of dopant is theoretically limited only to that which will not preclude sufficient incorporation of the indicator polydiacetylene molecules to produce the necessary optical density and color change or to that which will disrupt the stability of the polymeric structures.

Molar percentages of dopant can vary from as low as 0.01% where increases of sensitivity have been observed in certain embodiments, to as high as 75%, after which the structural integrity of the biopolymeric material typically begins to deteriorate. However, there may be specific embodiments where the percentage of dopant is greater than 75% or lower than 0.01%. A preferred range for dopant is 2%–10%. In certain embodiments of the present invention, the optimal percentage of dopant is about 5% (See e.g., Example 4, section II). For example, for the detection of cholera toxin, it was found that a film comprising 2% lactose-derivatized polydiacetylene (PDA), 5% ganglioside, and 93% PDA resulted in a strong blue to red color change when the film was incubated with the analyte.

In selecting appropriate incorporation methods for the dopant, there are several competing considerations. For example, for the sonication bath method for production of certain liposome embodiments, the incorporation is very controlled, and requires several hours of processing. This relatively slow, gentle incorporation method allows the incorporation of comparatively large or complex dopant materials. However, the sonication bath approach is only suitable when it is intended that a relatively low percentage of dopant is to be incorporated. The point probe method allows the incorporation of a much higher percentage of dopant material over a shorter period of time, typically from one to ten minutes. However, this method is typically limited to incorporation of small to intermediate sized dopant materials. The temperature chosen for incorporation are selected based on the particular analytical system and liposome parameters desired. A practitioner will be able to select parameters such as pH, choice of dilutents, and other factors based on the particular system and desired characteristics of the biopolymeric material.

A series of derivatized polydiacetylene dopant molecules have been synthesized with a wide range of physical characteristics. These dopants are not the same as filler molecules typically observed in biological membranes (i.e., cholesterol, proteins, lipids, detergents). They differ in that they provide unique and specific functionality to a given sensor system. The design of several dopants that provide specific functionality to the non-synthetic embodiments are described below and in Example 4.

A simple system has been designed so that the PDA molecule can easily be derivatized. The synthesis is shown in FIG. 9. Here, 10,12-pentacosadiynoic acid is modified to amine-couple to any molecule with a free amino group. Since all amino acids have a free amino group (lysine has 2 free amino groups), the 20 amino acids were each placed on the head of PDA molecules. Each one of the derivatized PDA molecules has special properties that allow special functionality to be incorporated into the biopolymeric material. For example, glutamine-PDA doped materials were the most sensitive, most water soluble, and most consistent calorimetric sensors. The properties of some of the other amino acid-derivated PDA molecules are described in Example 4. The water solubility, ability to form films and liposomes, color, and colorimetric response for representative amino acid-derived diacetylenes is shown respectively in FIGS. 10A and 10B.

IV. LIGANDS

The biopolymeric materials of the present invention may further comprise one or more ligands. Ligands act as a recognition site in the biopolymeric materials for analytes or as anchors for recruiting molecules or localizing reactions to the biopolymeric surface. In some embodiments, upon the interaction of the analyte with the ligand or ligands, a disruption of the polymer backbone of the biopolymeric material occurs, resulting in a detectable color transition.

In some embodiments, ligands are linked by a linking arm to the self-assembling monomers, directly linked to the monomers, incorporated into the biopolymeric matrix prior to or during the polymerization process, or attached to the matrix following polymerization (e.g., by linking ligands to matrix constituents that contain head groups that bind to the ligands or through other means). For example, FIG. 11 provides a schematic depiction of one embodiment of the present invention. Compound 1 shows a receptor-binding ligand (i.e., sialic acid) attached to one terminal end of a spacer molecule. The second terminal end of the spacer molecule is attached to one of several monomers (e.g., 10,12-pentacosadiynoic acid) that have been polymerized so as to form a chromatic detection element. Compound 2 shows the 10,12-pentacosadiynoic acid without an attached ligand.

The ligand group of the present invention comprise a wide variety of materials. The main criterion is that the ligand have an affinity for the analyte of choice. Appropriate ligands include, but are not limited to, peptides, carbohydrates, nucleic acids, biotin, drugs, chromophores, antigens, chelating compounds, short peptides, pepstatin, Diels-Alder reagents, molecular recognition complexes, ionic groups, polymerizable groups, dinitrophenols, linker groups, electron donor or acceptor groups, hydrophobic groups, hydrophilic groups, antibodies, or any organic molecules that bind to receptors. The biopolymeric material can be composed of combinations of ligand-linked and unlinked monomers to optimize the desired colorimetric response (e.g. 5% ligand-linked dicosadynoic acid [DCDA] and 95% DCDA). Additionally, multiple ligands can be incorporated into a single biopolymeric matrix. As is clear from the broad range of ligands that can be used with the present invention, an extremely diverse group of analytes can be detected.

In some embodiments, the self-assembling monomers are not associated with ligands, but are directly assembled, polymerized, and used as colorimetric sensors. Such biopolymeric materials find use in the detection of certain classes of analytes including, but not limited to, volatile organic compounds (VOCs).

In some embodiments, ligands are incorporated to detect a variety of pathogenic organisms including, but not limited to, sialic acid to detect HIV (Wies et al., Nature 333: 426 [1988]), influenza (White et al., Cell 56: 725 [1989]), Chlamydia (Infect. Imm. 57: 2378 [1989]), *Neisseria meningitidis, Streptococcus suis*, Salmonella, mumps, newcastle, and various viruses, including reovirus, Sendai virus, and myxovirus; and 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); β-adrenergic receptor to detect reovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpes virus (Kaner et al., Science 248: 1410 [1990]); oligomannose to detect *Escherichia coli*; ganglioside $G_{M1}$ to detect *Neisseria meningitidis*; and antibodies to detect a broad variety of pathogens (e.g., *Neisseria gonorrhoeae, V. vulnificus, V. parahaemolyticus, V. cholerae*, and *V. alginolyticus*).

One skilled in the art will be able to associate a wide variety of ligand types with the biopolymeric materials of the present invention. Methods of derivatizing lipids with a diverse range of compounds (e.g., carbohydrates, proteins, nucleic acids, and other chemical groups) are well known in the art. The carboxylic acid on the terminal end of lipids can be easily modified to form esters, phosphate esters, amino groups, ammoniums, hydrazines, polyethylene oxides, amides, and many other compounds. These chemical groups provide linking groups for carbohydrates, proteins, nucleic acids, and other chemical groups (e.g., carboxylic acids can be directly linked to proteins by making the activated ester, followed by reaction to free amine groups on a protein to form an amide linkage). Examples of antibodies attached to Langmuir films are known in the art (See e.g., Tronin et al., Langmuir 11: 385 [1995]; and Vikhohn et al., Langmuir 12: 3276 [1996]). There are numerous other means to couple materials to membranes, or incorporate materials within a membrane, including for example, coupling of proteins or nucleic acids to polymer membranes (See e.g., Bamford et al. Adv. Mat. 6: 550 [1994]); coupling of proteins to self-assembled organic monolayers (See e.g., Willner et al., Adv. Mat. 5: 912 [1993]), and incorporating proteins into membranes (See e.g., Downer et al., Biosensor and Bioelect. 7: 429 [1992]); among others. Protocols for attaching ligands (e.g. proteins, nucleic acids, and carbohydrates) to the colorimetric materials of the present invention are demonstrated in Example 5.

For example, the methods of the present invention provide a system to easily attach protein molecules, including antibodies, to the surface of polydiacetylene thin films and liposomes, thereby providing biopolymeric materials with "protein" ligands. Such ligands include, but are not limited to, peptides, proteins, lipoproteins, glycoproteins, enzymes, receptors, channels, and antibodies. Upon binding an analyte (e.g., enzyme substrate, receptor ligand, antigen, and other protein), a disruption of the polymer backbone of the biopolymeric material may occur, resulting in a detectable color change. The present invention contemplates protein ligands that are incorporated into the biopolymeric material and those chemically associated with the surface of the biopolymeric material (e.g., chemically linked to the surface head group of a monomer in the biopolymeric monomer).

A. Nucleic Acid Ligands (i) Selection of Nucleic Acid Ligands

One characteristic property of nucleic acids is their ability to form sequence-specific hydrogen bonds with a nucleic acid having a complementary sequence of nucleotides. This ability of nucleic acids to form sequence-specific hydrogen bonds (i.e., to hybridize) with complementary strands of nucleic acids is exploited in the methods of the present invention. Nucleic acid having a known sequence (nucleic acid ligand) or desired hybridization characteristics is used as a "probe" to search a sample for a "target" complementary sequence. Target sequences are identified employing various nucleic acid ligands and the compositions and methods of the present invention.

The target sequence, to which the probe region is complementary, can be any whole or portion of genomic material, or nucleic acid gene product such as ribosomal, transfer, messenger or intron RNA, from any organism (including, but not limited to bacteria, viruses, parasites, and fungi) or cells (e.g., any eukaryotic or prokaryotic cells, including but not limited to cultured cells). Target sequences are typically in the order of several hundred nucleotides, although shorter and longer sequences are contemplated by the present invention. They can be, for example and without limitation, sequences characteristic of a human or non-human pathogen (which includes any infectious microorganism), human or non-human (e.g. animal) DNA or RNA sequences (e.g., sequences characteristic of a genetic abnormality or other condition), and sequences derived from genetic engineering experiments such as, for example, total mRNA or random fragments of whole cell DNA. Methods for identifying target sequences and for preparing probe regions are well known in the art. The target sequence can also be, for example, complementary to a nucleic acid sequence characteristic of a class of human or non-human pathogens, for example, all enteric bacilli or all Chlamydia. The target sequence can also be, for example, complementary to a nucleic acid sequence characteristic of a host cell or vector used in the manufacture of recombinant DNA products (e.g., to detect the presence of such DNA or RNA contaminants in the product). In this regard, nucleic acids which are complementary to (i.e., have affinity for) various target sequences identified above are contemplated as the nucleic acid ligands of the present invention.

Another type of nucleic acid ligand contemplated by the present invention, include nucleic acid molecules which bind to, or interact with, other biological molecules (e.g., enzymes such as polymerases, nucleases, ligases, telomerases, and transcription factors). This type of binding depends upon the nucleotide sequence(s) that comprise the DNA or RNA involved. For example, short DNA sequences are known to bind to target proteins that repress or activate transcription in both prokaryotes and eukaryotes. Other short DNA sequences are known to serve as centromeres and telomeres of chromosomes, presumably by creating ligands for the binding of specific proteins that participate in chromosome mechanics. In this regard, nucleic acid molecules with sequences that are natural targets of biological molecules are contemplated as the nucleic acid ligands of the present invention.

The present invention also contemplates nucleic acid ligands that are not the natural targets for biological molecules, but which are instead capable of binding to any desired analyte selected by the user. One technique used to identify such nucleic acids is called the SELEX procedure. The basic SELEX procedure is described in U.S. Pat. Nos. 5,475,096; 5,270,163; and 5,475,096; and in PCT publications WO 97/38134, WO 98/33941, and WO 99/07724, all of which are herein incorporated by reference. The SELEX procedure allows identification of nucleic acid molecules with unique sequences, each of which has the property of binding specifically to a desired target analyte or molecule.

Briefly, the SELEX procedure involves selection from a mixture of candidates of interest in step-wise iterations. The SELEX procedure starts with a mixture of nucleic acids, preferably comprising a segment of randomized sequence. The mixture is contacted with a target (e.g., an analyte) under conditions favorable for binding. Next, unbound nucleic acids are partitioned from those nucleic acids which have bound to target molecules. Then, the nucleic acid-target pairs are dissociated and the nucleic acid is either amplified or isolated to yield a preparation enriched for target binding. The steps of binding, partitioning, dissociating and amplifying may be reiterated through as many cycles as desired.

Nucleic acids that have the highest affinity constants for the target are most likely to bind. After partitioning, dissociation and amplification, a second nucleic acid mixture is generated that is enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/ amplification is continued until no significant improvement in binding strength is achieved upon repetition of the cycle. The method may be used to sample as many as about $10^{18}$ different nucleic acid species in a test mixture. The nucleic acids of the test mixture preferably include a randomized sequence portion, as this portion provides a large number of possible sequences and structures with a wide range of binding affinities for a given target. A nucleic acid mixture comprising, for example a 20 nucleotide randomized segment can have $4^{20}$ candidate possibilities. However, the present invention is not limited to a randomized segment of any particular length. In some embodiments, the randomized portion may be from about 40 to 120 base pairs in length, while in other embodiments, the randomized portion may be from about 50 to 100 base pairs in length, and in some preferred embodiments, the randomized portion is from about 70 to 90 base pairs in length.

The randomized portion is flanked by 5' and 3' fixed sequence regions. The fixed sequence regions are conserved sequences useful for efficient amplification (e.g., by PCR). Accordingly, the same pair of PCR primers can be utilized to amplify the randomized regions selected by the protocol. In some preferred embodiments, the fixed sequence regions are designed so that dimer formation and annealing between primers is minimized. In other preferred embodiments, the fixed regions include a promoter region (e.g., T3, T7, or SP6 promoter). In still other embodiments, the 5' fixed sequence region and 3' fixed sequence region are flanked by restriction sites to allow easy cloning of the entire nucleic acid including the fixed regions, or subcloning of the randomized region. Useful restriction sites include, but are not limited to, sites known in the art such as EcoRi, HindIII, PstI, etc.

Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations. Partitioning methods used in SELEX rely on a partitioning matrix. High affinity oligonucleotides may be separated using various methods, including chromatographic-type processes, binding to nitrocellulose filters, liquid-liquid partition, gel filtration, and density gradient centrifugation.

Accordingly, the present invention contemplates screening a randomized pool of nucleic acid molecules for the ability to bind to various analytes, in order to use these nucleic acid molecules as nucleic acid ligands in the present invention. In some embodiments, a composition comprising nucleic acids is provided. In some embodiments, the mixture comprises greater than about $10^{12}$ different nucleic acid sequences, while in particularly preferred embodiments, the mixture comprises greater than about $10^{18}$ different nucleic acid sequences. In preferred embodiments of the present invention, the nucleic acids include a randomized portion. In other embodiments, the randomized portion is from about 30 to 150 nucleotides in length. In still other embodiments, the randomized portion is from about 40 to 120 nucleotides in length. In other preferred embodiments, the randomized portion is from about 50 to 100 nucleotides in length. In some particularly preferred embodiments, the randomized portion is from about 70 to 95 nucleotides in length, while in other particularly preferred embodiments, the randomized portion is from about 50 to 60 nucleotides in length.

Therefore, the present invention comtemplates nucleic acid ligands capable of binding to many types of analytes.

Further examples of these these analytes include, but are not limited to, pathogens, drugs, receptor ligands, antigens, ions, proteins, hormones, blood components, antibodies, and lectins.

All of the various nucleic acid ligands identified above may also be included as a domain or portion of a larger nucleic acid molecule. Also, all of the nucleic acid ligands identified above can be conjugated to monomers as described below.

(ii) Attachment of DNA to Monomers

In one embodiment of the present invention, self-assembling monomers were covalently attached to the 5'-terminus of a single stranded DNA fragment, also referred to as oligodeoxynucleotide (ODN). The ODN-lipid conjugate was incorporated into diacetylene liposome assemblies. A common procedure for conjugation reactions with synthetic DNA is the modification of an oligodeoxynucleotide (ODN) in a DNA synthesizer with an amino function at the 5'-end and cleaving and deprotecting the ODN to give a reactive amine functionality capable of further reactions (See e.g., Chatterjee et al., J. Am. Chem. Soc. 112:6397–6399 [1990]; Gryaznov et al., Nucleic Acids Res. 21 [1993]; Reed et al., Bioconjugate Chem. 6:101–108 [1995]; Soukup et al., Bioconjugate Chem. 6:135–138 [1995]; Herrlein et al., J. Am. Chem. Soc. 117:10151–10152 [1995]; Timofeev et al., Nucleic Acids Res. 24:3142–3148 [1996]; Kang et al., Nucleic Acids Res. 24:3896–3902 [1996]; and Ganachaud et al., Langmuir 13:701–707 [1997]). Amidation with an activated carboxylate (i.e., N-hydroxysuccinimide ester) is usually employed. In one embodiment, a 5'-amino functionalized 27-mer (hereinafter, "Oligo 1"), $H_2N—CH_2—CH(CH_2OH)—OPO_2H—O—^{5'}GAATGTATTAGAATGTAATGAACTTTA^{3'}$) (SEQ ID NO:1), was conjugated with the N-hydroxysuccinimide ester of 10,12-pentacosadiynoic acid (NHS-PDA).

An alternative procedure for conjugation was the N,N'-dicyclohexylcarbodiimide (DCC) mediated esterification of a diacetylene lipid monophosphate. The method of phosphate diester formation by reaction of a phosphate monoester with an alcohol in the presence of dicyclohexylcarbodiimide has been described by Khorana et al., with pyrophosphates being formed as side products (See e.g., Khorana et al., J. Chem. Soc. [1953]; Smith et al., J. Am. Chem. Soc. 80:6204–6212 [1958]; Gilham et al., J. Am. Chem. Soc. 80:6212–6222 [1958]; and Tener et al., J. Am. Chem. Soc. 80 [1958]). The reaction of a sugar phosphate with a lipid alcohol has been reported using dicyclohexylcarbodiimide as condensation reagent (See e.g., Warren et al., Biochemistry 11:2565–2572 [1972]; Warren et al., Biochemistry 12:5031–5037 [1973]; and Warren et al., Biochemistry 12:5038–5045 [1973]). The obtained conjugation products were characterized by gel electrophoresis as single strands and as hybridization products with their unmodified complements. DNA incorporation into liposomes using bacteriophage λ to inject DNA into liposomes carrying the Shigella receptor has also been reported (New et al., Liposomes: A Practical Approach, first Ed., Oxford University Press:New York [1990]). In one embodiment of the present invention, the 5'-OH terminus of a solid support bound 10-mer was conjugated with a diacetylene monophosphate using DCC.

In certain embodiments of the present invention, the ODN-lipid conjugates were mixed with liposomes which were then photopolymerized and filtered to remove unbound ODN. The amount of ODN retained with the liposomes was quantified by UV absorbance measurements at 260 nm. Interaction and inclusion of DNA in liposomes have been investigated, particularly as DNA delivery systems in gene therapy (See e.g., New et al., supra). Cationic liposomes form layered complexes with parallel aligned DNA helixes sandwiched between lipid bilayers, exhibiting a liquid crystalline behavior (See e.g., Radler et al., J. Am. Chem. Soc. 275:810–814 [1997]; and Lasic et al., J. Am. Chem. Soc. 119:832–833 [1997]) Unlike the present invention, however, none of these liposomes exhibit visible calorimetric changes upon binding to DNA.

In certain embodiments, the adsorption characteristics of ODN onto cationically charged latex particles were investigated in dependence of pH. Coulomb interaction between the positively charged surface and the negatively charged ODN, and hydrophobic interactions or H-bonding play an important role (See e.g., Ganachaud et al., Langmuir 13:701–707 [1997]; and Elaissari et al., Langmuir 11:1261–1267 [1995]). This hydrophobic interaction/H-bonding causes ODN to adsorb even on negatively charged surfaces, as was observed in PDA liposomes with exposed carboxylic acid headgroups at the liposome surface.

It is not intended that the present invention be limited to any particular methods of DNA-lipid incorporation. In one embodiment, single stranded probe DNA (ss-p-DNA) lipids are incorporated into preformed biopolymeric material with subsequent photopolymerization. This method requires synthesis of ss-p-DNA lipids, conjugation of the probe DNA with a diacetylene lipid, and subsequent insertion in the layer, followed by polymerization of the diacetylenes. The direct conjugation of the diacetylene lipid to the 5'-end of the probe DNA could, for example, be achieved by treatment of the 5'-OH-terminated oligonucleotide with $POCl_3/PO(OCH_3)_3$ and the lipid alcohol, or by phosphorylation of the 5'-OH-end with cyanoethyl phosphateltrichloroacetonitrile, followed by reaction with the lipid alcohol/trichloroacetonitrile. This method however, gives a rather low yield. (See e.g., Ringsdorf et al., Angew. Chem. 100:117 [1988]; and Chen et al., J. Colloid Interface Sci. 153:244 [1992]). An alternative synthetic procedure that gives higher yields involves the coupling of phosphoramidite or the H-phosphonate of the lipid as the last coupling step in the automated oligonucleotide synthesis (See e.g., Kunitake, Angew. Chem. 104:692 [1992]; Roberts, *Langmuir-Blodgett Films*, Plenum Press, New York [1990]; and Ulman, *Ultrathin Organic Films*, first ed., Academic Press, Inc., San Diego [1991]). This method requires that the lipid be stable against the reaction conditions in the DNA synthesizer. Since oxidation of the intermediate phosphite triester to the phosphate is accomplished by $I_2$ treatment, the diacetylene unit might not be stable under these conditions, and addition of iodine to the triple bond might occur. Functional groups may also be introduced at the 5'-end, like an amino or thiol moiety, followed by the coupling of the lipid. A variety of phosphoramidites with such functional groups are commercially available for use in the DNA synthesizer.

Alternatively, ss-p-DNA could be linked to specific anchor lipids after photopolymerizaiton of the lipids, in order to circumvent photodegradation of the DNA. Furthermore, liposomes are immobilized covalently to a substrate surface for integration into calorimetric detection devices. This attachment can be achieved by incorporation of an anchor lipid which reacts specifically with functional groups exposed on the substrate surface. DNA fixation at polydiacetylene surfaces can be achieved by unspecific immobilization at amino or Al(III) phosphonate functionalized surfaces, or photocoupling of DNA to silica gel-bound psoralen. In the case of the amino- and Al(III) phosphonate, surface specific hybridization of complementary DNA to the surface bound DNA was reported (See e.g., Zasadzinski et al., Science 263:1726 [1994]; Whitesides et al., Science 254:1312 [1991]; and Damer et al., *Liposome Preparation: Methods and Mechanisms*, first ed., Marcel Dekker, Inc., New York and Basel [1983]).

In one embodiment of the present invention, the DNA ligands provided a 30% colorimetric response to a hybridization event by complementary nucleic acid. The response was sequence-specific, as noncomplementary control oligonucleotides provided only 15% response.

V. DETECTION OF COLORIMETRIC CHANGES

The colorimetric change resulting from disruption of the biopolymeric material can be detected using many methods. In preferred embodiments of the present invention, a color shift was observed simply by visual observation. Thus, the present invention may be easily used by an untrained observer such as an at-home user.

In alternative embodiments, spectral test equipment well known in the art is employed to detect changes in spectral qualities beyond the limits of simple visual observation, including optical density to a particular illuminating light wavelength. For example, using a spectrometer, the spectrum of the material was measured before and after analyte introduction, and the colorimetric response (% CR) was measured. The visible absorption spectrum of the material prior to analyte exposure was measured as $B_o=I_x/(I_y+I_x)$ where "B" represents the percentage of a given color phase at wavelength $I_x$ compared to a reference wavelength $I_y$. The spectrum was then taken following analyte exposure and a similar calculation was made to determine the $B_{final}$. The colorimetric response was calculated as % CR=$[(B_o-B_{final})/B_o]\times 100\%$.

Additionally, the present invention can be, if desired, attached to a transducer device. The association of self-assembled monomer materials with transducers has been described using optical fibers (See e.g., Beswick and Pitt, J. Colloid Interface Sci. 124: 146 [1988]; and Zhao and Reichert, Langmuir 8: 2785 [1992]), quartz oscillators (See e.g., Furuki and Pu, Thin Solid Films 210: 471 [1992]; and Kepley et al., Anal. Chem. 64: 3191 [1992]), and electrode surfaces (See e.g., Miyasaka et al., Chem. Lett., p. 627 [1990]; and Bilewicz and Majda, Langmuir 7: 2794 [1991]). However, unlike these examples, the present invention provides a double-check (i.e., confirmation method) by observation of color change in the material.

In some embodiments, the biopolymeric materials of the present invention can be coated on thin PzT materials that oscillate at a resonance frequency, producing a microelectromechanical system (MEMS system). Thus, alterations in the biopolymeric material can be detected as a change in resonant frequency with calorimetric change providing a confirmation of event.

Sensitivity can also be enhanced by coupling the lipid-polymer to a photoelectric device, colorimeter, or fiber optic tip that can read at two or more specific wavelengths. Also, the device can be linked to an alternative signalling device such as a sounding alarm or vibration to provide simple interpretation of the signal.

As described above, in addition to detecting the activity of analytes (e.g., lipid cleavage activity of lipases and membrane modification activity of transferases), it may also be desired to detect the presence of analytes. The biopolymeric materials of the present invention can be used to detect a large variety of analytes including, but not limited to, small molecules, microorganisms, membrane receptors, membrane fragments, volatile organic compounds (VOCs), enzymes, drugs, antibodies, and other relevant materials by the observation of color changes that occur upon analyte binding. The present invention works under very mild testing conditions, providing the ability to detect small biomolecules in a near natural state and avoiding the risks associated with modification or degradation of the analyte.

VI. DETECTION OF MEMBRANE CONFORMATIONAL CHANGES

As described above, the present invention provides methods for detecting conformational alterations in the biopolymeric material by observation of calorimetric changes. Such conformational changes can be caused by the binding of an analyte to a ligand (described above) and through the chemical modification of the biopolymeric material by chemical reactions (e.g., enzymatic catalysis).

In some embodiments, the present invention provides a simple protocol using biopolymeric material and offers a practical approach to detecting interfacial catalysis, identifying inhibitors, and screening enzymes and other catalytic entities (e.g., catalytic antibodies) to characterize their catalytic capabilities. These methods use natural, unlabeled substrates, and catalysis or inhibition is signaled by the presence or lack of a color transition of the surrounding lipid-polymer assembly. The one-step nature of the technique allows for convenient adaptation to high throughput compound screening. This method is generally applicable to factors that affect enzyme recognition and activity, and influence membrane reorganization.

Polymerized mixed vesicles are highly stable against chemical and physical degradation and offer a convenient, economical alternative to enzymatic assays that employ radiolabled substrates. The vesicle stock solutions described by the present invention have been stored for over six months without affecting the results of the assay.

Specific applications of the present invention are described below to illustrate the broad applicability of the invention to a range of conformational changes and to demonstrate its specificity, and ease of use. Phospholipase $A_2$, phospholipase C, phospholipase D, bungarotoxin, and other enzyme activities are illustrated. These examples are intended to merely illustrate the broad applicability of the present invention; it is not intended that the present invention be limited to these particular embodiments.

A. Phospholipase $A_2$ Activity $PLA_2$ activity has previously been studied in a variety of model membrane systems such as polymerized vesicles (Dua et al., J. Biol. Chem. 270, 263 [1995]), micelles (Reynolds et al. supra), and monolayers (Grainger et al., supra; and Mirsky et al., Thin Solid Films 284, 939 [1996]) using labeling techniques (e.g., radioactivity and fluorescence). The present invention provides biopolymeric materials incorporating $PLA_2$ substrate lipids for the calorimetric detection of $PLA_2$ enzyme activity.

Figure 12A:
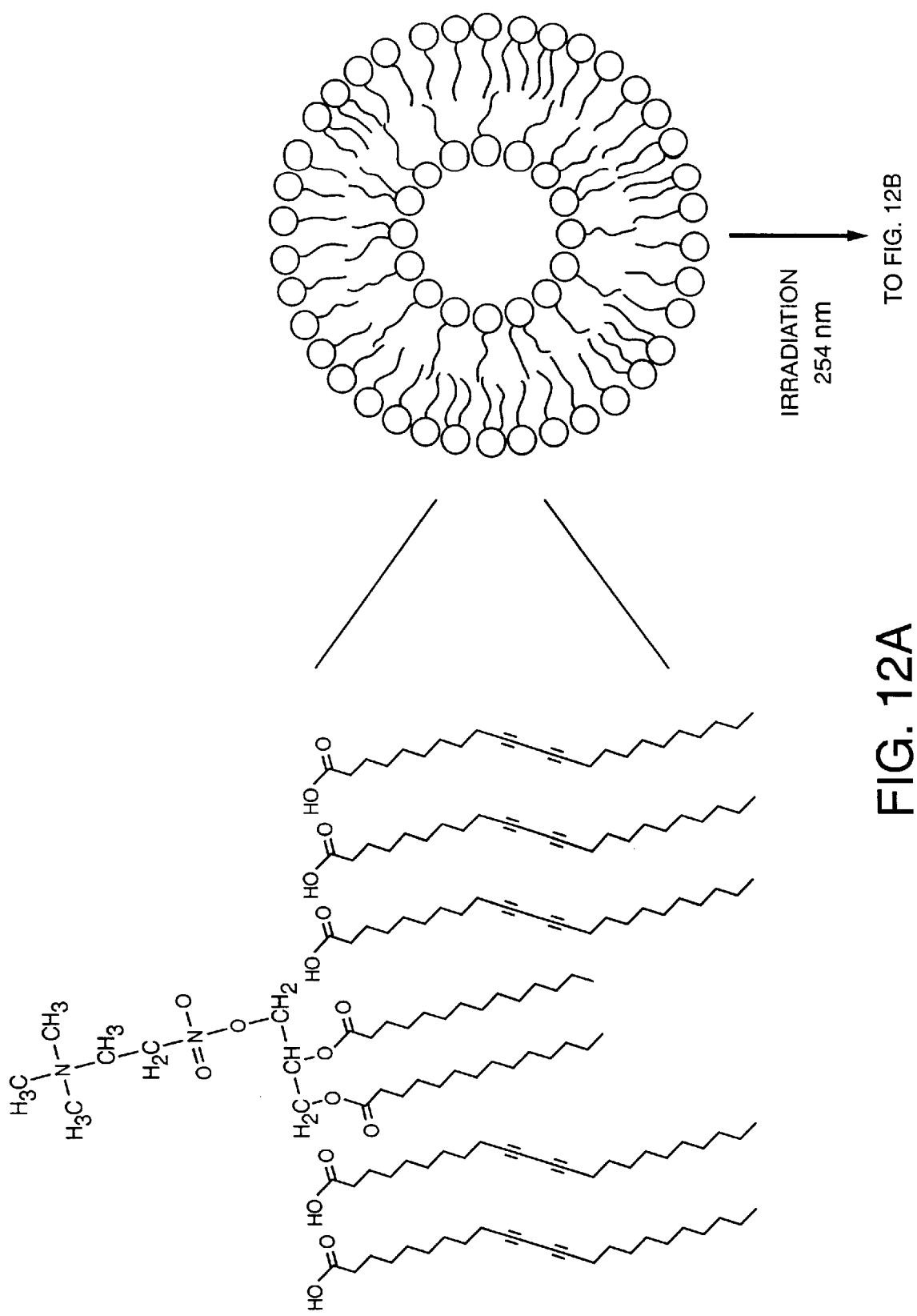
FIG. 12 shows substrate lipid (i.e., DMPC) in a diacetylenic lipid matrix before (top) and after (bottom) polymerization.
Figure 12B:
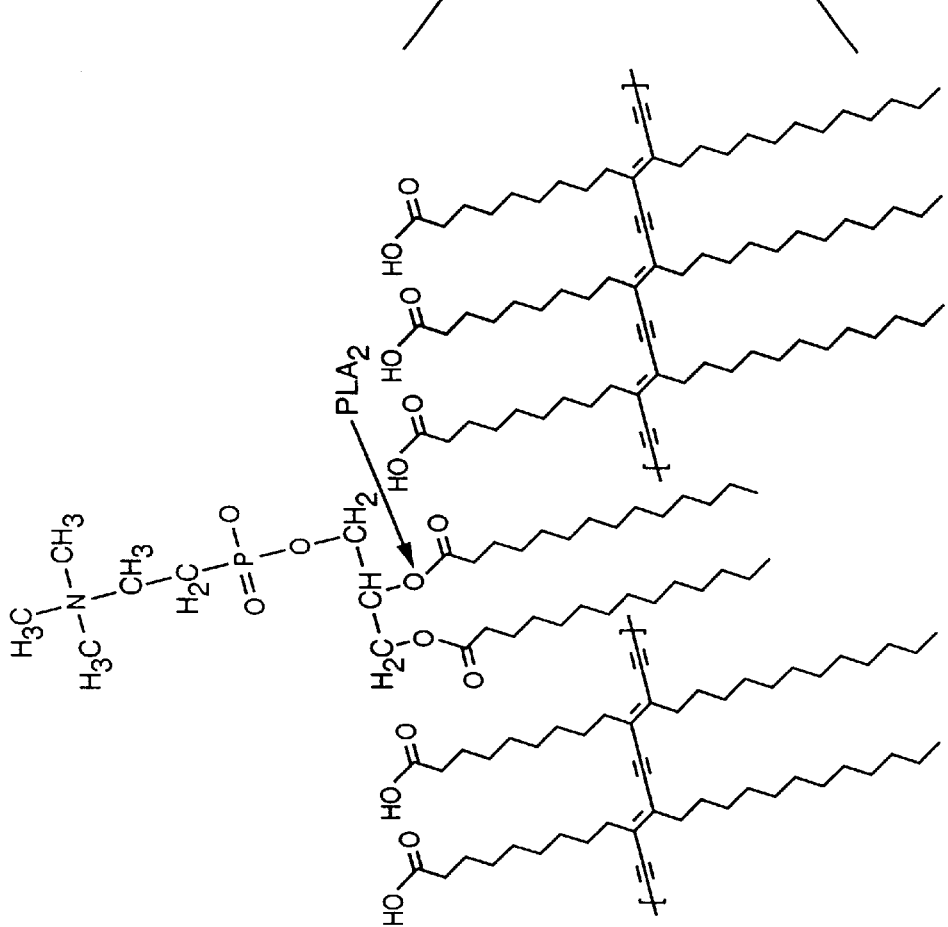
Figure 13:
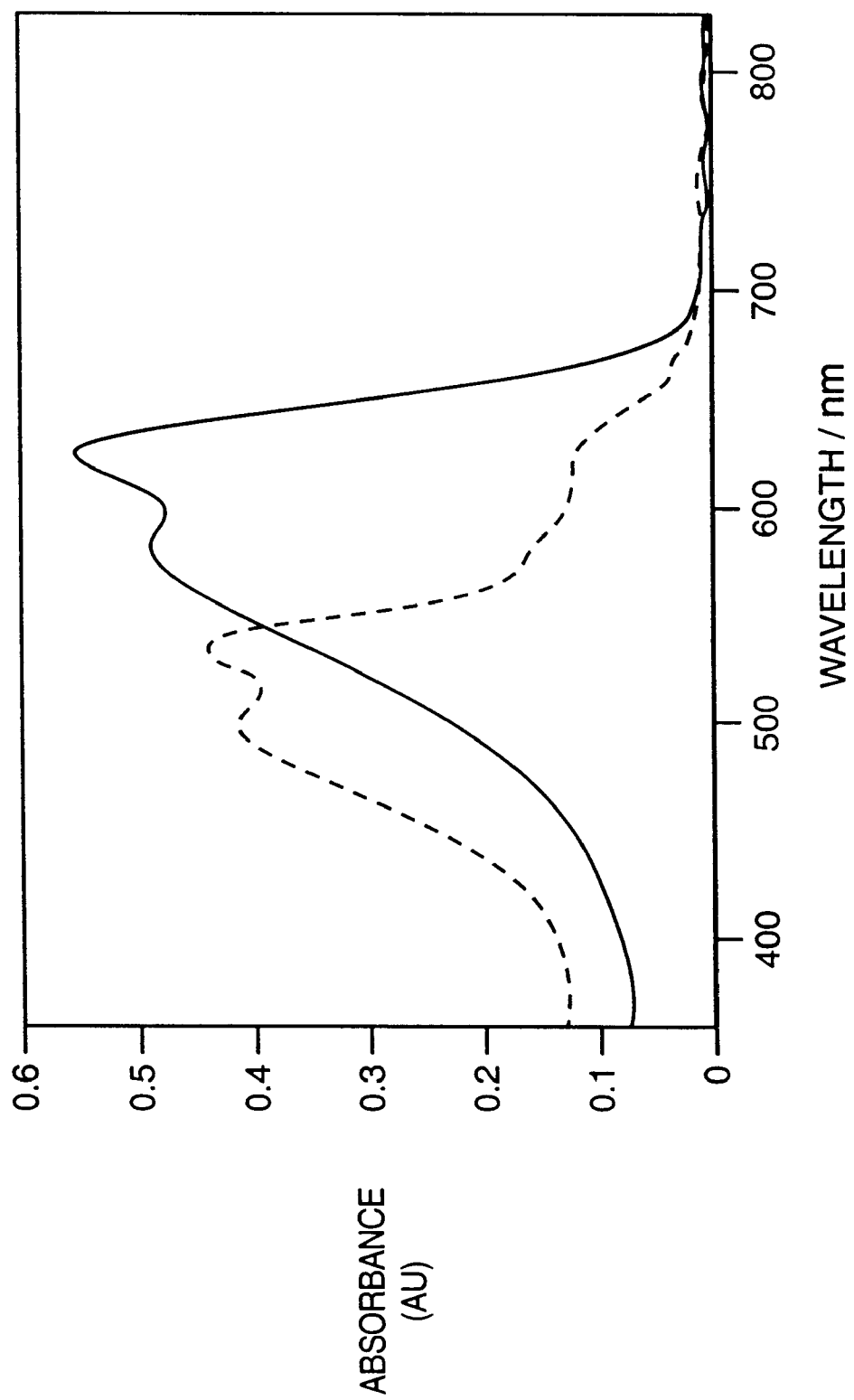
FIG. 13 shows the visible absorption spectrum of the liposomes of FIG. 12 before (solid line) and after (dashed line) exposure to phospholipase $A_2$.

Biopolymeric materials were prepared with a combination of polymerizable matrix lipid (e.g., 10,12-tricosadiynoic acid) and various mole fractions (0–40%) of $PLA_2$ substrate lipid (e.g., dimyristoylphosphatidylcholine [DMPC]) as described in Examples 1 and 10. In some embodiments, the biopolymeric materials containing the $PLA_2$ substrate lipid were liposomes as shown in FIG. 12. This figure shows DMPC substrate in a diacetylenic lipid matrix before (top) and after (bottom) polymerization. In their initial state, the vesicles appeared deep blue to the naked eye and absorbed maximally at around 620 nm, as shown in FIG. 13 (solid line). Upon addition of $PLA_2$ to the DMPC/PDA vesicles, the suspension rapidly turned red (i.e., within minutes) and exhibited a maximum absorption at approximately 540 nm as shown in FIG. 13 (dashed line).

Figure 14:
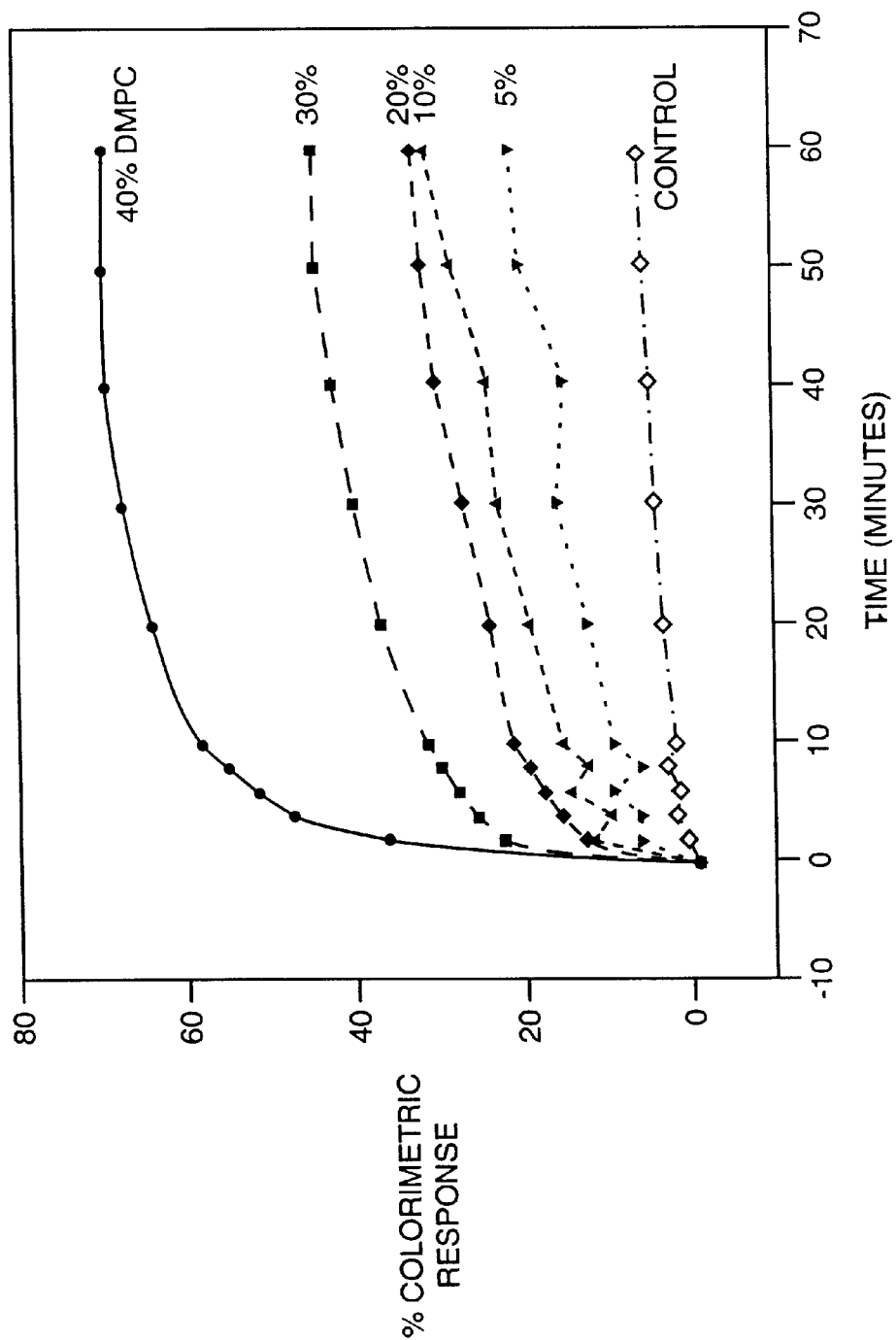
FIG. 14 shows the change in calorimetric response of the liposomes of FIG. 12 with varying concentrations of DMPC in response to phospholipase $A_2$ exposure.

The color change was modulated by altering the mole percentage of the natural lipid DMPC in the PDA vesicle as shown in FIG. 14. A relative color change of 10% or more is clearly observed with the naked eye. Within minutes, liposomes containing greater than 20% DMPC exhibited strong colorimetric responses. Liposomes with low molar ratios of DMPC (e.g., 5%) also showed visually detectable colorimetric response after longer incubations. Vesicles that did not contain DMPC, remained largely in their blue phase upon addition of $PLA_2$ as shown in the control sample.

Biochromic transitions of PDA vesicles and films have been proposed to arise from perturbation of the extended $\pi$-overlap of the conjugated polymer backbone. This structural rearrangement, induced in previous studies by multivalent receptor binding or penetration of peptide domains into the PDA matrix, results in absorption at shorter wavelengths, (i.e., 490–540 nm) (Charych et al., Chemistry and Biology, supra; Pan and Charych, supra; and Cheng and Stevens, Advance Materials, supra). The intense color change observed upon the interaction between the enzyme $PLA_2$ and the mixed DMPC/PDA vesicles indicates, that in this case, chemical modification of the vesicles by interfacial catalysis provides an alternative pathway for inducing the biochromatic transitions. Thus, the present invention demonstrates a new means of inducing colorimetric change in biopolymeric materials.

Figure 15:
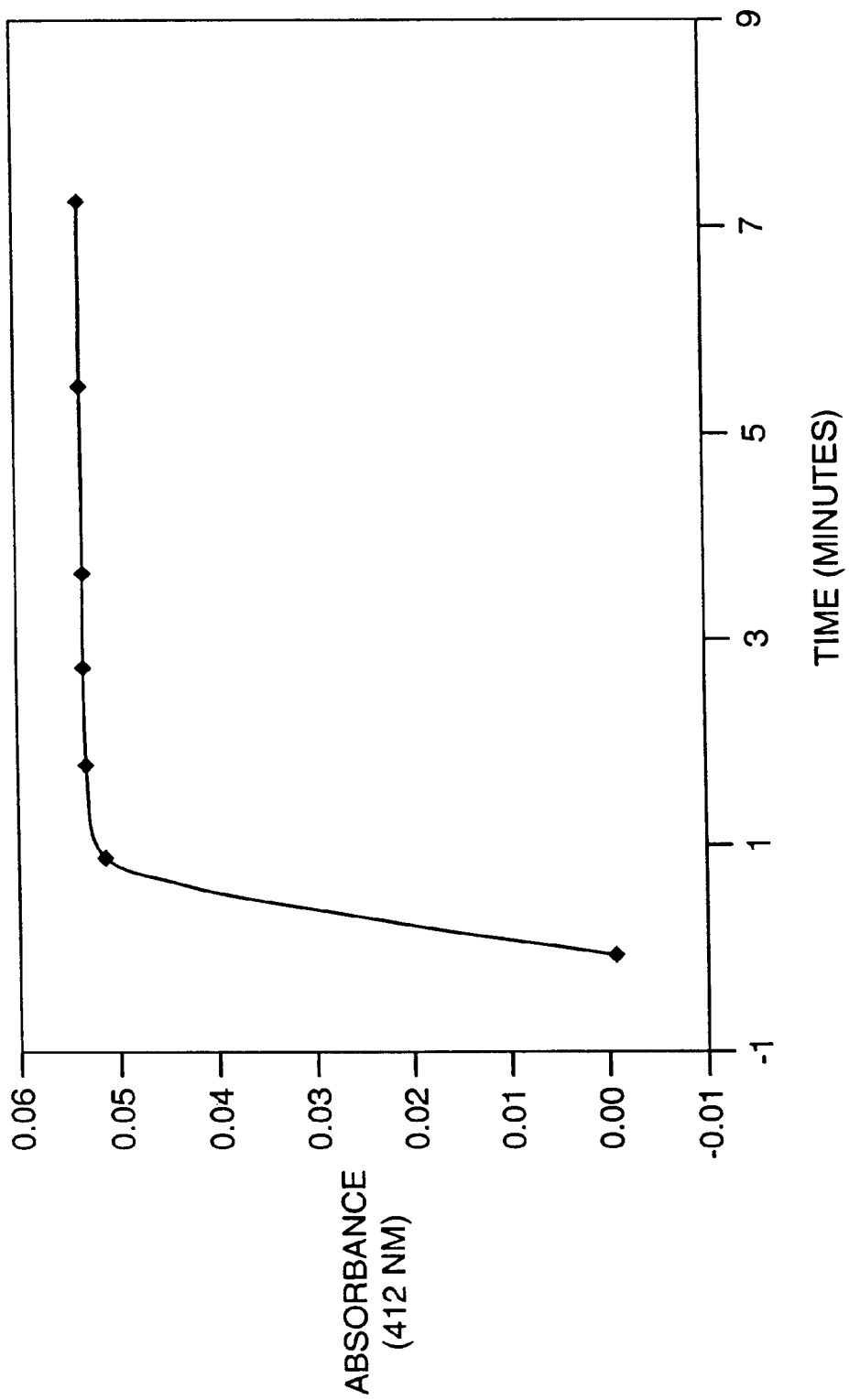
FIG. 15 shows the absorbance at 412 nm of liposomes containing 1,2-bis-(S-decanoyl)-1,2-dithio-sn-glycero-3-phosphocholine (DTPC) following exposure to $PLA_2$ for various lengths of time.

In order to confirm that biocatalysis was occurring at the DMPC/PDA vesicles, $PLA_2$ activity was independently measured using a labeled lipid analog incorporated into the PDA matrix, allowing simultaneous measurement of product formation and calorimetric response of the vesicles. The analog used was thioester 1,2-bis-(S-decanoyl)-1,2-dithio-sn-glycero-3-phosphocholine (DTPC). Cleavage of DTPC by $PLA_2$ produces a soluble thiol-modified lipid that readily reacts with 5,5'-dithiobis-2-nitrobenzoic acid (DTNB) to produce a colored product that characteristically absorbs at 412 nm (Reynolds et al., supra). Indeed, when $PLA_2$ was added to mixed 40% DTPC/PDA vesicles, the hydrolysis products reacting with DTNB gave rise to a significant absorption at 412 nm as shown in FIG. 15. At the same time, the PDA vesicles also changed color, and the suspension exhibited a colorimetric response similar to that of the vesicles containing DMPC shown in FIG. 13. These results confirm that interfacial catalysis by $PLA_2$ occurred at the polymerized mixed vesicles.

Figure 16B:
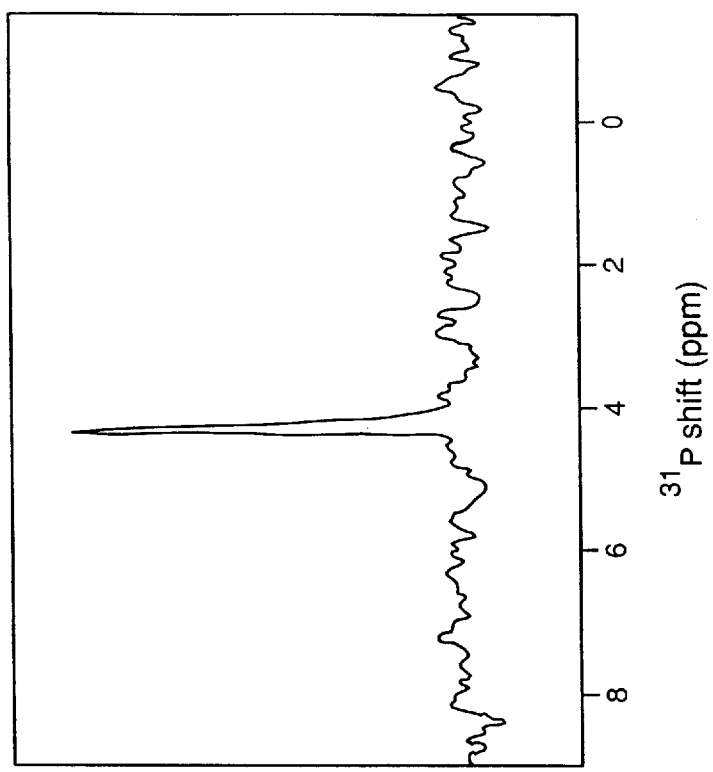
FIG. 16 shows $^{31}P$ NMR spectra of the DMPC/PDA vesicles prior to the addition of $PLA_2$ (A), and following the enzymatic reaction (B).
Figure 16A:
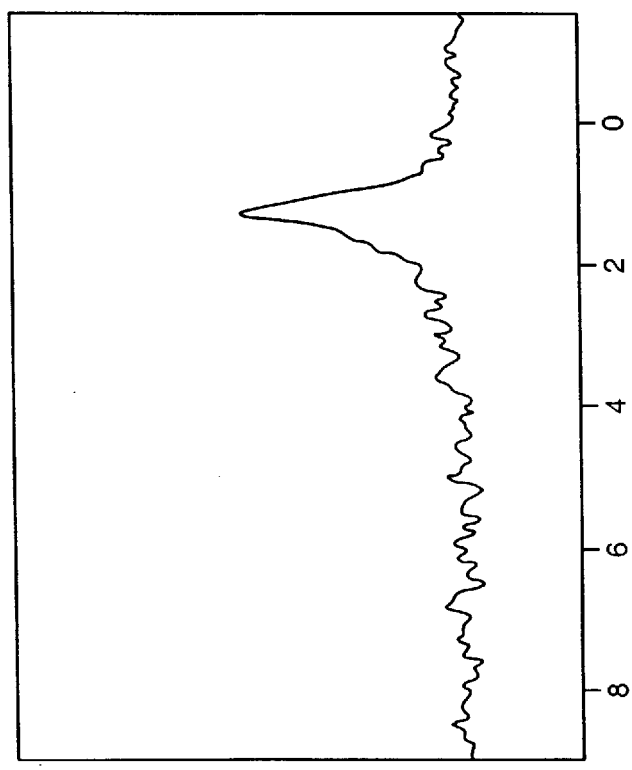

NMR experiments further verified the occurrence of interfacial catalysis by $PLA_2$, and provided information of the fate of the enzymatic reaction products. FIG. 16 features $^{31}P$ NMR spectra of the DMPC/PDA vesicles prior to the addition of $PLA_2$ (FIG. 16A), and following the enzymatic reaction (FIG. 16B). The relatively broad, anisotropic $^{31}p$ resonance from the intact vesicles, FIG. 16A, corresponds to the choline head-group of DMPC embedded in the PDA vesicles. The observation of $^{31}P$ anisotropy in FIG. 16A indicates that DMPC molecules are immobilized within the vesicle matrix. After addition of $PLA_2$, the $^{31}P$ signal was shifted downfield as shown in FIG. 16B. The position of the $^{31}P$ resonance in FIG. 16B coincides with the shift observed for the water-solubilized lyso-myristoylphosphatidylcholine, the hydrolysis product of DMPC. Furthermore, FIG. 16B shows that the $^{31}P$ resonance observed in the suspension of the enzyme-treated vesicles becomes significantly narrower than the $^{31}P$ signal from the initial DMPC/PDA vesicle, FIG. 16A, indicating a higher mobility of the phosphate group following $PLA_2$ catalysis (Smith and Ekiel, *Phosphorous*-31 *NMR, Principles and Applications*, Academic Press, Orlando, pp 447 [1984]). This result suggests dissolution of the lysolipid reaction products following the enzymatic reaction. $^1H$ NMR data indicating the appearance of a distinct lysolipid phase following the reaction with $PLA_2$ further supported this description.

B. Others Phospholipases

Colorimetric detection of interfacial catalysis by other enzymes such as phospholipase C (PLC) and phospholipase D (PLD) has been also achieved using the substrate-modified PDA vesicles, demonstrating that the methodology described by the present invention is generally applicable. These phospholipases cleave the polar head group region of glycerophospholipids, whereas phospholipase $A_2$ cleaves the acyl ester bond exclusively at the 2-acyl position.

The assay test for phospholipase D and C were run under similar conditions as the $PLA_2$ assays. Both PLD and PLC activity were successfully detected by the liposomes assay. The PLD assay yielded a final colorimetric response of approximately 55%. However, the shape of the response curve was more gradual than that of $PLA_2$. Although it is not necessary to understand the mechanism in order to use the present invention, and it is not intended that the present invention be so limited, it is contemplated that either the kinetics of the PLD-catalyzed reaction are different or that the response time between the catalytic event and the color change is slower. The PLC assay yielded a final calorimetric response of 60% and the response curve was similar to that of $PLA_2$. NMR experiments further verified the occurrence of interfacial catalysis by PLC and PLD.

C. Bungarotoxin (BUTX)

$\beta$-bungarotoxin, a snake toxin from *Bungarus multicinctus*, is known to destroy synaptic vesicles and inhibit acetylcholine release. It is classified as a $PLA_2$ toxin and is composed of two subunits: a 12-kDa subunit that exhibits $PLA_2$ activity and a 7.5-kDa subunit that shares sequence homology with protease inhibitors.

Experiments with bungarotoxin and 40% DMPC/60% 10,12-tricosadiynoic acid (TRCDA) liposomes displayed a maximum colorimetric response of approximately 50% after a one hour incubation time. The response curve was similar to that of the $PLA_2$ assay. In addition, after incubation with BUTX, the liposomes in the assay solution not only changed color, but also precipitated. In a previous study, BUTX was shown to induce fusion of small unilamellar liposomes (Rufini et al., Biochemistry 29, 9644 [1990]). The mechanism of the fusion remains unclear, but it seems to be dependent upon the interaction between BUTX, $Ca^{2+}$, and lysophospholipids.

This bungarotoxin assay provides an example of a large molecular assembly possessing enzymatic properties that is capable of producing a colorimetric change in the biopolymeric materials. In some embodiments, it may be desired to add additional bungarotoxin-detecting features to the biopolymeric materials to enhance the colorimetric detection. For example, antibodies raised against bungarotoxin (i.e., ligands) can be incorporated onto the biopolymeric materials in addition to DMPC. Thus, when bungarotoxin is present in a sample, the ligand/analyte interaction and the enzyme/substrate reaction will combine to provide an enhanced colorimetric response.

D. Other Enzyme Systems

The present invention will find use in detecting, measuring, and characterizing the enzyme activities of many other systems including, but not limited to, lipolytic enzymes, acyltransferases, protein kinases, glycosidases, isomerases, ligases, polymerases, and proteinases, among others. Such enzymes can be free in solution, or be part of larger molecular aggregates, cells, and pathogens. For a general description of biocatalytic events, the reader is directed to Dordick (Dordick, *Biocatalysts for Industry*, Plenum Press [1991]).

For example, glycosidases can be detected to measure their activity or as indicators of the presence of a pathogen. Sialidases such as neuraminidase are found on influenza virus, and other sialidases are associated with Salmonella. By providing biopolymeric materials with substrate for the glycosidases, the presence of the pathogens can be detected. In combination with other detection elements (e.g., sialic acid ligands for detection of influenza virus), extremely sensitive calorimetric sensors can be produced.

Substrates can also be provided to produce detection systems for proteinases. For example, *Candida albicans* can be detected though its protease activity on pepstatin substrates. Also, anthrax spores from *Bacillus anthracis* can be detected by identifying laccase activity though its reaction with a substrate. Laccases are multi-copper-containing enzymes that catalyze oxidative conversion of a variety of substrates, including phenols, poly-phenols, and aromatic amines. Specific substrates include vanillic acid, syringic acid, and 2-2'-azino-bis(3-ethyl-benzthioazoline-6-sulfonic acid). By introducing one or more of these known laccase substrates into the biopolymeric materials of the present invention, a detection assay for antrax spores may be generated.

Other applications include incorporation of nucleic acids onto the biopolymeric material to test the activity of nucleotide polymerases (e.g., DNA polymerase). These assay systems will find use in techniques for identifying and characterizing polymerase inhibitors. From these examples, it is clear that the biopolymeric materials of the present invention find use in the colorimetric detection of a broad array of membrane conformational changes and reactions.

E. Inhibitor Screening

As described above, the present invention provides methods for detecting the activity of enzymes and other molecules that alter the conformation of biopolymeric membranes. These methods can be expanded to provide an accurate, and fast screening technique for identifying and characterizing inhibitors of the activity responsible for the calorimetric change (e.g., identifying and characterizing protease inhibitors by subjecting candidate inhibitors to biopolymeric materials comprising the protein substrates for the enzymes).

Figure 17:
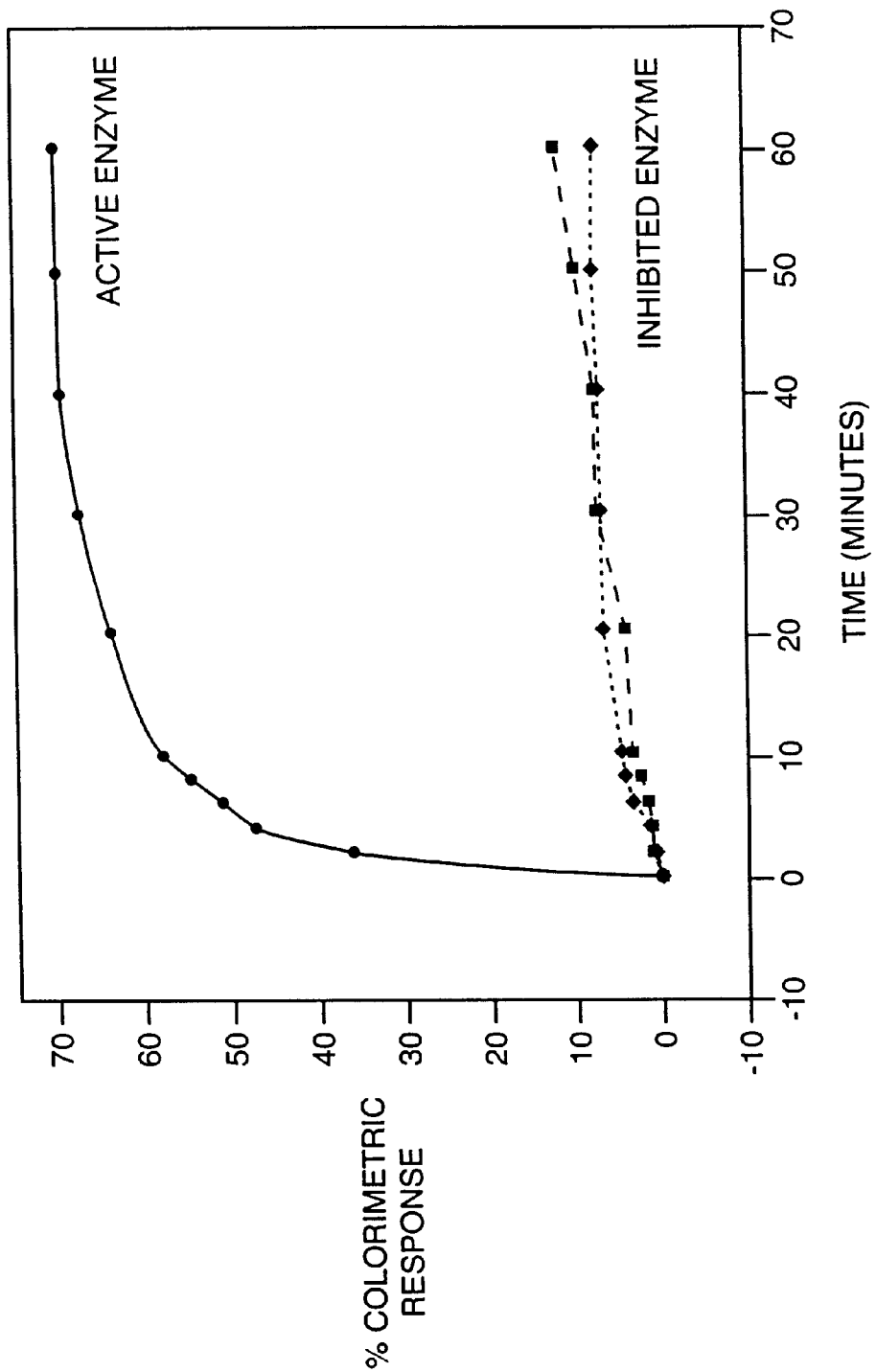
FIG. 17 shows the calorimetric response of DMPC containing liposomes in the presence of $PLA_2$ (circles), and $PLA_2$ with inhibitors (squares and diamonds).

For example, with the detection of $PLA_2$ enzyme activity described above, the color change of the DMPC/PDA vesicles can be suppressed by using inhibitors to $PLA_2$. In the presence of the inhibitor 1-hexadecyl-3-trifluoroethylglycero-2-phosphomethanol (MJ33) (Gelb et al., supra; and Jain et al., Biochemistry 30, 10256 [1991]), the vesicles remained in their blue phase upon addition of $PLA_2$. These color differentials were clearly visualized for $PLA_2$/vesicle suspension in the presence (blue) and absence (red) of MJ33 in a 96-well microtiter plate. The absorbance of the wells was measured using a standard microplate reader, and quantitatively confirmed the suppression of the colorimetric response as shown in FIG. 17. This figure shows the colorimetric response curves for DMPC/PCA vesicles in the absence of inhibitor (solid line, max error 1.9%) and in the presence of MJ33 (dashed line, squares, max error 6.9%). Also shown is the inhibition of $PLA_2$ by replacement of $Ca^{2+}$ with $Zn^{2+}$ (dashed line, diamonds, max error 6.5%).

The inhibition of the blue to red color change by MJ33 indicates that non-specific adhesion does not play a role in the biochromic response, and $PLA_2$ activity is directly responsible for the color change. Inactivation of $PLA_2$ is also observed upon removal of $Ca^{2+}$, the catalytic co-factors for $PLA_2$ (Gelb et al., supra), from the buffer solution. Similarly, $PLA_2$ prepared in buffer containing $Zn^{2+}$ instead of $Ca^{2+}$ ions does not induce a blue to red color change of the vesicles as shown in FIG. 17 (dashed line, diamonds). The vesicles also do not change color in the presence of other enzymes such as lysozyme and glucose oxidase, both of which produce a colorimetric response below 5% after more than an hour of incubation with the 40% DMPC/PDA vesicles. The specificity of the colorimetric response provides the necessary selectivity for high throughput screening of enzyme inhibitors.

For screening inhibitors, biopolymeric material comprising a substrate for the enzyme being tested, are placed into a multi-chambered device (e.g., a 96-well plate). Each well is incubated with a sample suspected of containing an enzyme inhibitor. The enzyme is then added and the observation of a color change is detected. Successful inhibitors will partially or completely prevent the enzyme from producing a color change in the biopolymeric material. Appropriate control samples (e.g., a sample with no inhibitor and a sample with known inhibitor) are run with the assay to provide confidence in the results.

F. Designed Catalysts

The biopolymeric materials of the present invention further provide methods for screening the efficacy and activity of "designed" proteins, peptides, and catalytic antibodies. There is much current activity in engineering enzymes to be stable under specific conditions of solvent and heat, among other conditions. By providing a substrate for such enzymes in the biopolymeric materials of the present invention, a simple, accurate screen of these engineered proteins can be conducted under a variety of test conditions. Likewise, the inventive methods can be used to screen and characterize the reactions of catalytic antibodies.

VII. IMMOBILIZATION OF BIOPOLYMERIC MATERIALS

The biopolymeric material of the present invention can be immobilized on a variety of solid supports, including, but not limited to polystyrene, polyethylene, teflon, silica gel beads, hydrophobized silica, mica, filter paper (e.g., nylon, cellulose, and nitrocellulose), glass beads and slides, gold and all separation media such as silica gel, sephadex, and other chromatographic media. In some embodiments, the biopolymeric materials were immobilized in silica glass using the sol-gel process.

Immobilization of the colorimetric biopolymeric materials of the present invention may be desired to improve their stability, robustness, shelf-life, colorimetric response, color, ease of use, assembly into devices (e.g. arrays), and other desired properties. In some embodiments, placement of calorimetric materials onto a variety of substrates surfaces can be undertaken to create a test method similar to the well-known and easy to use litmus paper test. For example, the reflective properties of nylon filter paper greatly enhance the colorimetric properties of the immobilized polydiacetylene liposomes. Filter paper also increases the stability of the liposomes due to the mesh size.

In another example, the liposome embodiment of the present invention has been loaded into the ink cartridge of a inkjet printer and used to print biopolymeric liposome material onto paper as though it were ink. The liposome material present on the paper maintained its colorimetric properties. This embodiment demonstrates the ease with which patterned arrays can be generated into any desired shape and size. By using multiple cartridges (e.g., using a color printer), patterned arrays can be generated with different biopolymeric materials.

In some embodiments of the present invention, liposome layers on thin support (i.e., printing paper, plastic sheets, overhead transparencies, etc.) were patterned, using a regular inkjet printer. The printer was used by filling the printing cartridge with the liposome solution. This allowed patterning in the range from several tens of cm down to the sub mm region (resolution limit of the printer), and the pattern was easily designed and printed from any personal computer application (e.g. drawing program, word processor). The printed liposomes were photopolymerized after drying with the resulting polymer being strongly absorbed, and even organic solvents like acetone or $CH_2Cl_2$ did not dissolve the created pattern. This method represents an ideal approach to the generation of test stick type applications or array type assays. An additional advantage is the efficient use of the liposome material which is applied in thin films, and used completely in the assay (i.e., no loss due to washing or functionalization steps).

The general working procedure consists of the following steps: i) preparation of the liposome solution ($\geq 5$ ml, 2–10 mM) and filling of the cartridge with it; ii) priming and flushing of the cartridge with an ink intensive print pattern immediately followed by printing of the desired liposome pattern; and iii) photopolymerization of the liposome printout.

In the course of experiments, several problems were observed. Polymerization yield depended on paper type with regular white copy paper generally giving good results. On higher quality papers (i.e., laser printer paper, color printer paper) the printed liposomes did not polymerize as well, which also depended on the type of liposomes. Pure TRCDA (10 mM) or PDA (2 mM) liposomes polymerized with slightly reduced yield compared to regular paper, but TRCDA liposomes containing 20% of a sialic acid lipid (SA-PDA) did not polymerize at all on such high quality paper. On the other hand SA-PDA containing liposomes polymerized well on standard paper or overhead transparencies. In other experiments, print nozzles clogged after a short time. This was most likely due to evaporation of water and aggregation of liposomes in the nozzles. To prevent clogging, 5–30% ethanol was added to the liposome solution which was quite effective for declogging the nozzles, although polymerization yields dropped. The nozzles can be cleared by washing with ethanol and flushing with liposome solution by pressurizing the cartridge with $N_2$ or air, forcing the liquid inside the cartridge through the printing nozzles. It is contemplated that the additives like glycerol and polyethyleneglycol may be added to prevent evaporation of water, resulting in the prevention of prevent liposome aggregation without affecting polymerization yields. In alternative embodiments, the nozzle is redesigned to prevent clogging (e.g., redesigning the shape or using different materials).

A. Entrapment of Biopolymeric Material by the Sol-Gel Method

While the sol-gel process has been used for entrapping organic molecules such as dyes and biomolecules in silica gels (See e.g., Avnir, Accounts Chem. Res. 28: 328 [1995]; Yamanaka et al., Am. Chem. Soc. 117: 9095 [1995]; Miller et al., Non-Cryst. Solids 202: 279 [1996]; and Dave et al., Anal. Chem. 66: 1120A [1994]), prior to the development of the present invention, immobilization of self-organized molecular aggregates (e.g., biopolymeric material, self-assembling monomer aggregates, and liposomes) was not realized in sol-gel materials.

Embodiments of the present invention provide for the successful immobilization of spherical, bilayer lipid aggregates, and liposomes using an aqueous sol-gel procedure. These molecular structures, and particularly liposomes, composed of biological or biomimetic (i.e., mimics nature) lipids, are fairly robust under aqueous conditions and ambient temperatures, but can easily degrade in the presence of organic solvents and high temperatures. The sol-gel process provides a facile method of immobilizing molecular aggregates with no detectable structure modification, creating robust structures that are easily fabricated into any desired size or shape.

The silica sol-gel material was prepared by sonicating tetramethylorthosilicate, water, and hydrochloric acid under chilled conditions until a single phased solution was obtained. The use of metal oxides, other than tetramethylorthosilicate, are contemplated by the present invention, so long as they facilitate the entrapment and form substantially transparent glass material. Such metal oxides include, but are not limited to, silicates, titanates, aluminates, ormosils, and others. Buffer was then added to the acidic solution under cooling conditions. The biopolymeric materials, generated as described above, were mixed into the buffered sol solution. This composite was poured into a desired molding structure and allowed to gel at ambient temperatures. It is not intended that the present invention be limited by the type of molding structure used, as it is contemplated that a variety of structures can be applied to generate gels of any desired size and shape including, but not limited to, cuvettes, flat surfaces for generating thin films, plastic, ceramic, or metal moldings to generate badges, etc. It is not intended that the present invention be limited to gelation at ambient temperatures, as any temperature range that facilitates the production of functional analyte-detecting gels is contemplated.

Figure 18:
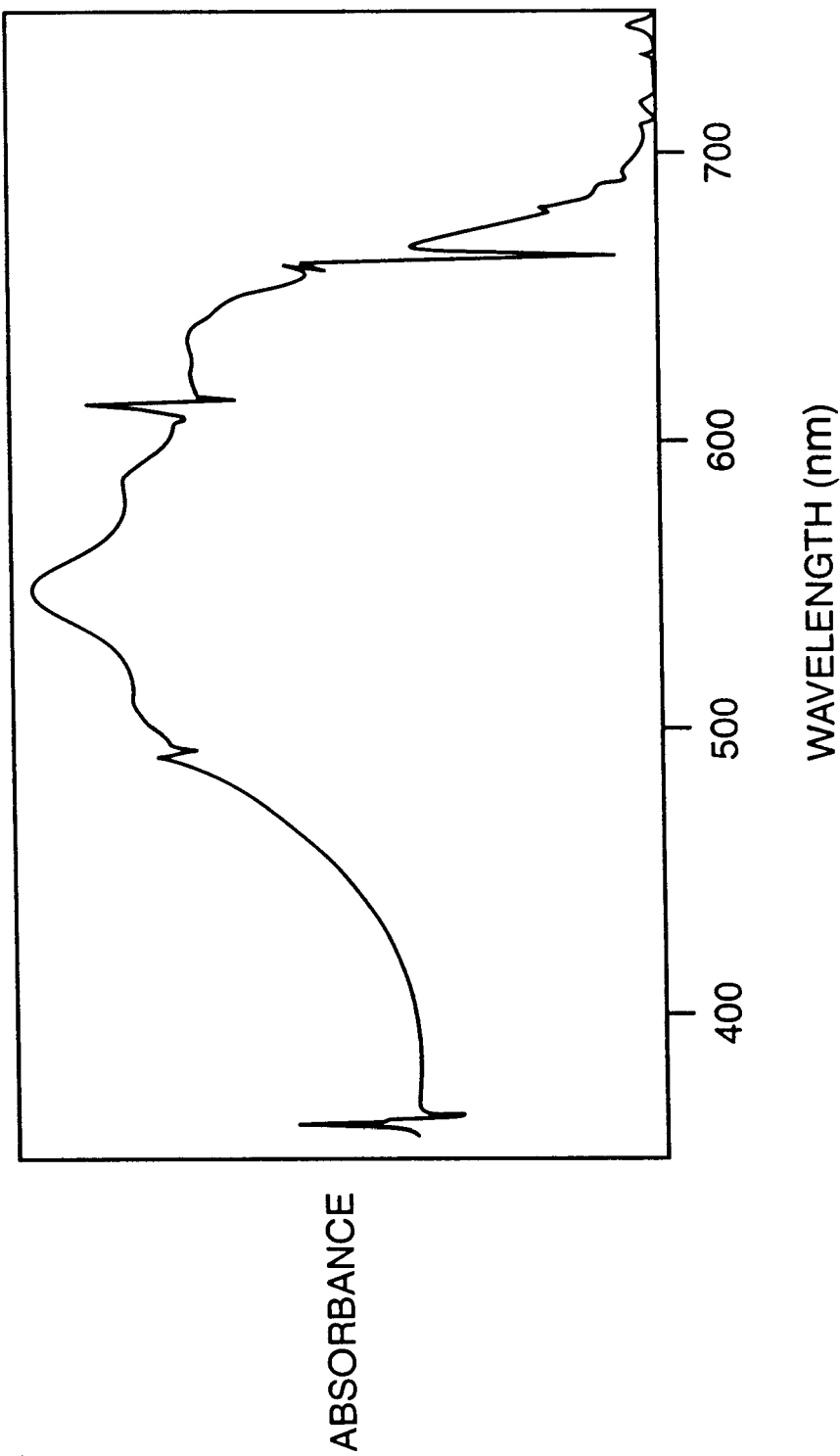
FIG. 18 shows the visible absorption spectra of the polydiacetylene liposomes in a sol-gel matrix.
Figure 19:
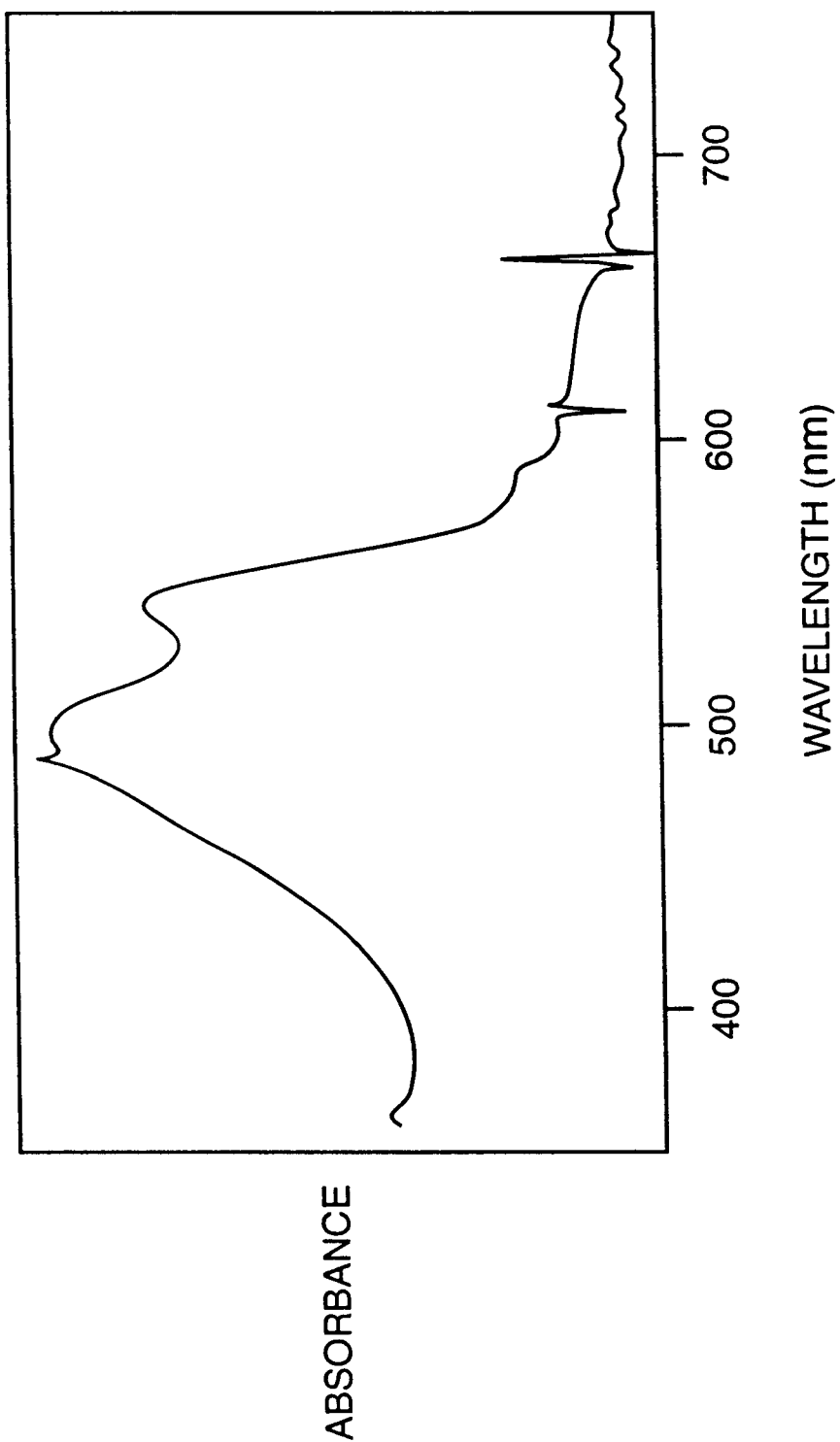
FIG. 19 shows the visible absorption spectra of the material in FIG. 18 following heating of the liposomes to 55° C.

In one embodiment, DCDA liposomes were incorporated into sol-gel glass, although incorporation of any biopolymeric structure is contemplated by the present invention. Following the sol-gel procedure as described above, gelation occurred within a few minutes, producing gels with a violet color. The visible absorption spectra of the polydiacetylene liposomes, as shown in FIG. 18, was unaltered in the sol-gel matrix compared to liposomes in solution. Following heating of the liposomes to 55° C., a blue to red thermochromic transition occurred that was characteristic of polydiacetylene materials. The blue to red phase materials were similarly unchanged in the sol-gel state compared to solution as shown in the spectrum in FIG. 19. Thus, the present invention provides a sol-gel matrix that is compatible with fragile biopolymeric structures (i.e., liposomes) and maintains those physical properties that were observed in bulk solution.

Additionally, it is contemplated that sol gel prepared materials of various thicknesses will possess unique sensitivities to analytes. Thicker films have a higher surface to volume ratio and therefore may require a higher concentration of analyte to trigger the chromatic transition.

Furthermore, the gelling conditions of the sol-gel preparation can be optimized by varying gelling temperatures, gel materials, and drying conditions to generate material with desired pore sizes. Varying the crosslink density of the material also provides control over pore size. Pore sizes from nanometers to hundreds of nanometers or greater are contemplated by the present invention. Some gels allow size-selective screening of undesired material while maintaining analyte access to the ligand. Also, the sol-gel technique allows structures to be formed that can be molded into any desirable shape, including, but not limited to, cartridges, coatings, monoliths, powders, and fibers.

B. Immobilization by Chemical Linkage

In some embodiments of the present invention, the biopolymeric material can be attached to membranes of poly(ether urethanes) or polyacrylonitrile. These membranes are porous, hydrophilic and can be used for affinity separations or immunodiagnosis. The liposomes of the present invention can be coupled to these membranes by first attaching an activating group such as imidizolyl-carbonyl, succinimido, FMP or isocyanate to the membrane which adds rapidly to nucleophiles (e.g. $-NH_2$, $-SH$, or $-OH$ groups) present in the liposomes. Thus, any liposome preparation which contains these functionalities can be directly attached to the membrane. This procedure is analogous to the coupling of proteins to membranes, the latter of which is well known in the art (See e.g., Bamford et al., Chromatography 606: 19 [1992]).

A variety of other immobilization techniques known in the art can be applied to the biopolymeric material of the present invention. For example, materials which have an $-SH$ functionality can also be immobilized directly to gold surfaces, particles, or electrodes via the thiol-gold bond. In this case, a solution of the liposomes containing the $-SH$ group are incubated with the clean gold surface in water for 12–24 hours with stirring at room temperature. Also, materials can be immobilized to silicon chips or silica gel (e.g., silicon dioxide) using the procedure described in Example 8. Furthermore, materials containing $-NH_2$ functionalities can also be immobilized onto surfaces with standard glutaraldehyde coupling reactions that are often used with the immobilization of proteins. Additionally, liposomes can be attached through their carboxy groups to surfaces comprising polyethyleneimine, a branched polymer with free amine groups.

VIII. ARRAYS

Certain embodiments of the present invention contemplate the generation of a large palette of polymerizable lipids with different headgroup chemistries, ligands, dopants, monomers or other properties within a single device to increase selectivity, sensitivity, quantitation, ease of use, and portability, among other desired characteristics and qualities. By using the array format, several advantages can be realized that overcome the shortcomings of a single sensor approach. These include the ability to use partially selective sensors and to measure multicomponent samples. This offers the possibility of sensing a specific sample in the presence of an interfering background, or to monitor two or more samples of interest at the same time. The sensitivities of a given lipid to a given sample can be determined in order to generate identifiable fingerprints characteristic of each sample. For example, the lipid-polymer film of PDA derivative A may convert completely to an orange phase in the presence of sample X (% CR=100), while PDA derivative B may have a % CR of 70 giving rise to a pink color, and PDA derivative C may have a % CR of 40 yielding a purple color and PDA derivative D may not change at all (i.e., therefore, remains blue/purple). The response fingerprint orange/pink/purple/blue-purple would indicate the presence of sample X. Clearly, the higher the number of elements in the array, the greater the chance of a positive identification for a given analyte. By immobilizing the biopolymeric material, materials of any desired size and shape can be created and incorporated into a small, easily read, and interpretable device.

Arrays can be generated that measure both the presence and activity of samples. For example, when characterizing a certain enzyme, one portion of the array can provide analyte-detecting capabilities for the enzyme (e.g., by incorporating a ligand that interacts with the enzyme), while another provides and enzyme activity assay (e.g., by including a substrate for the enzyme within the biopolymeric material). Such arrays can be expanded for use in inhibitor screening techniques where each portion of the array provides quantitative or qualitative data, or provides a control experiment.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); $\mu$mol (micromoles); nmol (nanomoles); pmol (picomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); $\mu$Ci (microcurie); mN (millinewton); Å (angstrom); kDa (kilodalton); ppm (parts per million); N (newton); ° C. (degrees Centigrade); RT (room temperature); h (hour or hours); wt % (percent by weight); aq. (aqueous); J (Joule); UV (ultraviolet); XPS (x-ray photoelectron spectroscopy); PDA (diacetylene monomer); PCA (pentacosadiynoic acid monomer); DCDA (docosadynoic acid); TRCDA (tricosadiynoic acid); SA-PDA (sialic acid-derived PDA); BUTX (bungarotoxin); OTS (octadecyltrichlorosilane); VOC (volatile organic chemical); CR (colorimetric response); pH (hydrogen ion concentration); EDC (ethylcarboiimide hydrochloride); AFM (atomic force microscope); Hz (Hertz); LB (Langmuir-Blodgett); NHS (N-hydroxy succinimide); $CO_2$ (carbon dioxide); $MgSO_4$ (magnesium sulfate); $CdCl_2$ (cadmium chloride); MeOH (methanol); Be (beryllium ions); Mg (magnesium ions); Ca (calcium ions); Ba (barium ions); $N_2$ (nitrogen gas); Sigma (Sigma Chemical Co., St. Louis, Mo.); Perkin-Elmer (Perkin-Elmer Co., Norwalk, Conn.); Fisher (Fisher Scientific, Pittsburgh, Pa.); and Farchan Laboratories (Farchan Laboratories, Inc., Gainesville, Fla.); Park Scientific Instrument (Park Scientific Instruments, Sunnyvale, Calif.); Biorad (Bio-Rad Laboratories, Hercules, Calif.); Gelman (Gehnan Sciences, Ann Arbor, Mich.); Pierce (Pierce, Rockford, Ill.); and Bellco Glass (Bellco Glass Inc., Vineland, N.J.).

All compounds were of reagent grade purity and used as supplied unless stated otherwise. Organic solvents were of spectral grade from Fisher Scientific. All aqueous solutions were prepared from water purified through a Barnstead Type D4700 NANOpure Analytical Deionization System with ORGANICfree cartridge registering an 18.0 M-Ohm-cm resistance.

EXAMPLE 1

Biopolymeric Material Preparation
I. Production of Liposomes

The self-assembling monomers to be incorporated into the liposomes were dissolved in solvent (e.g., chloroform for diacetylenes and methanol for ganglioside $G_{M1}$). Many other volatile solvents find use in the present invention, including, but not limited to, benzene, hexane, and ethylacetate. The solvent solutions were mixed in appropriate volumes in a brown vial (i.e., to prevent light interference during the upcoming drying steps) to achieve the desired lipid mixture (e.g., 5% by mole of $G_{M1}$, 95% diacetylenes) and a total lipid content of approximately 2 μmol. The solvent was then evaporated by rotary evaporation or with a stream of nitrogen gas. The dried lipids were resuspended in sufficient de-ionized water to produce a 1–15 mM solution of lipid. The solution was then sonicated for 15–60 minutes with a probe sonicator (Fisher sonic dismembrator model 300, 50% output, microtip) as described by New (New, supra). The solution was heated during the sonication (in most cases the sonicating process alone provides sufficient heat) to a temperature above the phase transition of the lipids used (typically 30–90° C.). The resulting mixture was filtered through a 0.8 micromole nylon filter (Gelman) or through a 5 mm Millipore Millex-SV filter and cooled to 4° C. for storage or was polymerized. In one embodiment, prior to polymerization, oxygen in the solution was removed by bubbling nitrogen through the sample for 5–10 minutes.

Polymerization of the stirred liposome solution was conducted in a 1 cm quartz cuvette with a small 254 nm UV-lamp (pen-ray, energy: 1600 microwatt/cm$^2$) at a distance of 3 cm. The chamber was purged with nitrogen during the polymerization to replace all oxygen and to cool the sample. Polymerization times varied between 5 and 30 minutes depending on the desired properties (e.g., color, polymerization degree) of the liposomes. In other embodiments, the solution was placed in a UV-chamber, without purging, and exposed to 0.3–20 J/cm$^2$ of ultraviolet radiation, preferably 1.6 J/cm$^2$, for 5–30 minutes.

In some embodiments, polymerization was conducted in a multi-chambered plate (e.g., ELISA plate). Approximately 200 μl of sonicated liposome solution was placed in each well of the plate. The plate was placed under a UV lamp with the distance between the plate and the lamp kept at 3 cm. Irradiation times typically lasted for a minute. Prolonged irradiation resulted in formation of pink/purple liposomes, indicating that a color change was initiated by UV light. Such liposomes gave inconsistent results and should be avoided.

II. Production of Films

Polydiacetylene films were formed in a standard Langmuir-Blodgett trough (See e.g., Roberts, *Langmuir Blodgett Films*, Plenum, N.Y. [1990]). The trough was filled with water to create a surface for the film. Distilled water was purified with a millipore water purifier with the resistivity of 18.2 M-Ohm. Diacetylene monomers (e.g., 5,7-docosadiynoic acid, 10,12-pentacosadiynoic acid [Farchan Laboratories], 5,7-pentacosadiynoic acid, combinations thereof, or other self assembling monomers), dissolved in a solvent spreading agent (e.g., spectral grade chloroform [Fisher]), were layered onto the aqueous surface with a syringe, to form a continuous film. Monomers prepared in the concentration range of 1.0 to 2.5 mM, were kept at a temperature of 4° C. in the dark, and were allowed to equilibrate at room temperature before being used in experiments.

Once layered on the water surface, the film was physically compressed using moveable barriers to form a tightly-packed monolayer of the self-assembling monomers. The monolayer was compressed to its tightest packed form (i.e., until a film surface pressure of 20–40 mN/m was achieved). Following compression, the film was polymerized. Certain embodiments (e.g., embodiments with dopants) of the present invention may require surface pressure compression greater or less than 20–40 mN/m.

Ultraviolet irradiation was used to polymerize the monomers, although other means of polymerization are available (e.g., gamma irradiation, x-ray irradiation, and electron beam exposure). Pressure was maintained on the film with the moveable barriers throughout the irradiation process at surface pressure of 20–40 mN/m. An ultraviolet lamp was placed 20 cm or farther from the film and trough. It was found that if the lamp is placed closer to the film, damage to the diacetylene film may occur due to the effects of heating the film. The film was exposed to ultraviolet light with a wavelength of approximately 254 nm for approximately one minute. The polymerization was confirmed by observing the blue color acquired upon polymerized diacetylene formation and detecting the linear striations typical of polymerized diacetylene films with a polarizing optical microscope.

III. Production of Tubules

Self-assembling monomers to be incorporated into the tubules were dissolved in solvent, mixed together, evaporated, and resuspended in water as described above for liposomes. 1–10% by volume of ethanol was added to the solution, although other organic solvents are contemplated by the present invention. The solution was then sonicated (with heating if necessary), filtered, cooled, and polymerized as described above for liposomes.

EXAMPLE 2

Examination of Biopolymeric Materials

1. Optical Microscopy and X-ray Spectroscopy

Diacetylene films were prepared in a Langmuir Blodgett trough as described above using a combination of PDA monomers and sialic acid-derived PDA monomers. The floating polymerized assembly was lifted by the horizontal touch method onto a glass slide previously coated with a self-assembled monolayer of octadecyltrichlorosilane (OTS) as described (Maoz and Sagiv, J. Colloid Interface Sci. 100: 465 [1984]).

Figure 20:
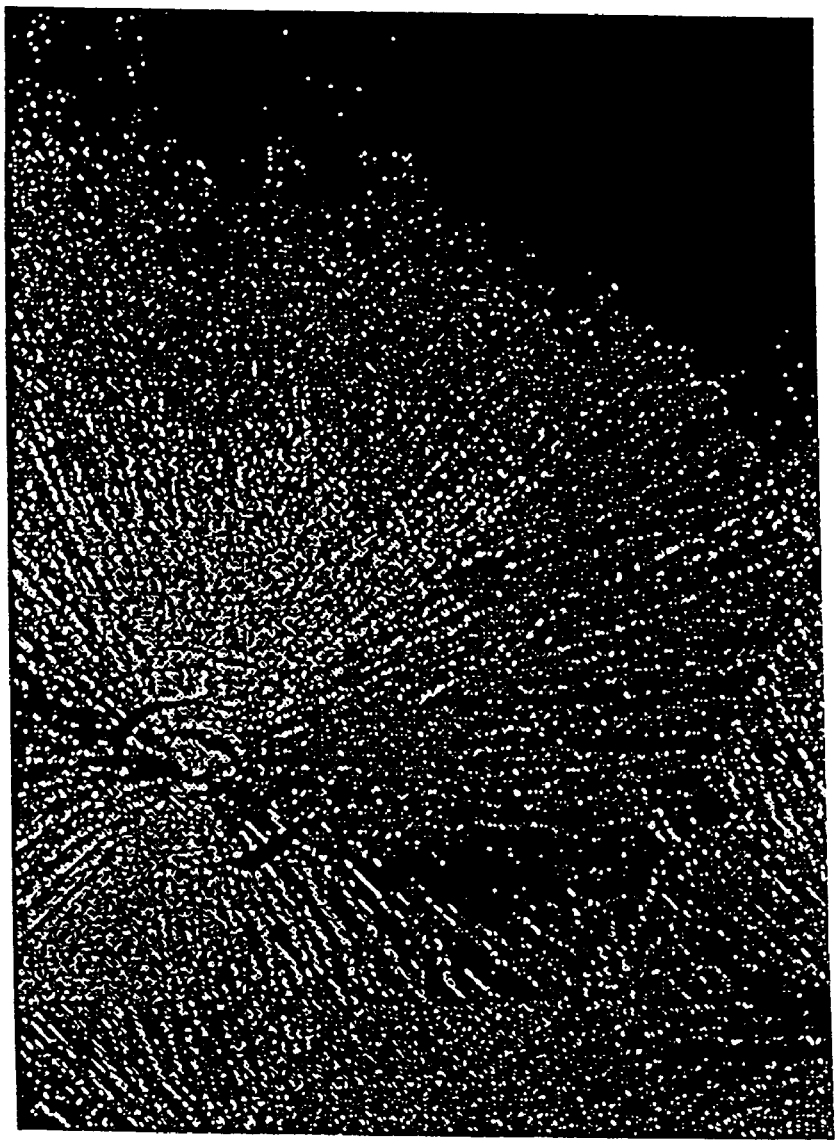
FIG. 20 shows an optical micrograph of diacetylene film.

The slide was then examined by optical microscopy with the use of crossed polarizers as described (Day and Lando, Macromolecules 13: 1478 [1980]). The film exhibited a high degree of order over a macroscopic range (i.e., 50 to 150 μM) as shown in the optical micrograph of FIG. 20. Large domains up to 150 μM were visible (1 cm=10 μM).

The films were further characterized by angle-resolved x-ray photoelectron spectroscopy (XPS) and ellipsometry. The XPS results indicated that the amide nitrogen atoms and the carbonyl carbon atoms of the head groups were localized at the surface relative to the methylene carbons of the lipid chains, demonstrating that the sialoside head group was presented at the surface of the film. Ellipsometric analysis of the polydiacetylene monolayer coated on HF-treated silicon indicated a film thickness of approximately 40 Å, in agreement with the expected value based on molecular modeling.

II. Atomic Force Microscopy

In situ atomic force microscopy was used to reveal the morphology, surface topography, and growth and dissolution characteristics of microscopic biopolymeric crystals, and allowed dynamic observations of nucleation events and the determination. Studies were conducted using standard techniques for in situ studies as described by Binnig et al. (Binnig et al., Phys. Rev. Lett. 12: 930 [1986]; and Binnig et al., Europhys. Lett. 3: 1281 [1987])

Two different atomic force microscopes were used in this study. Images larger than 1 μm$^2$ were acquired with a commercially available instrument (Park Scientific Instrument). In this case Si ultralevers (Park Scientific Instrument) were used. Commercially available photolithographically patterned glass slides (Bellco Glass) were used to allow imaging of the exact same region of the film after each temperature step. Images smaller than 1 $\mu m^2$ were taken with a home-built AFM (Kolbe et al., Ultramicroscopy 42–44: 1113 [1992]). $Si_3N_4$ cantilevers with a nominal force constant of 0.1 N/m were used (Park Scientific Instruments). Both microscopes were operated in contact mode, and in the latter case a four-quadrant position-sensitive photodiode allowed the measurement of the cantilever bending and twisting simultaneously. All images were acquired in contact mode under ambient conditions.

EXAMPLE 3

Optimization of Biopolymeric Materials

The present invention provides a variety of different biopolymeric material forms (e.g., liposomes, films, tubules, etc.), with and without dopant materials, with a variety of ligands, and immobilized in a variety of forms. For each of these embodiments, it is possible to optimize the biopolymeric material to maximize sensitivity, robustness, colorimetric response, and other desired factors. Described below are a few illustrative examples of such optimization. These examples are intended to merely illustrate the flexibility of the present invention. It is not intended that the present invention be limited to these particular embodiments.

I. Mixed Monomers

The biopolymeric material of the present invention can comprise a sample of pure monomers (e.g., pure diacetylene) or can comprise mixed monomers (e.g., PDA with Ganglioside $G_{M1}$ or dopant). Optimization of the percent composition of mixed monomers can be undertaken to provide biopolymeric material with desired properties. An example of such optimization is provided below for the detection of an analyte (i.e., cholera toxin) with a ganglioside ligand.

To evaluate the colorimetric response of $G_{M1}$/PDA films, different concentration combinations of ligand (i.e., $G_{M1}$) and PDA were tested. If too much ligand molecule was added (i.e., low concentration of polymerized lipid), the films were unstable and had high background. If the films had too much polymerized lipid molecule, they were too stable and the color change would not occur well. In search of the $G_{M1}$/PDA biosensor composition capable of displaying maximal response, a series of PDA monolayer films were transferred to OTS coated glass slides. The films were evaluated by exposure to cholera toxin and the colorimetric response was measured using UV-Vis spectroscopy. FIG. 21 summarizes the colorimetric properties and response of the $G_{M1}$ biosensing monolayer films studied in these experiments showing the initial absorbance, transfer rate, and colorimetric response in buffer and in response to analyte. The initial absorbance ($A_{init}$), which reflects the maximal peak value of the films at 640 nm, is a function of the film transfer rate and composition. $G_{M1}$, which does not provide chromatic functionality into the mixed assembly, generally decreases the intensity of the initial blue color. The transfer rate, which is the ratio of the area decreased on the tough surface and the area of the substrate emerged into the subphase, indicates that the PDA films are highly transferable as compared to those of sialic acid-PDA (SA-PDA) and $G_{M1}$ molecules. The blue to red colorimetric response (CR) shows that monolayer films exhibit low CR in buffer solution except when high content of $G_{M1}$ or SA-PDA is used.

II. Optimization of Subionic Phase

Figure 22:
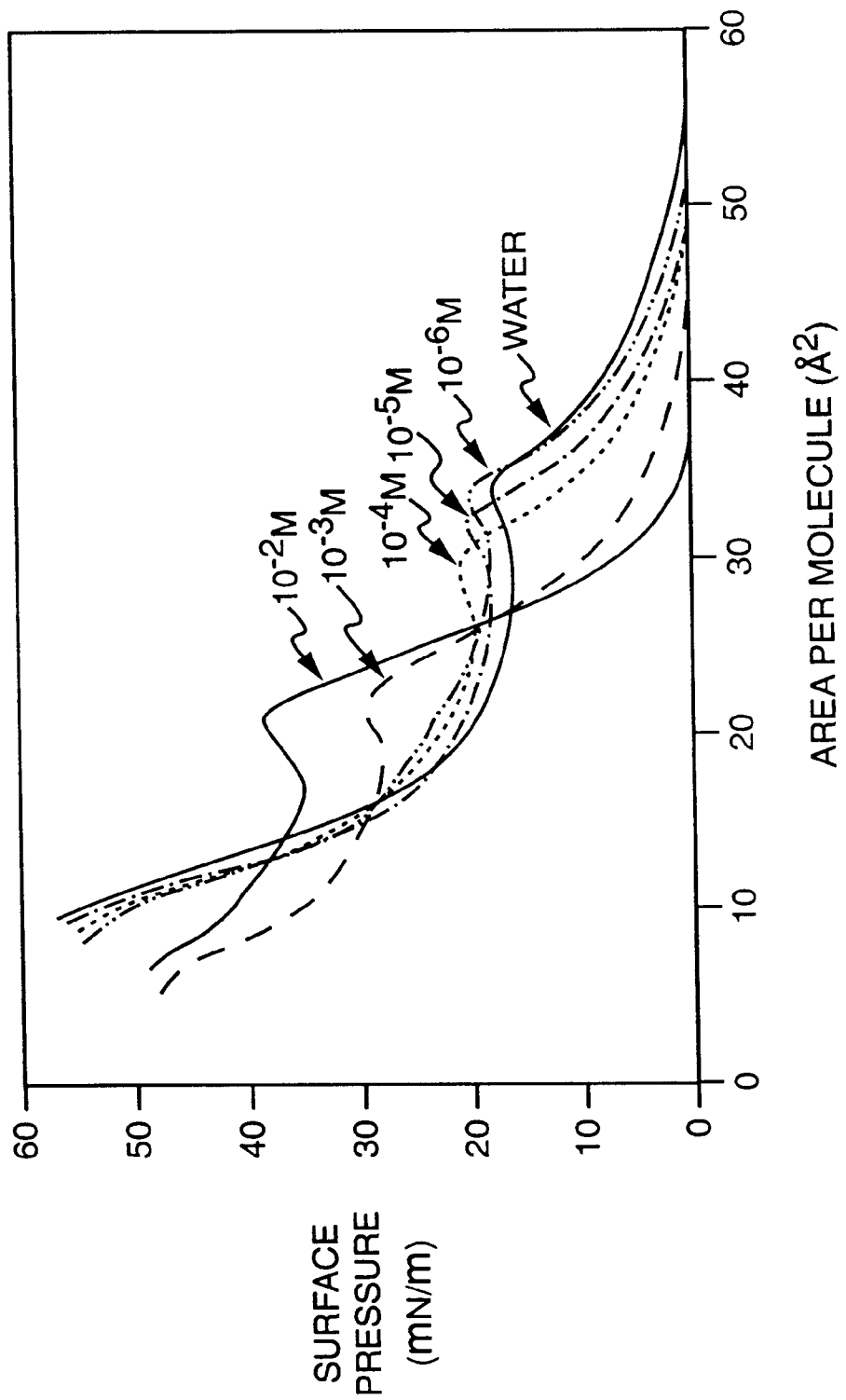
FIG. 22 shows the isotherms of 5% $G_{M1}$/5% SA-PDA/90% PDA as a function of subphase concentration of $CdCl_2$.

The ionic content of the aqueous subphase has significant impact on the properties of Langmuir monolayers. The presence of cationic species strengthens the electrostatic interaction of monolayer with anionic headgroups and consequently stabilized the film (Gaines, *Insoluble Monolayers at Liquid-Gas Interface*, Interscience Publishers, New York, pp 291–299 [1966]). FIG. 22 shows the isotherms of 5% $G_{M1}$/5% SA-PDA/90% PDA as a function of subphase concentration of $CdCl_2$. As the concentration of $Cd^{2+}$ is increased, the expanded phase shifts systematically toward the low molecular area, indicating that the monolayer is stabilized at high $Cd^{2+}$ concentration. This behavior results largely from the ionic interactions between $Cd^{2+}$ and partially dissociated anionic carboxylate headgroup of PDA (pKa≈5), while acidic SA-PDA and $G_{M1}$ (pKa≈2.6 for sialic acid on these molecules) probably also contribute to strengthen the effect. Further evidence for this mechanism of monolayer stabilization is seen in the increase in surface pressure as a function of higher ionic concentrations. Many divalent ions (Be, Mg, Ca, Ba, and Cd) have been shown to have an impact on the isotherms of PDA monomers through salt formation, which influences the packing of molecules on a basis of ion size and charge. No immiscible trend was observed for the ternary system of 5% $G_{M1}$/5% SA-PDA/90% PDA on aqueous subphases containing up to 0.01 M $Cd^{2+}$, indicating the this mixed monolayer is relatively stable as respect to ionic content. When $Cd^{2+}$ was increased to 0.1 M, however, erratic behavior of the 5% $G_{M1}$/5% SA-PDA/90% PDA monolayer was observed. This is possibly due to formation of aggregated domains as a result of different ability to interact with $Cd^{2+}$ between sialic acid in SA-PDA and $G_{M1}$ and carboxylic in PDA, or precipitation at high salt concentration.

At low $Cd^{2+}$ concentrations (i.e., approximately $10^{-4}$M), the isotherms differ very little in the condensed phase region, indicating that low ionic content in subphase has no significant effect on the structure of the compact films. Increasing the concentration of $Cd^{2+}$ above $10^{-3}$M, resulted in a shift of molecular area in the condensed phase region as shown in FIG. 22, pointing to some structural change in the compact monolayer. In order to explore the role of additives in the mixture for inducing such a structural change, an isotherm of pure PDA on $10^{-2}$M $Cd^{2+}$ was measured. On the $10^{-2}$M $Cd^{2+}$ subphase, a steep rise at low molecular area is seen in the isotherm of PDA. However, the slope of the isotherm within the compact region and the molecular area were essentially the same as on water. Such a result is consistent with an ordered film at high salt concentration, where the film characteristics are primarily dictated by the long hydrophobic segment of the molecules. Similar results were obtained for amine-based diacetylene (Walsh and Lando, Langmuir, 10: 252 [1994]). Therefore, the shift in FIG. 22 reflects a mixed electrostatic effect induced by differently dissociated individual components in the films, suggesting a lower stability of the ternary films as compared to the pure PDA films.

III. Optimization of Subphase pH

Figure 23:
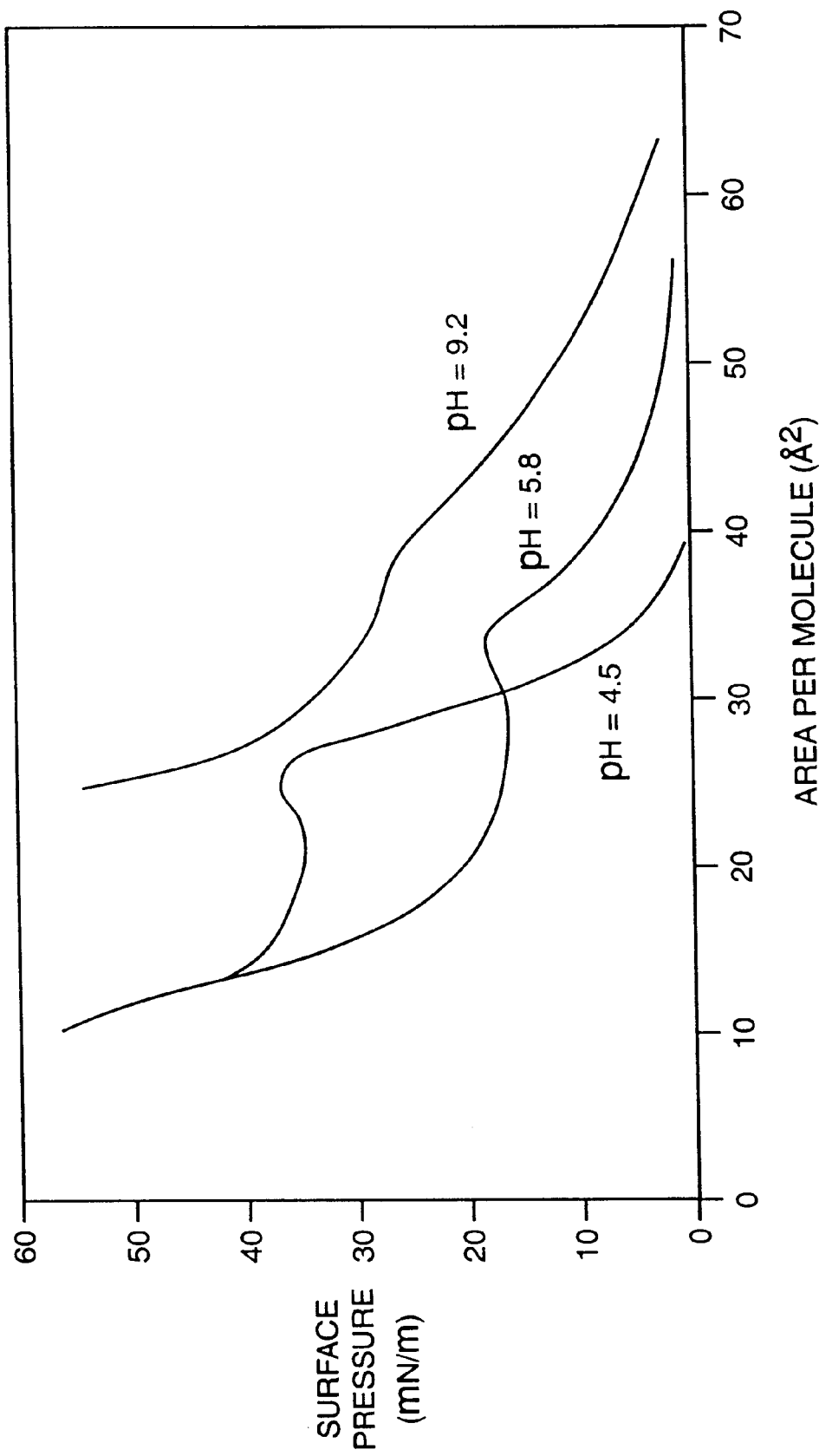
FIG. 23 shows the isotherms of 5% $G_{M1}$/5% SA-PDA/90% PDA at pH 4.5, 5.8, and 9.2.

For acidic molecule PDA, an increase in pH resulted in the ionization of PDA molecules and consequently introduced substantial charge along the monolayer interface. FIG. 23 shows the isotherms of 5% $G_{M1}$/5% SA-PDA/90% PDA at pH 4.5, 5.8, and 9.2. At high pH (pH 9.2), the film became very expanded as a result of electrostatic repulsion between the adjacent PDA molecules. Compression of such a film to form a monolayer was difficult. Additionally, distinct segments of individual molecules were observed, pointing to an immiscible trend in the mixed monolayer that tends to form segregated domains. Evidently, high charge density at the monolayer interface created unfavorable interactions on the aqueous surface. It can be expected that the addition of compounds such as $G_{M1}$ (i.e., which is acidic)

into the PDA mixture at this pH will be unfavorable. The isotherm of the ternary system at low pH exhibits normal peak behavior. The collapse pressure is significantly larger than at neutral pH, indicating a more stable film formed at low pH. Suppression of ionization of the PDA molecules at this pH contributes to the enhancement of film stability, which can consequently stabilize the incorporation of $G_{M1}$ molecules in the PDA films.

IV. Optimization of Subphase Temperature

Figure 24:
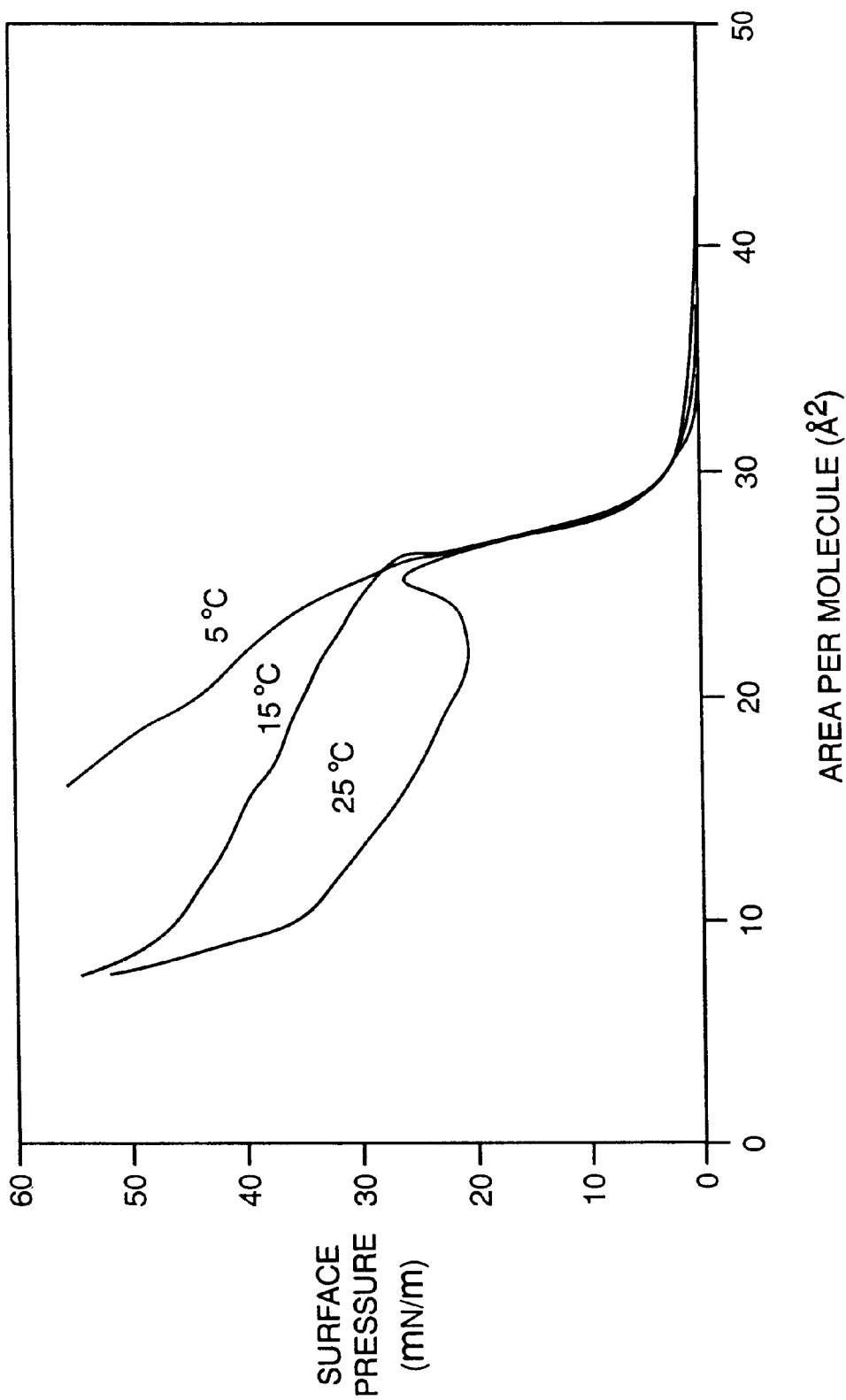
FIG. 24 shows the temperature effect on the isotherms of 100% PDA, 5%SA-PDA/95% PDA, and 5% $G_{M1}$/5% SA-PDA/90% PDA.

During film production, an increase in temperature usually results in higher surface pressure, an enlargement of the expanded region, and a shift in the phase transition point towards the low molecular area direction in $\pi/A$ isotherms (Birdi, *Lipid and Biopolymer Monolayers at Liquid Interfaces*, Plenum Press, New York [1989]). This effect stems from the higher flexibility of hydrocarbon tails of lipids at high temperature as a result of thermal agitation, and can be analyzed with the two-dimensional Clausius-Clapeyron equation (Birdi, supra). Monolayer films containing PDA, however, typically experience film collapse during compression. Consequently, the evaluation of the subphase temperature effect has to take this phenomenon into consideration. FIG. 24 displays the temperature effect on the isotherms of 100% PDA, 5%SA-PDA/95% PDA, and 5% $G_{M1}$/5% SA-PDA/90% PDA. With decrease in subphase temperature, the surface pressure increased and the isotherm shape changed. Isotherms at low temperature exhibited more and more liquid-solid phase transition features, as indicated by the disappearance of the peak and occurrence of the smooth curve at the transition region. All the $\pi$-A isotherms obtained for the three monolayers display similar characteristics. The major difference between these figures is the position of collapse point, which is a function of film composition.

V. Position of the Monomer Polymerizable Group

A comparison of the calorimetric responses of 10,12-pentacosadiynoic acid liposomes and 5,7-docosadiynoic acid (a gift from Alice Deckert of Holy Cross College) liposomes to analyte was conducted to determine the effect of the position of the polymerizable group within the self-assembling monomers. $G_{M1}$ ligands were incorporated into each type of liposome to analyze the detection of cholera toxin. The ganglioside $G_{M1}$ was mixed at 5 mol % with the diacetylene "matrix lipid" monomers. Liposomes were prepared using the probe sonication method and polymerized by UV irradiation (254 nm).

Figure 25:
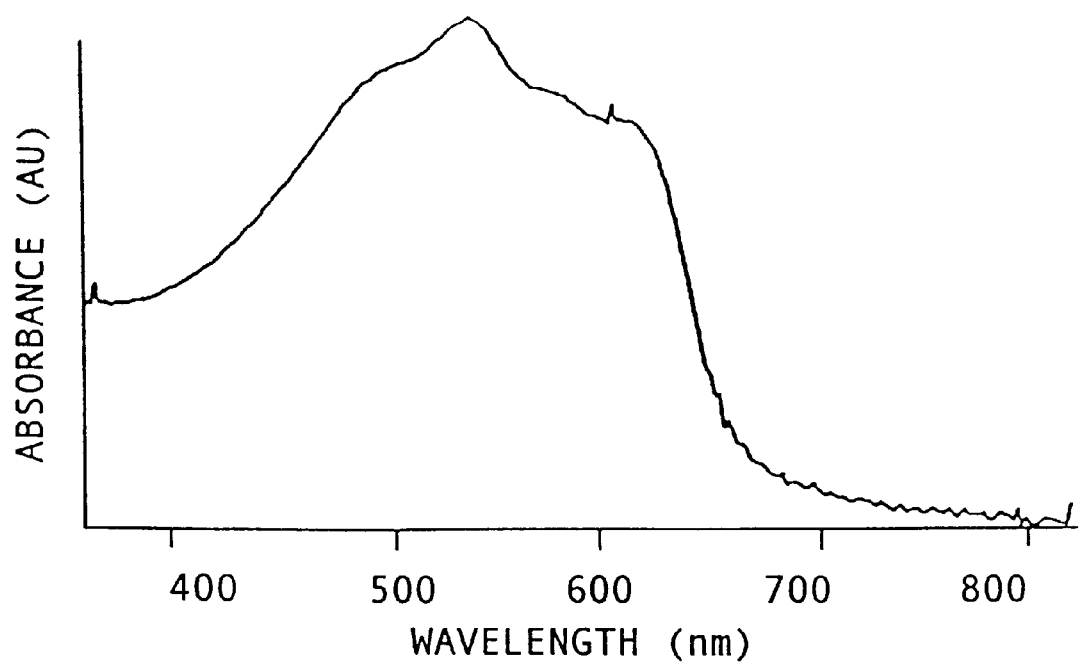
FIG. 25 shows the visible absorption spectrum of "blue phase" 5% $G_{M1}$ and 95% 5,7-docosadiynoic acid liposomes.
Figure 26:
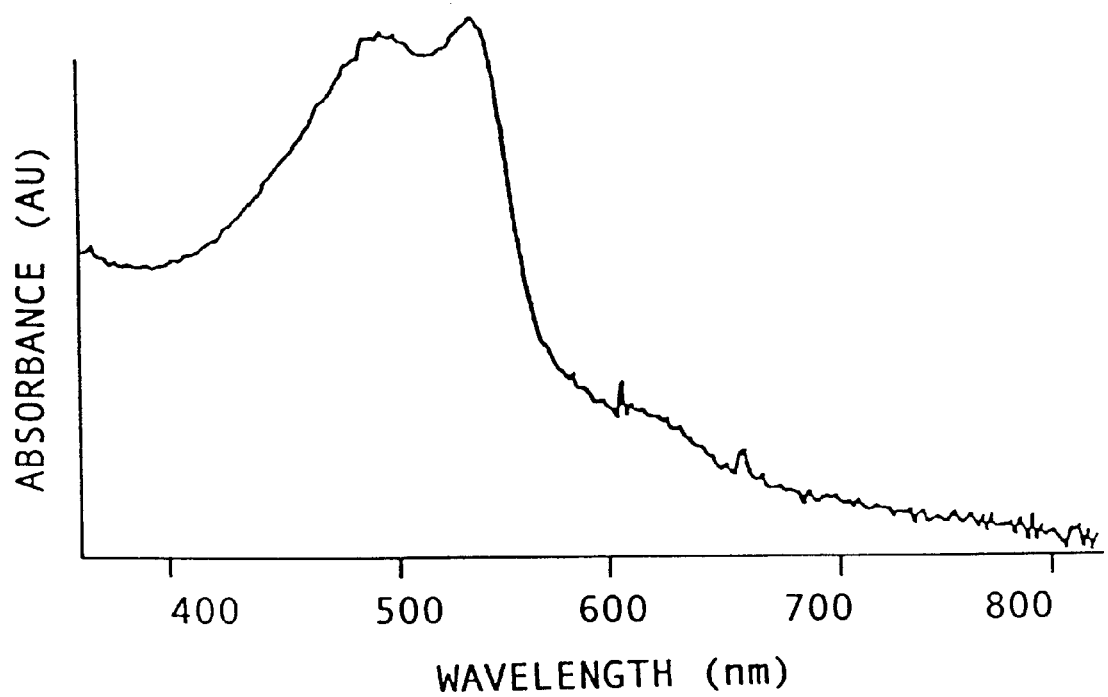
FIG. 26 shows the visible absorption spectrum of the liposomes of FIG. 25 following exposure to cholera toxin.

The conjugated ene-yne backbone of polydiacetylene liposomes resulted in the appearance of a deep blue/purple solution. The visible absorption spectrum of the freshly prepared purple liposomes is shown in FIG. 25. When cholera toxin was added to the liposomes composed of 5% $G_{M1}$ and 95% 5,7-docosadiynoic acid, the solution immediately changes to an orange color, and the "red phase" absorption of polydiacetylene dominates, as shown in FIG. 26. When the ganglioside $G_{M1}$ was mixed with a matrix lipid composed of 10,12-pentacosadiynoic acid instead of 5,7-docosadiynoic acid, the calorimetric response was significantly reduced. Although it is not necessary to understand the mechanism in order to use the present invention, and it is not intended that the present invention be so limited, it is contemplated that the enhanced sensitivity observed with the 5,7-docosadiynoic acid liposomes arises from the positioning of the optical reporter group nearer to the interface (i.e., three methylene units compared to eight). It has been shown by Fourier transform IR spectroscopy that small rotations about the C—C bond $\beta$ to the polymer backbone are sufficient to change the effective conjugated length (Berman et al., Science 259: 515 [1995]). These conformational changes are more easily transduced through shorter alkyl chain length.

EXAMPLE 4

Incorporation, Optimization, and Properties of Dopants

Each time a new sensor system is designed, the amount of PDA, dopant, and ligand (e.g., ganglioside) are varied to create the optimal sensor. Although 0–100% amounts are typically used for testing, optimal systems appear to use 5–15% ligands, 0–95% PDA, and 0–95% dopant. The percent of each component depends on the system, the needed stability, and the needed sensitivity. Certain embodiments of the present invention may incorporate more than one type of dopant into the biopolymeric material.

I. Incorporation of Dopant into Biopolymeric Material

Amino-acid derivatized diacetylene dopants were incorporated into colorimetric liposomes. The lipids (i.e., the dopants and the diacetylene monomers) were first dissolved in chloroform, and an aliquot was transferred to the reaction vial. The organic solvent was blown out by use of $N_2$ gas, and an appropriate amount of water was added to bring the lipid concentration to approximately 1 mM. Bath sonication was used to break down the white precipitate to form liposomes. Typical sonication times varied from 1 hour to 5 hours, dependent on the type of dopants used. During sonication, the temperature was carefully raised to approximately 80° C. to facilitate the formation of the liposomes. The sonication continued until the solutions became clear. The hot solutions were immediately filtered though a 5 $\mu$M Millipore Millex-SV filter to remove any impurity that may be present in the solution. The obtained solutions were stored at 4° C. overnight before use.

Following polymerization, deep blue colored liposomes were obtained. The final liposomes contained the amino-acid derivatized diacetylene dopant.

II. Optimization of Dopant Concentration

Films comprising PDA, $G_{M1}$ (i.e., the ligand) and sialic acid-derived PDA (i.e., the dopant) were generated as described in Example 3, Section I for the detection of cholera toxin. Colorimetric assays demonstrated that all three components were required for optimal colorimetric response. For the optimal detection of cholera toxin, both SA-PDA and $G_{M1}$ need be present in the films, otherwise the films are either too unstable or they do not change color well, depending on the concentration of all three components. Although it is not necessary to understand the mechanism in order to use the present invention, and it is not intended that the present invention be so limited, it is contemplated that the function of SA-PDA is to provide the metastable state of the films for biomolecular recognition through a stress-induced mechanism (Charych et al., Chem. and Biol. 3: 113 [1996]). A film consisting of 1% $G_{M1}$/1% SA-PDA/98% PDA was also investigated. The CR turned out to be low and it did not yield a useful colorimetric biosensor. As shown in FIG. 21, the optimal colorimetric sensor was determined to be 5% $G_{M1}$/5% SA-PDA/90% PDA. Thus, a 5% molar content of the dopant SA-PDA provides the best sensor for detection of cholera toxin.

III. Properties of Derivatized Diacetylene Dopants

Hydrophobic amino acids linked to diacetylenes can be used to lower the solubility of the biopolymeric material as well as the stability of the films or liposomes. These derivatized PDA's can be useful in the assembly of complex systems to fine tune the stability and sensitivity, two factors that are directly coupled to one another. Using the hydrophobic PDA's with the hydrophilic PDA's, the stability of films and liposomes can be greatly increased, under a variety of environmental conditions. Although a large gain in stability is seen, it is at a cost to sensitivity. A balance between sensitivity and stability has to be optimized.

Acidic and basic amino acids linked to diacetylenes can be used to increase the solubility of the material. Specifically, these changes allowed polydiacetylene lipids to mix with water soluble biological molecules. Ordinarily, PDA is not water soluble and organic solvents are necessary (i.e., which can be destructive to biological molecules). By placing acidic or basic head groups onto the PDA molecule, the solubility of the derivatized PDA's were greatly enhanced. They also produced much brighter colors and were more consistent in the assembly of sensors. These results were likely due to the increase in water solubility and homogeneity of mixing between all components. The acid/base PDA's were by far the most sensitive of the amino acid-derived diacetylenes.

Attaching histidine to amine-coupled PDA created materials that could easily turn color, but that could also be re-generated. The particular advantage to this approach is that ordinarily polymerized PDA's turn color, but cannot be used again. The near-neutral pKa of the head group of the histidine materials allows for this advantage.

By placing fluorescent PDA head groups onto the PDA amine-coupled system, colorimetric biosensors can be made with the addition of fluorescent properties. This provides a multi-purpose and more sensitive sensor.

EXAMPLE 5

Attachment of Ligands

Ligands can be covalently linked to the head groups of self-assembling monomers (e.g., sialic acid linked to diacetylene monomers), can be covalently linked to the surface of polymerized materials (e.g., proteins and antibodies with multiple amine and thiol linkages to the material surface), or can be non-covalently incorporated into the biopolymeric material (e.g., ganglioside incorporated into the membrane of films and liposomes).

The self-assembling monomers can be synthesized to contain a large variety of chemical head-group functionalities using synthesis techniques common in the art. In some embodiments, the ligands are then joined to the self-assembling monomers through chemical reaction with these functionalities using synthesis methods well known in the art. The functionalities include, but are not limited to, esters, ethers, amino, amides, thiols, or combinations thereof Alternately, many ligands can be incorporated into the self-assembling matrix without covalent linkage to the surfactants (e.g., membrane proteins and molecules with hydrophobic regions such as gangliosides and lipoproteins).

Specific applications of the present invention are described below to illustrate the broad range of ligands that can be associated with the inventive biopolymeric material. These examples are intended to merely illustrate the broad applicability of the present invention and are not intended to limit the present invention to these particular embodiments.

I. Sialic Acid

Sialic acid was attached as a ligand to diacetylene monomers. Several synthesis methods well known in the art can be used, many of which have general applicability to the attachment of carbohydrates to the inventive biopolymeric materials. In one embodiment, PDA (1.0 g, 2.7 mmol in chloroform) was reacted with N-hydroxy succinimide (NHS) (0.345 g, 3.0 mmol) and 1-(3-dimethylaminopropyl)-3-ethylcarbodiimide hydrochloride (EDC) (0.596 g, 3.1 mmol). The solution was stirred for 2 hours followed by evaporation of the chloroform. The residue was extracted with diethyl ether and water. The organic layer was dried with magnesium sulfate ($MgSO_4$) and filtered. The solvent was then evaporated by rotary evaporation to give 1.21 g of N-succinimidyl-PDA (NHS-PDA). Ethanolamine (0.200 ml, 2.9 mmol) was added to a solution of NHS-PDA (1.21 g in 50 ml of chloroform), followed by triethylamine (0.350 ml, 2.5 mmol) and stirred for two hours at room temperature. The solvent was evaporated and the residue purified by silica gel chromatography (2:1 EtOAc:hexane, $R_f$=0.15) to give 0.99 g of N-(2-hydroxyethyl)-PDA.

Tetraethylene glycol diamine (1.26 g, 6.60 mmol) in 25 ml of chloroform was added to a solution of N-succinimidyl-PDA (0.603 g, 1.28 mmol) in 20 ml of chloroform, dropwise, with stirring, over a period of 30 minutes. The reaction was stirred for an additional 30 minutes before removal of the solvent by rotary evaporation. The residue was dissolved in EtoAc and extracted twice with water. The organic layer was dried with $MgSO_4$, and the solvent removed by rotary evaporation. The extract was purified by silica gel chromatography (20:1 $CHCl_3$:MeOH, $R_f$=0.20) to give 3.72 g of N-(11-amino-3,6,9-trioxyundecanyl)-PDA.

Two ml of acetic anhydride was added to a cooled solution of ethyl-5-N-acetyl-2,6-anhydro-3,5-dideoxy-2-C-(2-propenyl)-D-erythro-L-mannonononate (0.47 g, 1.30 mmol) in 1.7 ml of pyridine under nitrogen, with stirring. The reaction was allowed to warm to room temperature overnight. After 18 hours, the solvents were removed under reduced pressure at ambient temperature, to yield a crude viscous oil. The oil was solidified by repeated evaporation from toluene. The crude solid was flash chromatographed over silica with ethylacetate as eluent, producing 0.58 g of ethyl-5-N-acetyl-4,7,8,9-tetra-O-acetyl-3,5-dideoxy-2-C-(2-propenyl)-D-erythro-L-manno-nononate.

A solution of ethyl-5-N-acetyl-4,7,8,9-tetra-O-acetyl-3,5-dideoxy-2-C-(2-propenyl)-D-erythro-L-manno-nononate (0.38 g, 0.72 mmol) in 10 ml of acetone was cooled to −78° C. while protected from moisture with a $CaCl_2$ drying tube. Ozone was aspirated into the solution until the characteristic blue color persisted for 5 minutes. The reaction was purged with $O_2$ to dissipate the excess $O_3$, followed by warming to 5° C. Excess Jones' reagent (7 drops) was added until a rust orange color persisted, then the reaction was warmed to ambient temperature. After several minutes, ethanol was added dropwise to consume the excess oxidant. The green precipitate was filtered and washed with acetone several times. The combined filtrates were evaporated in vacuuo and dissolved in ethylacetate. The solution was extracted with saturated aqueous $NaHCO_3$ solution three times. The combined aqueous layers were acidified with concentrated HCl and extracted 5 times with methylene chloride. The combined methylene chloride extracts were dried with $MgSO_4$, filtered and evaporated in vacuuo to give ethyl-5-N-acetyl-4,7,8,9-tetra-O-acetyl-3,5-dideoxy-2-C-(acetic acid)-D-erythro-L-manno-nonate.

Ethyl-5-N-acetyl-4,7,8,9-tetra-O-acetyl-3,5-dideoxy-2-C-(acetic acid)-D-erythro-L-manno-nonate (0.194 g, 0.35 mmol) was added to a cooled solution (5° C.) NHS (0.058 g, 0.50 mmol) and EDC (0.096 g, 0.50 mmol) in 2 ml of chloroform, under nitrogen. The reaction was warmed to ambient temperature with stirring for 5 hours. The reaction was then diluted with 15 ml of chloroform and washed with 1 N HCl (aq.), twice; saturated (aq.) sodium bicarbonate, twice; and saturated (aq.) sodium chloride, once. The organic layer was dried over MgSO$_4$, filtered, and evaporated to form ethyl-5-N-acetyl-4,7,8,9-tetra-O-acetyl-3,5-dideoxy-2-C-(N-succinimidylacetate)-D-erythro-L-manno-nononate.

Ethyl-5-N-acetyl-4,7,8,9-tetra-O-acetyl-3,5-dideoxy-2-C-(N-succinimidylacetate)-D-erythro-L-manno-nononate (0.143 g, 0.22 mmol) and N-(11-amino-3,6,9-trioxyundecanyl)-PDA (0.133 g, 0.24 mmol) were dissolved in 2 ml of chloroform and the reaction was sealed and stirred for 56 hours. The solution was diluted with 15 ml of chloroform and washed with sodium chloride saturated 1N HCl (aq.), twice; saturated (aq.) sodium bicarbonate, twice; and saturated (aq.) sodium chloride, once. The organic layer was dried over MgSO$_4$, filtered, and evaporated to a crude semi-solid. The material was flash chromatographed over silica (20:1 CHCl$_3$:MeOH), producing ethyl-5-N-acetyl-4,5,8,9-tetra-O-acetyl-3,5-dideoxy-2-C-[(N-11'-(PDA)-3',6',9'-trioxyundecanyl) acedamido]-D-erythro-L-manno-nononate.

The sialic acid derived-PDA was formed by dissolving ethyl-5-N-acetyl-4,5,8,9-tetra-O-acetyl-3,5-dideoxy-2-C-[(N-11'-(PDA)-3',6',9'-trioxyundecanyl) acedamido]-D-erythro-L-manno-nononate (0.20 g, 0.19 mmol) in a solution of 4 ml of water and 0.5 ml of methanol containing 0.1 g dissolved sodium hydroxide. The solution was stirred for 3 hours, and ion exchange resin (Biorad AG 50W-X4 H+ form) was added until the solution was acidic to pH paper. The solution was filtered and the filtrate evaporated in vacuo, producing sialic acid derived-PDA.

II. Carbohydrates

In other embodiments of the invention, carbohydrates (i.e., including sialic acid) can be modified by a three-step procedure to produce N-allyl glycosides. For example, the N-allyl glycosides can then be easily linked to other molecules (e.g., PDA) using simple chemical synthesis methods known in the art. This method provides a means to incorporate a broad range of carbohydrates into biopolymeric material (and thus provides a means to detect a broad range of analytes). First, oligosaccharides are dissolved in neat allyl amine (water may be added if necessary and does not adversely affect the yield) producing a 0.5–0.1 M solution. The reaction is stopped and stirred for at least 48 hours. Upon complete conversion of the starting material into amino glycoside product, the solvent is removed by evaporation and the crude solid is treated with toluene and evaporated to dryness several times. The solid is then chilled in an ice bath and a solution of 60% pyridine, 40% acetic anhydride is added to give a solution containing five hundred mole percent excess of acetic anhydride. The reaction is protected from moisture, stirred and allowed to warm to ambient temperature overnight. The solvents are removed by evaporation and the residue is dissolved in toluene and dried by evaporation several times. The crude product is purified by flash chromatography producing the peracetylated NAc-allyl glycoside form of the free sugars.

The peracetylated NAc-allyl glycosides are then dissolved in anhydrous methanol to give a 0.1–0.01 M solution. Several drops of 1 N NaOMe in MeOH are added and the reaction stirred at ambient temperature for 3 hours. Enough Dowex 50 resin (H+ form) is added to neutralize the base, then the solution is filtered and evaporated to dryness (purification by recrystallization can be conducted if desired). The products are the N-allyl glycoslamide form of the carbohydrates. These synthesis reactions have produced the N-allyl glycoslamide forms of a variety of carbohydrates, including, but not limited to, glucose, NAc-glucosamine, fucose, lactose, tri-NAc-Chitotriose, Sulfo Lewis$^x$ analog, and Sialyl Lewis$^x$ analog. Skilled artisans will appreciate the general applicability of this method to the attachment of a broad range of carbohydrates to diacetylene lipids.

III. Ganglioside $G_{M1}$

Ganglioside $G_{M1}$ presents an example of incorporation of a ligand without covalent attachment to the self-assembling monomers. Ganglioside $G_{M1}$ was introduced in the biopolymeric material by combining a solution of methanol dissolved ganglioside $G_{M1}$ (Sigma) with chloroform dissolved PDA, and dried. The ganglioside contains a hydrophobic region that facilitates its incorporation into self-assembling surfactant structures. Thus, when the dried solutions were resuspended in deionized water, the resulting structures contained a mixture of ganglioside and PDA. Liposomes and other forms were produced from the resuspended mixture as described in Example 1. Although the ganglioside does not contain a polymerizable group, the ganglioside became embedded in the polymerized matrix created by the cross-linking of the diacetylenes. Similar methods can be used for the incorporation of other ligands that contain hydrophobic regions (e.g., transmembrane proteins and lipoproteins).

IV. Proteins

The NHS-PDA, as generated above, thiol-linked PDA, and other methods known in the art provide functional groups for the attachment of proteins and antibodies. The NHS or thiol-linked monomers are incorporated into the desired aggregate and polymerized. The NHS or thiol functional groups then provide a surface reaction site for covalent linkage to proteins and antibodies using chemical synthesis reactions standard in the art. In another embodiment, a hydrazide functional group can be placed on PDA, allowing linkage to aldehydes and ketone groups of proteins and antibodies. These embodiments provide a means to incorporate an extremely broad array of proteins and antibodies onto the biopolymeric material. Specific examples are provided below. These examples are intended to merely illustrate the broad applicability of the present invention and are not intended to limit the present invention to these particular embodiments.

A. Hexokinase

NHS-PDA lipid was synthesized as described above. In brief, 1.00 g 10,12-pentacosadiynoic acid (Farchan, Gainesville, Fla.) was dissolved in CHCl$_3$, to which 0.345 g N-hydroxysuccinimide (NHS) and 0.596 g 1-(3-dimethylaminopropyl)-3-ethylcarbodiimide hydrochloride were added. The solution was stirred at room temperature for two hours, followed by removal of CHCl$_3$ using a rotavap. The residue was extracted with EtOAC and water. After separation, the organic layer was dried with MgSO$_4$ and filtered, followed by solvent removal. The raw product was then recrystallized twice with CHCl$_3$, and confirmed by FT-IR.

The 1:1 (molar ratio) PDA/NHS-PDA chloroform solution was spread on the aqueous subphase on a Langmuir-Blodgett trough (KSV mini-trough, KSV Instruments, Inc., Finland) by using a microsyringe (subphase temperature was maintained at 5° C.). The organic solvent was allowed to evaporate by resting the solution for 20 min. The films were compressed to compact monolayer level and then transferred by vertical deposition to glass slides coated with octadecyltrichlorosilane (OTS). The compression and dipping speed was maintained at 5 mm/min. Three layers were deposited onto the glass slide to provide enough colorimetric signal for detection after polymerization and to ensure the hydrophilic surface was exposed to solution.

The preparation of stable PDA monolayer films before enzyme immobilization is critical for low background and enhanced reproducibililty of the sensors. The Langmuir monolayer trough provides a method to measure film stability through the evaluation of the surface collapse pressure of the monolayers. It was found that the mixed films (i.e., films with PDA and NHS-PDA) appear to be much more stable than the monolayers consisting of one component and thus more suitable for enzyme immobilization. For instance, the collapse pressure for 1:1 NHS-PDA/PDA monolayer at 5° C. was 57 mN/m, while NHS-PDA and PDA monolayers collapsed at 34 and 28 mN/m, respectively. Although it is not necessary to understand the mechanism in order to use the present invention, and it is not intended that the present invention be so limited, it is contemplated that the interactions are more favorable in these mixed monolayers, presumably due to the optimal spatial arrangements that allow head groups of different size to pack closely.

Besides mechanical stability, the monolayers should possess desirable optical properties (i.e., high color intensity) to be suitable as sensors. Film quality, in this particular case color intensity, was studied at different deposition pressures. It was found that films made at 40 mN/m gave the best transfer rate and color intensity. Therefore, the 1:1 NHS-PDA/PDA films obtained at this transfer pressure were selected for modification with hexokinase.

Yeast hexokinase suspension (E.C. 2.7.1.1, from Boehringer Mannheim GmbH, Germany) was spun in a microcentrifuge to remove saturated ammonium sulfate. The protein was resolubilized in 0.1 M phosphate buffer (pH 8.0) to give approximately 1 mg/ml concentration, and dialyzed against the same buffer using a Slide-A-Lyzer dialysis cassette (Pierce) for 3 hours. The PDA monolayer slides were cut into 0.7 cm×2.5 cm rectangular pieces, and incubated in the hexokinase solution at 4° C. for 1 hr. Prolonged incubation was found to result in decreased color intensity, presumably due to the shedding of LB monolayers during the chemical cross-linking reaction. The monolayer chips were then rinsed with deionized water and immersed into 0.1 M ethanolamine for 10 min to terminate the reaction. The chips were rinsed again with deionized water and air dried. Polymerization was conducted by irradiating the films with a hand held IV lamp. The irradiation time was 6 min. each side. Extended irradiation results in irreversible color change to red.

B. Antibodies

Commercially obtained diacetylene was first filtered to remove the insoluble impurities (e.g., polymerized form) and converted chemically to NHS-PDA as described above. Appropriate amounts of NHS-PDA and other forms of PDA derivatives (e.g., dopants or ligands) were mixed to give the desired molar ratio. The solution was dried using $N_2$ gas, so a thin layer of white material deposited on the bottom of the vial. Deionized water was added to bring the total concentration of lipid to approximately 1 mM. The solution was sonicated by using either a probe sonicator for approximately 20 minutes or a bath sonicator for over 2 hours until a clear solution was obtained. The solution was filtered through 5 $\mu$m filter while hot, then stored at 4° C. overnight.

Prior to cross linking, 0.1 M phosphate buffer (pH 8.5) was added to the liposome solution. Antibody dissolved in a similar buffer was then added, and the solution was stored at 4° C. overnight. Excess antibody was removed by either centrifugation or dialysis. When centrifugation was used, the pellet was resonicated gently using an ice bath. Following association of the antibody to the sonicated material, polymerization was conducted as described for liposomes in Example 1.

Antibodies can also be attached to biopolymeric material by hydrazides. In some embodiments, this may be preferred to NHS-coupling because NHS may react at the Fab' region of the antibody, blocking binding to analytes. The hydrazide method causes attachment of the Fc region of the antibodies to the biopolymeric material, leaving available, the binding region. In the hydrazide method, hydrazide-PDA lipids were produced, and unpolymerized liposomes are generated (e.g., 20% hydrazide PDA/80% TRCDA). Using Centricon 50 filters, 500 $\mu$l of stock antibody solution was washed by adding an equal volume of 123 mM sodium citrate (pH 5.5) and spun down at 4000 rpm for 9 minutes. The filtering step was repeated two more times. Four hundred microliters of the antibodies in citrate buffer were then oxidized by incubating with 25 $\mu$l of sodium periodate for 2 hours at 22° C. After the 2 hours, the reaction was quenched by adding 50 $\mu$l of N-acetylmethionine. Next, 300 $\mu$l of liposomes, 150 $\mu$l citrate buffer, 400 $\mu$l water, and 200 $\mu$l of oxidized antibodies were incubated overnight at 22° C. Uncoupled antibodies are removed from the liposomes by using Centricon 500 filters and washing with 900 $\mu$l Tris buffer (pH 9.0) and centrifugation at 4000 rpm for 2 minutes. After multiple washes, the sample is dilute (if necessary) with Tris buffer to make a 0.2 mM (or less) liposome solution.

V. Others (Amino Acids, Nucleotides, Etc.)

Figure 9:
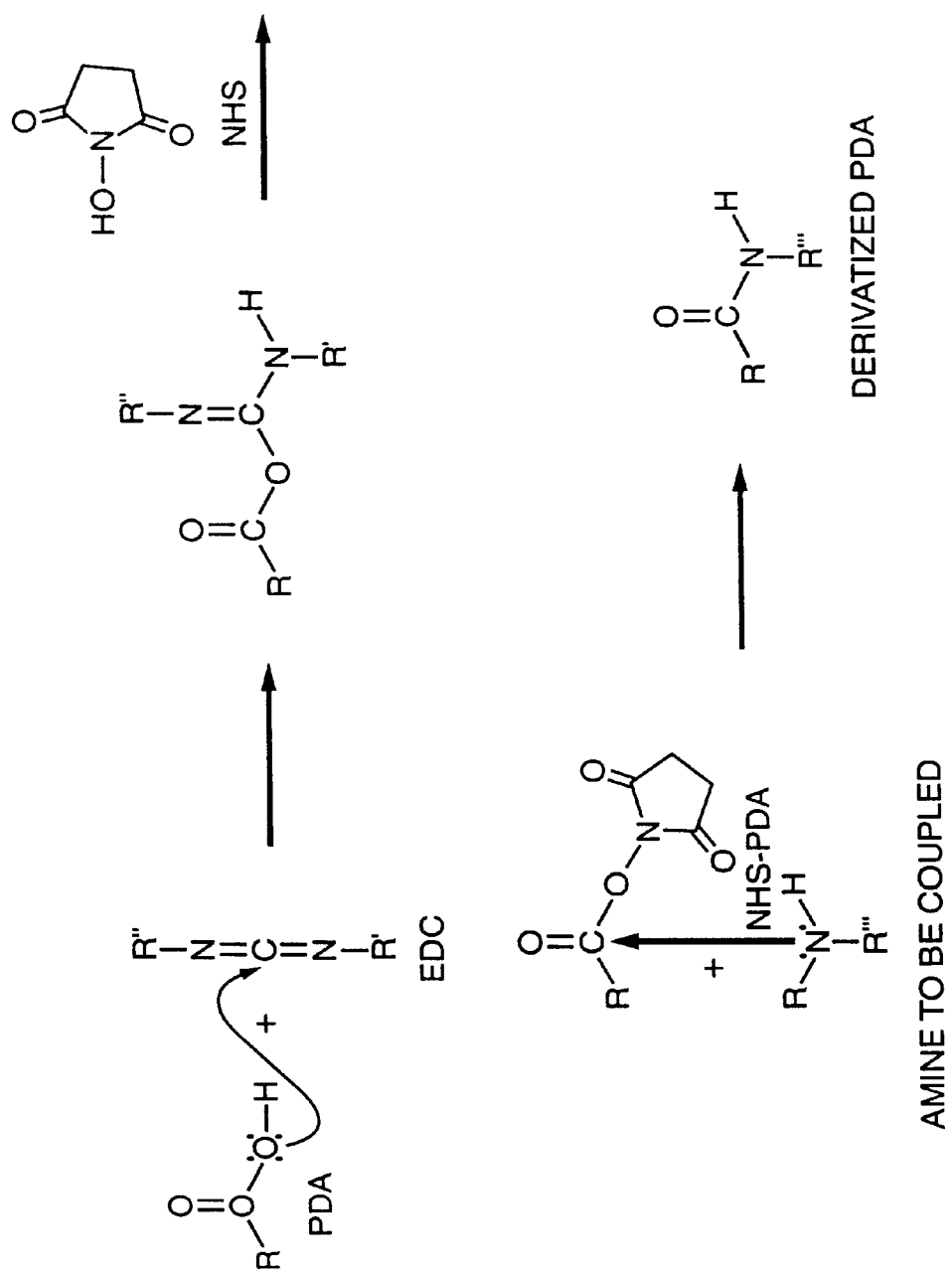
FIG. 9 shows a synthesis reaction for modifying the free amino group of a molecule for coupling to a lipid monomer.
Figure 10B:
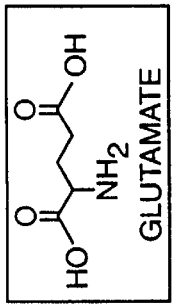
FIG. 10B shows the properties of additional biopolymeric materials composed of amino acid-derivated diacetylene monomers.
Figure 11:
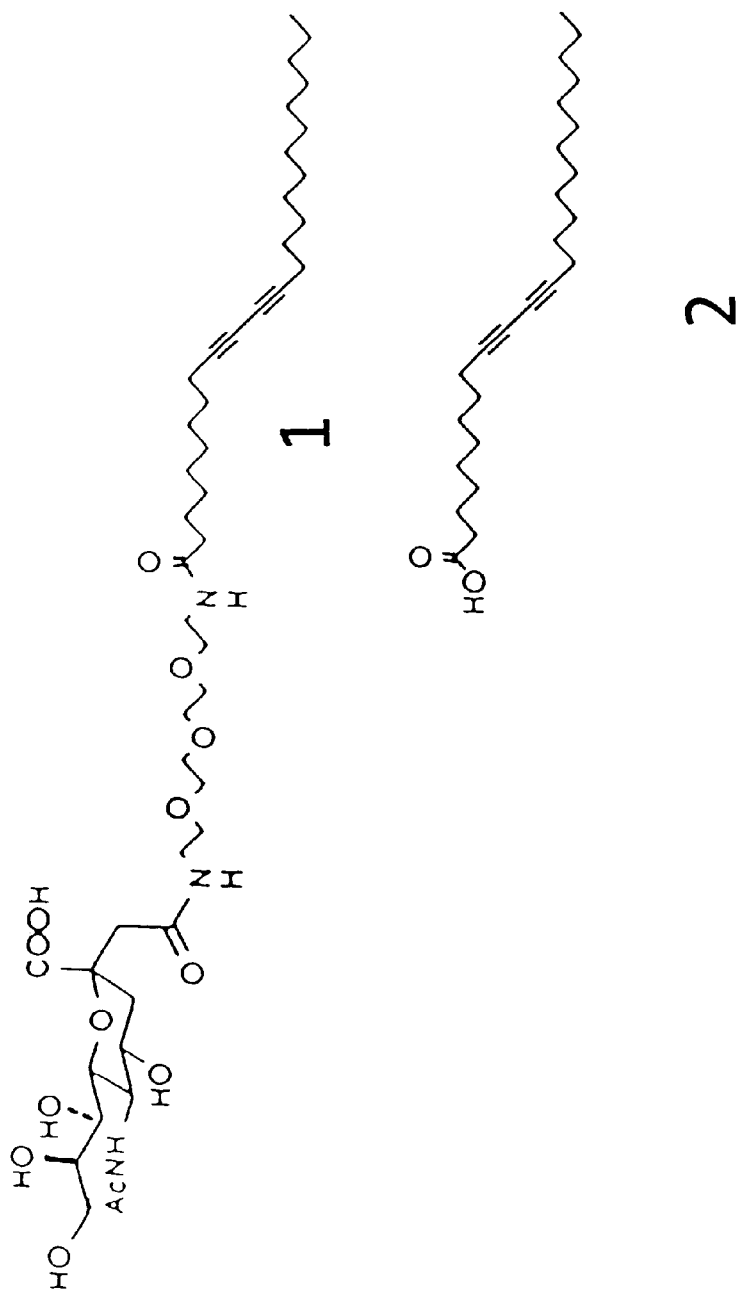
FIG. 11 shows the chemical structure of sialic acid derived 10,12-pentacosadiynoic acid (compound 1) and 10,12-pentacosadiynoic acid (compound 2).

As described above and shown in FIG. 9, the attachment of amino acids though amine linkage to diacetylenes has been accomplished. A variety of other means of attaching amino acids to lipids are also known in the art.

The generation of PDA-linked ligands containing a variety of different chemical head-group species is described in Example 7, for VOC detection. These examples demonstrate the derivation of PDA with a broad range of chemical head groups such as hydrophilic uncharged hydroxyl groups, primary amine functionalities, amino acid derivatives, and hydrophobic groups. These and other modifications are generated by synthesis methods known in the art.

In other embodiments, various other surfactant-linked ligands can be prepared using condensation reactions involving an activated carboxylic acid group and a nucleophilic amino or hydroxy. PDA can be activated with trimethylacetylchloride under anhydrous conditions to form an active asymmetric anhydride. The anhydride can be treated with excess ethylene diamine or ethanolamine to form ethylenediamino-PDA (EDA-PDA) or ethanolamine-PDA (EA-PDA), respectively. One and a half mole equivalents of triethylamine are added as a catalytic base and reactions are allowed to proceed for three hours at room temperature. EDA-PDA and EA-PDA are chromatographically purified using a silica gel column and a chloroform/methanol gradient. The EDA-PDA or EA-PDA are then be condensed with free carboxylic acid containing ligands (chemically activated as above) to form the ligand-linked polymerizable surfactants. Representative examples of ligands that can be prepared by this method include, but are not limited to, carbohydrates, nucleotides, and biotin.

The art contains numerous other examples of successful linkage or association of molecules to lipids and membranes. The self-assembling monomers associated with ligands can be of modified chain length or may consist of double or multiple chains. These various combinations of ligands and monomers provide an extremely broad array of biopolymeric materials appropriate for the interaction with a broad range of analytes, with the desired colorimetric response, selectivity, and sensitivity.

In one embodiment of the present invention, the hydrazide of PDA was synthesized by treatment of NHS- PDA with hydrazine hydrate. Hydrazine hydrate (500 µl, ~80%) was mixed with NHS-PDA solution (1 mL, 40 mg ml$^{-1}$ in $CH_2Cl_2$), and reacted at room temperature for 12 h. The organic phase was then exhaustively extracted with $H_2O$ and rotavaped to dryness, yielding quantitatively pure PDA-NH—$NH_2$ as one spot on TLC ($CH_2/Cl_2$/MeOH/$NH_3$ aq. 13:6:1, $R_f$=0.94). Characterization: white solid, $^1$H-NMR (200 MHz, $CDCl_3$): δ [ppm]=0.87 (t, J=6.42 Hz, 3 H, —$CH_3$), 1.25 (br. s, 32 H, alkyl—$CH_2$—), 2.14 (t, J=7.52 Hz, 2 H, —$CH_2$—$CH_2$—CO—NH—), 2.23 (t, J=6.87 Hz, 4 H, —$CH_2$—C≡C—C≡C—$CH_2$—), ~3.3 (br. s, 2 H, —NH—$NH_2$), 6.75 (s, 1 H, —CO—NH—$NH_2$); IR (KBr): ν~[cm$^{-1}$]=3310 (s, ν(—$NH_2$)), 2918 (s, ν($CH_2$)), 2851 (s, ν($CH_2$)), 1645 (s, ν(C=O)), 1606 (s, δ(>CON—H)), 1534 (m, amid II), 1471 (m), 1422 (m), 1263 (w), 1012 (w), 976 (w), 716 (w), 691 (w), 583 (w). IR spectroscopy of PDA-NH—NH2 (KBr) showed a strong peak at 3310 cm$^{-1}$, which was characteristic of an amino group. The carbonyl stretch vibration of PDA at 1600 cm$^{-1}$ was replaced by three amide bands (1645, 1606, 1534 cm$^{-1}$). These bands can be very useful for IR studies of H-bonding in PDA-NH—$NH_2$ layer systems.

In one embodiment of the present invention, mixed liposomes (0.1 mM) composed of 95% PDA and 5% PDA-NH—$NH_2$ were polymerized with 0.3 J cm$^{-2}$. These liposomes posses the same polymerization behavior as pure PDA liposomes and could be easily used for binding studies with keto-modified cells, aldehydes, ketones or NHS-esters. Although an understanding of the mechanism is not necessary to practice the present invention, and the present invention is not limited to any particular mechanism, liposomes made from pure PDA-NH—NH2 surprisingly did not polymerize in pure $H_2O$. After irradiating a 0.1 mM liposome solution in $H_2O$ with 0.9 J cm$^{-2}$, only a very weak red absorption was observed. The same lack of polymerization was seen when irradiating the liposomes in basic medium (i.e., 90 mM $NH_3$: PHY02 or carbonate buffer pH 9: PHY03). In contrast, liposomes (0.1 mM) polymerized in high yield straight to the red form in a 90 mM HCl solution. By increasing the HCl concentration to 0.9 M the liposomes polymerized in excellent yield to the blue form. This solution was not stable over time and the liposomes precipitated. When these blue liposomes were treated with slight excess of base (i.e., $NH_3$) the color changed to red. Upon addition of HCl the color reversed to blue again. A similar effect of pH on formation of a specific color phase was also observed with $NH_3$-treated PDA samples.

This reversible calorimetric transition was thought to be due to altered H-bonding in the head group region, although an understanding of the mechanism is not necessary to practice the present invention, and the present invention is not limited to any particular mechanism. It is likely that H-bonding strongly governs molecular packing of the lipid chains, and imposes conformational changes onto the conjugated polymer backbone.

EXAMPLE 6

Colorimetric Analysis

1. Visual Detection

In preferred embodiments, the calorimetric changes of the biopolymeric materials of the present invention are detected though simple observation by the human eye. Because of the simplicity of the observation, this function can be accomplished by an untrained observer such as an at-home user. This Example provides a description of the methods used in the development of the colorimetric analyses of the present invention.

II. Visible Absorption Spectroscopy

In some embodiments it may be preferred to obtain accurate quantitative data of the colorimetric responses or to record subtle changes or faint signals undetectable by the human eye. Spectroscopy means may be applied to acquire such data.

Visible absorption studies were performed using a Hewlett Packard 8452A Diode array spectrophotometer. For PDA material (i.e., films and liposomes), the calorimetric response (CR) was quantified by measuring the percent change in the absorption at 626 nm (i.e., which imparts the blue color to the material) relative to the total absorption maxima.

In order to quantify the response of a biopolymeric material to a given amount of analyte, the visible absorption spectrum of the biopolymeric material without the analyte was analyzed as $$B_o = I_{626}/(I_{536}+I_{626})$$

where $B_o$ is defined as the intensity of absorption at 626 nm divided by the sum of the absorption intensities at 536 and 626 nm. The biopolymeric material exposed to analytes were analyzed in the same manner as $$B_a = I_{626}/(I_{536}+I_{626})$$

where $B_a$ represents the new ratio of absorbance intensities after incubation with the analyte. The colorimetric response (CR) of a liposome solution is defined as the percentage change in B upon exposure to analyte.

$$CR = [(B_o - B_a)/B_o] \times 100\%$$

EXAMPLE 7

Detection of Analytes

The broad range of biopolymeric materials taught by the present invention allow for the detection of numerous analytes. Such analytes range from complex biological organisms (e.g., viruses, bacteria, and parasites) to simple, small organic molecules (e.g., alcohols and sugars). Specific applications of the present invention are described below to illustrate the broad applicability of the invention to a range of analyte detection systems and to demonstrate its specificity, and ease of use. These examples are intended to merely illustrate the broad applicability of the present invention. It is not intended that the present invention be limited to these particular embodiments.

I. Detection of Influenza Virus

The present invention provides superior means of detecting influenza compared to currently available technology. Immunological assays are limited because of the antigenic shift and drift exhibited by the virus. The present invention detects all varieties of influenza and thus a determination of a patient's exposure to influenza will be definitive, and not limited to a particular strain. Indeed, even newly evolved, uncharacterized influenza strains can be detected.

Sialic acid-linked biopolymeric material was generated as described in Examples 1 and 5. The materials were exposed to influenza virus and calorimetric information was observed visually or with spectroscopy as described in Example 6, and shown in FIG. 27 for blue (solid line) and red phase (dashed line) material, respectively. For liposomes, a 1–10% mixture of sialic acid-linked PCA was incorporated, as previous studies indicated that optimum viral binding occurs for mixtures of 1–10% in liposomes (Spevak et al., J. Am. Chem. Soc. 161: 1146 [1993]).

For silicate glass-entrapped liposomes (i.e., liposomes prepared by the sol-gel method), it was found that 5,7-DCDA provided a more vivid colorimetric response than 10,12-PCA. It is believed that the improved response with 5,7-DCDA was related to the size restrictiveness of the sol-gel material and the topochemical nature of the conformational changes responsible for the chromatic transitions, although an understanding of the mechanism is not required to practice the present invention.

In one experiment, irradiation of a sialic acid-linked PCA containing liposome solutions for 5–10 minutes resulted in the formation of deeply blue colored liposomes, while polymerization for between 10 and 30 minute resulted in a purple color. When influenza virus was added to the liposomes, the material changed to a pink or orange color, depending on whether the initial preparation was blue or purple, respectively. These color changes were readily visible with the naked eye.

Competitive inhibition experiments were conducted to demonstrate the specificity of the ligand-analyte interaction. Experiments were performed as described above, but with a slight excess of a-O-methyl-neurarnatic acid, a known inhibitor for influenza virus hemagglutination. The presence of the inhibitor resulted in no detectable color change of the biopolymeric material.

It is contemplated that the influenza virus detection system include additional ligands that recognize and differentiate influenza strains or serotypes from one another and from other pathogens.

The sialic-acid containing biopolymeric materials of the present invention provide means of detecting many other pathogens. In addition to influenza virus, sialic acid has the capability of detecting other analytes including, but not limited to, HIV, chlamydia, reovirus, *Streptococcus suis*, Salmonella, Sendai virus, mumps, newcastle, myxovirus, and *Neisseria meningitidis.*

II. Detection of Cholera Toxin

Cholera toxin is an endotoxin of the Gram-negative bacterium *Vibrio cholerae* that causes potentially lethal diarrheal disease in man. Cholera toxin is composed of two subunits: A (27 kDa) and B (11.6 kDa) with the stoichiometry $AB_5$. The B components bind specifically to $G_{M1}$ gangliosides on cell surfaces, ultimately leading to translocation of the $A_1$ fragment through the membrane. Cholera toxin can be recognized by $G_{M1}$-containing supported lipid membranes and polymerized Langmuir-Blodgett films containing $G_{M1}$ and a carbohydrate "promoter" lipid (i.e., sialic acid-derived diacetylenes) as shown by Pan and Charych (Langmuir 13: 1365 [1997]).

Ganglioside $G_{M1}$, cholera toxin from *Vibrio Cholerae*, human serum albumin, and wheat germ agglutinin were purchased from Sigma. 5,7-docosadiynoic acid was synthesized. Deionized water was obtained by passing distilled water through a Millipore μF ultrapurification train. Solvents used were reagent grade. The ganglioside $G_{M1}$ was mixed at 5 mol % with the diacetylene "matrix lipid" monomers. Liposomes were prepared using the probe sonication method and polymerized by UV irradiation (254 nm). The conjugated ene-yne backbone of polydiacetylene liposomes results in the appearance of a deep blue/purple solution. The visible absorption spectrum of the freshly prepared purple liposomes is shown in FIG. 25.

For the colorimetric assay, cholera toxin was diluted to 1 mg/ml in 50 mM Tris buffer, pH 7.0. In a 500 μl glass cuvette, blue phase liposomes produced as above were diluted 1:5 in 50 mM Tris buffer, pH 7.0. The liposomes were pre-incubated in the buffer for 15–30 minutes to ensure stability of the blue phase prior to the addition of cholera toxin. No color changes were observed during this period.

Cholera toxin was added to the cuvette by the method of successive additions. After each addition, the contents were mixed and the visible absorption spectrum was recorded as a function of time. Typically, 95% of the absorption changes were observed to occur within the first 2 minutes after addition of toxin as shown in FIG. 26. After each experiment, the contents of the cuvette were transferred to a single well of a white microtiter plate. The pink-orange color of the cholera-treated liposomes was verified visually with a blue negative control.

A negative response was observed if the ganglioside $G_{M1}$ ligand was removed from the liposomes. Similarly, negative responses were obtained when comparable quantities of other proteins besides cholera toxin were added to the $G_{M1}$-containing liposomes. These include human serum albumin, avidin, and wheat germ agglutinin.

Kinetic experiments indicate that greater than 95% of the color change occurs within the first two minutes of adding the toxin. As shown in FIG. 28, the color transition is not an all or nothing effect but depends on the quantity of toxin titrated into the solution. The sigmoidal behavior suggest cooperativity of the colorimetric transition. Although it is not necessary to understand the mechanism in order to use the present invention, and it is not intended that the present invention be so limited, it is contemplated that this may indicate that the binding itself is cooperative in the sense that binding of toxin to the $G_{M1}$ ligand makes the binding of subsequent toxins more favorable. Alternatively this result might more appropriately be understood in terms of the lipid-polymer side chain conformation and its result on the effective conjugated length of the polydiacetylene backbone. Once the effective conjugated length is reduced as a result of toxin binding, subsequent perturbation of the remainder of the lipid-polymer backbone becomes more favorable.

III. Detection of *E. coli* Toxin

Liposomes were prepared with 5% by mole of $G_{M1}$ and 95% 5,7-DCDA. For the colorimetric assay, *E. coli* toxin (Sigma) was spun through a 30 K molecular weight cutoff filter at 2000×g at 15° C. to remove salts. The protein was re-diluted in 50 mM Tris buffer pH 7.0 to a final concentration of 1 mg/ml.

FIG. 29 shows the visible absorption spectrum of the polymeric liposomes containing 5% $G_{M1}$ ligand and 95% 5,7-DCDA prior to exposure to *E. coli* toxin. The liposomes were diluted in 50 mM Tris buffer, pH 8.0 to a final concentration of 0.2 mM in a plastic disposable cuvette. The solution in the cuvette appeared purple to the naked eye.

To the liposomes solution in the cuvette, 40 μl of the above *E. coli* toxin was added and the sample allowed to incubate for 10 minutes. The visible absorption spectrum was again recorded as shown in FIG. 30. The solution in the cuvette appeared pink to the naked eye after the addition of the toxin compared to a purple color before the addition. The absorption spectra of FIGS. 29 and 30 confirm the color changes observed.

IV. Detection of Other Pathogens

The present invention may also be used to detect a variety of other pathogens. Ligands, specific for a large number of pathogens (e.g., carbohydrates, proteins, and antibodies) can be incorporated into the biopolymeric material using routine chemical synthesis methods described above and known in the art. Some of the examples of pathogen detection systems are presented below to demonstrate the variety of methods that can be applied using the present invention and to demonstrate the broad detecting capabilities of single ligand species (e.g. sialic acid).

The sialic acid derivated material of the present invention has been used to detect the presence of parasites such as Plasmodium (i.e., the etiologic agent that causes malaria). In these embodiments, the genetically conserved host binding site was utilized. PDA films containing sialic acid as described above were exposed to solutions containing malaria parasites and erythrocytes. After overnight exposure to the parasites, the films became pink in color. The color response (CR) in each case was nearly 100%. It is contemplated that the system be used in conjunction with other testing material (e.g., arrays of biopolymeric material with various ligands) to identify and differentiate the presence of particularly virulent species or strains of Plasmodium (e.g., *P. falciparum*) or other pathogens.

In yet other embodiments, antibodies were used as ligands to successfully detect the presence of *Neisseria gonorrhoeae* and *Vibrio vulnificus*. The incorporation of the antibodies into the biopolymeric material is described in Example 5.

As is clear from these examples, the present invention provides a variety of means to detect a broad range of pathogens, including bacteria, viruses, and parasites.

V. Detection of Volatile Organic Chemicals (VOCs)

Certain embodiments of the present invention provide means to calorimetrically detect volatile organic compounds (VOCs). Most of the current methods of VOC detection require that samples be taken to laboratory facilities where they are analyzed by gas chromatography/mass spectroscopy. Some of the on-site methodologies require large, bulky pieces of equipment such as that used in spectroscopic analysis. While these methods are excellent for providing quantitation and identification of the contaminant, they cannot ensure the safety of the individual worker. In one embodiment, the present invention provides a badge containing immobilized biopolymeric material that signals the presence of harmful VOCs and provides maximum workplace safety within areas that contain VOCs. The badge is easy and simple to read and requires no expertise to analyze on the part of the wearer. The color change of the badge signals the individual to take appropriate action. The badges reduce costs and improve the efficiency of environmental management and restoration actions, significantly reducing down-time due to worker illness by preventing overexposure to potentially harmful substances.

Two main approaches toward VOC detection have been adopted by various groups. The first involves traditional analytical techniques such as GC/MS that have been modified for VOC detection (i.e., an instrument-based approach) (Karpe et al., J. Chromatography A 708: 105 [1995]). However, these methods are expensive, complicated, and do not lend themselves to field or home use. The second involves the coupling of lipid membranes to detector surface (s) (i.e., an organic-device approach). In the past decade, several sensor devices that involve the coating of a piezoelectric mass balance with an organic film have been investigated. Because of the non-selective nature of the coating, these have been investigated in an array. These sensors, such as the quartz crystal microbalance (QCM) and the surface acoustic wave (SAW) devices (See e.g., Rose-Pehrsson et al., Anal. Chem. 60: 2801 [1988]), have linear frequency changes with applied mass. By applying a polymer or other coating to the crystal, a sensor based on the QCM or SAW is constructed. The complex electronics involved in the use of SAW, QCM, and electrode based systems makes these approaches less amenable to use as personal safety devices.

The present invention differs from these methods in that signal transduction is an integral part of the organic layer structure rather than signal transduction to an electronic device. In addition, embodiments of the present invention facilitate optical detection of the signal rather than electronic detection. Furthermore, the present invention provides flexibility in material design, allowing easy immobilization into a small cartridge (e.g., a badge) rather than being burdened with the need for electronic equipment.

Figure 31:
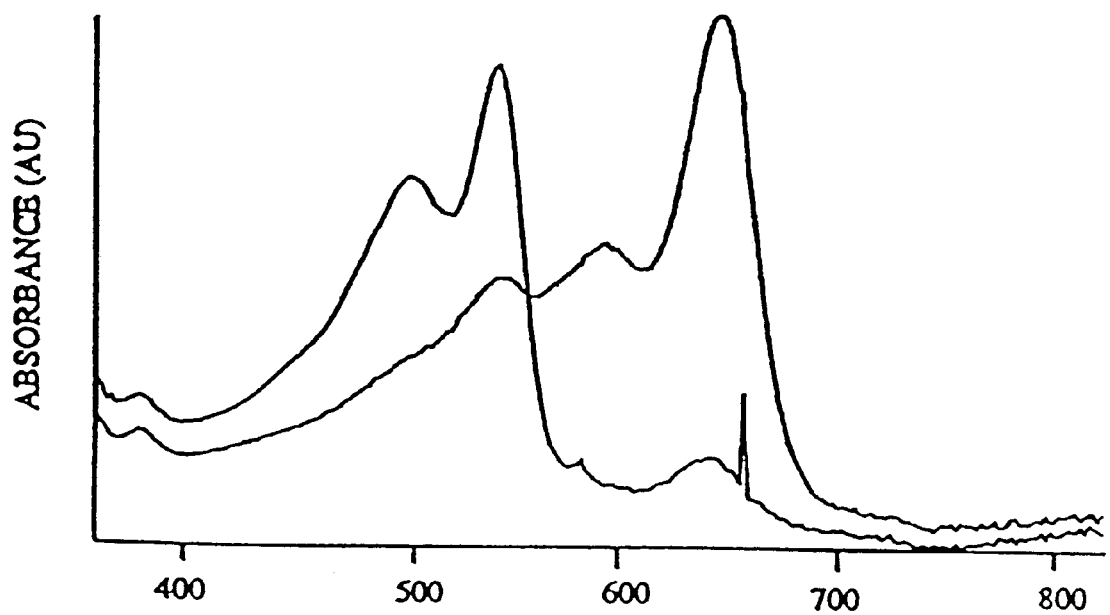
FIG. 31 shows the absorption spectrum of a PCA film in before (line a) and after exposure to 1-octanol dissolved in water (line b).
Figure 32:
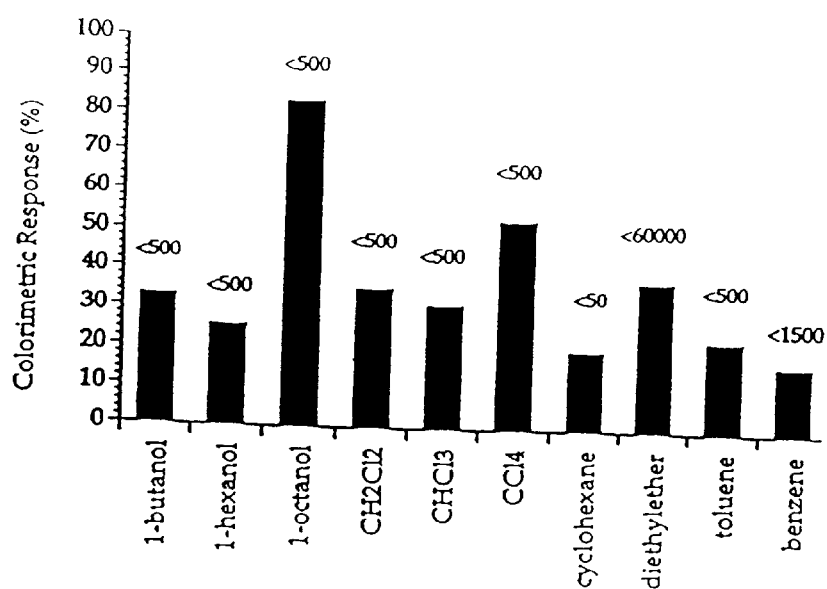
FIG. 32 shows a bar graph indicating colorimetric responses of PDA material to various VOCs (A) and a table showing the concentration of the VOCs (B).

During the development of the present invention, it was observed that the interaction of volatile organic solvents with certain lipid-polymer membranes produced a strong blue to red color transition. FIG. 31, curve a, shows the absorption spectrum of a PCA film in blue phase. The film changes to red phase PCA, curve b, upon exposure to approximately 500 ppm of 1-octanol dissolved in water. For a variety of solvents analyzed, the degree of color change was generally dependent upon the concentration of the solvent and also increased with the extent of halogenation and aromaticity. In this study, a single component thin membrane film of PCA was prepared and polymerized to the blue state by UV exposure (254 nm). These materials were more sensitive to water-immiscible solvents than to water-miscible solvents. For the miscible alcohols, it was found that the response increased dramatically for isopropanol compared to ethanol, perhaps because of a greater extent of solvent intercalation into the membrane. For the water-immiscible solvents, measurable color changes were obtained at 0.05 wt % (500 ppm). Within this group, a similar trend was observed with increased alcohol chain length, as well as with increased extent of chlorination. A wide variety of water-immiscible solvents were examined at their water-saturation concentration, as shown in FIG. 32A and B. As indicated in section B, each concentration is different. In FIG. 32A, the y-axis represents the colorimetric response, or the extent of blue-to-red conversion. The numbers above the bar represent an upper limit to the detection in ppm. For many of these solvents, it is clear that solvent concentrations well below 500 ppm can be detected.

Figure 33:
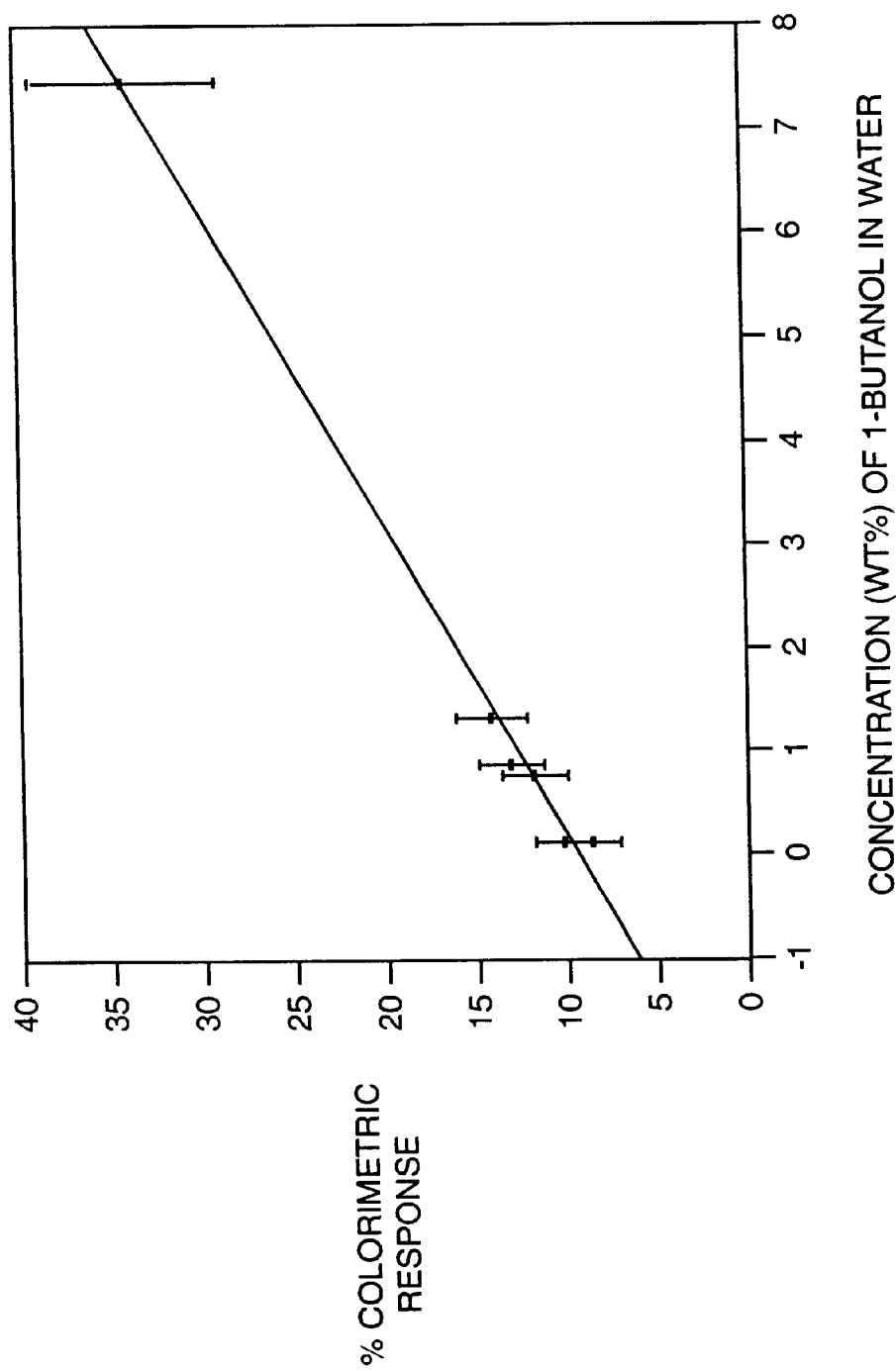
FIG. 33 shows a graph comparing colorimetric responses of biopolymeric material to 1-butanol to the concentration of 1-butanol.

For the immiscible solvents that have a relatively high solubility in water, it was possible to examine the effect of solvent concentration on the colorimetric response. A linear relationship was found to exist between the colorimetric response and solvent concentration in water in the range of 0.05–8 wt % as shown in FIG. 33 for 1-butanol.

The pharmaceutical industry has an ongoing need for solvent sensors, as pharmaceutical compounds are typically manufactured through organic chemical reactions that take place in the presence of solvents. Before packaging of a drug for use in humans or other animals, the solvent must be completely driven off (Carey and Kowalski, Anal. Chem. 60: 541 [1988]). The currently used method for detecting these VOCs uses energy intensive dryers to blow hot air across the drug and piezoelectric crystal arrays to analyze the evaporation of the various solvents (Carey, Trends in Anal. Chem. 13: 210 [1993]). The present invention provides a colorimetric based approach that greatly simplify these measurements.

In addition, interest in analytical methods for the quantitation of VOCs in non-industrial indoor air environments has increased dramatically in the last several years. This is due primarily to a heightened awareness of emissions from common household appliances or office equipment, as well as trends in controlled building ventilation. Companies that produce consumer products have an interest in serving this increased need by providing indoor air monitors that can deduce the presence of hazardous VOCs in-situ, without the need for air sampling and subsequent laboratory analysis. The present invention provides embodiments to achieve such means. Indeed, embodiments of the present invention provide for enhanced air sampling, and the cartridges may be connected to small, portable, battery-operated pumps for personal or general air sampling.

VI. Detection of Other Small Organic Molecules

Figure 34:
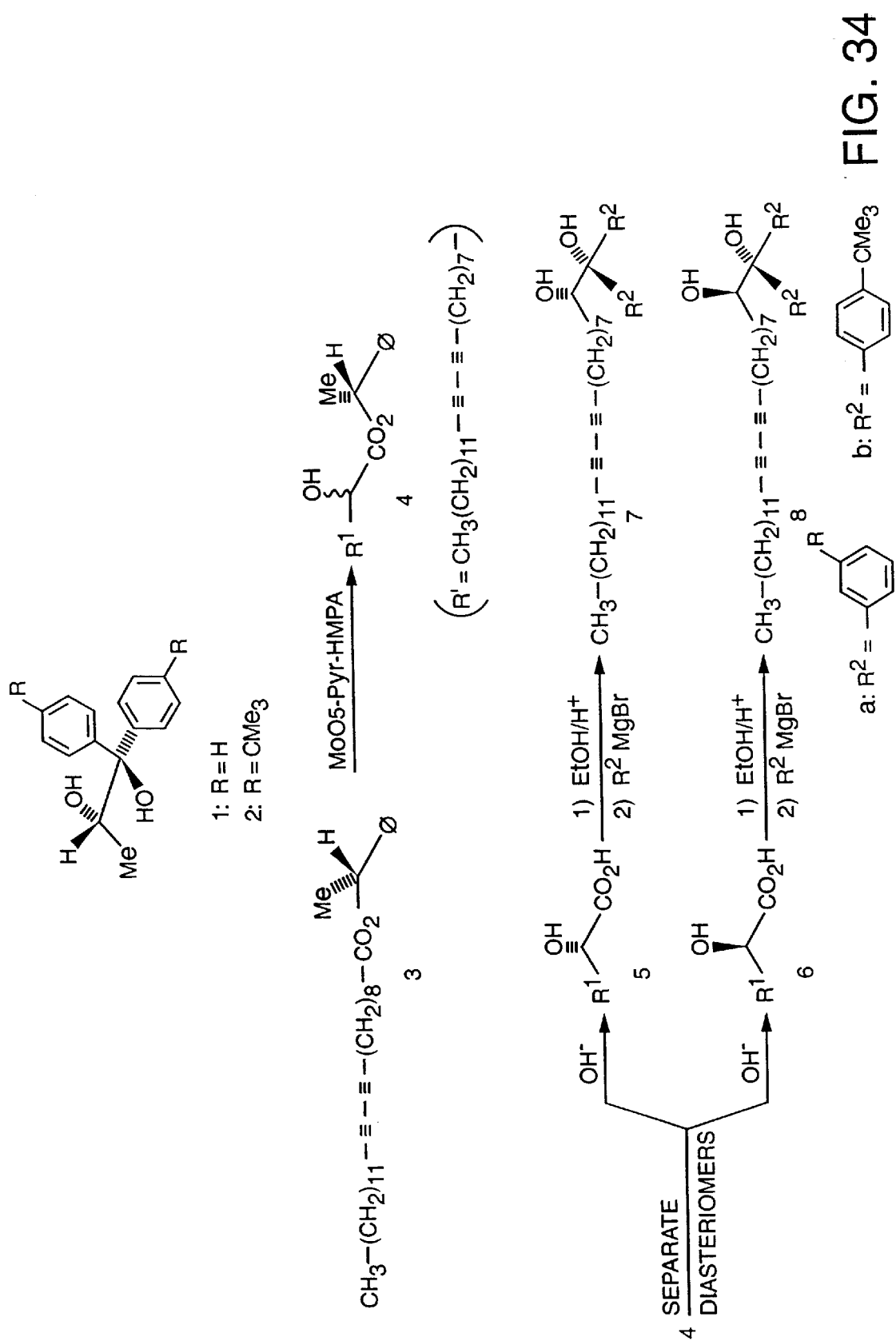
FIG. 34 shows compounds and synthesis schematics for producing PDA derivatives for the detection of small organic compounds.
Figure 35A:
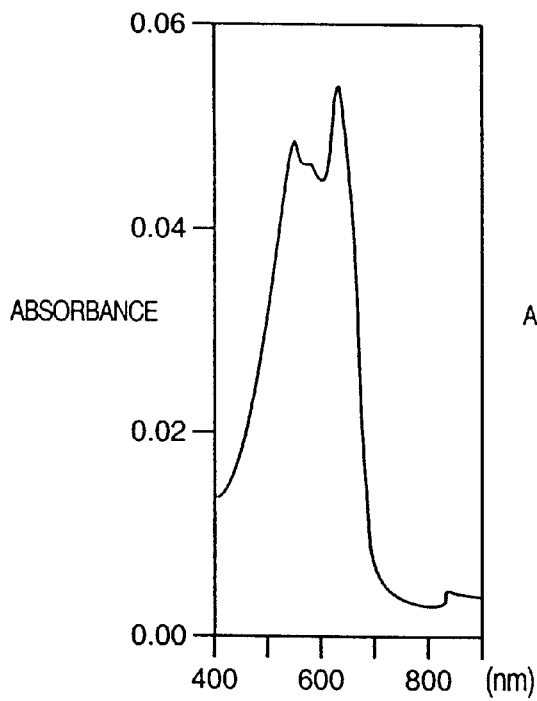
FIG. 35 shows the UV-Vis spectra of a hexokinase modified PDA monolayer upon addition of glucose as a function of incubation time at (A) background, (B) t=0.02 min, (C) t=30, and (D) at t=60 min.
Figure 35B:
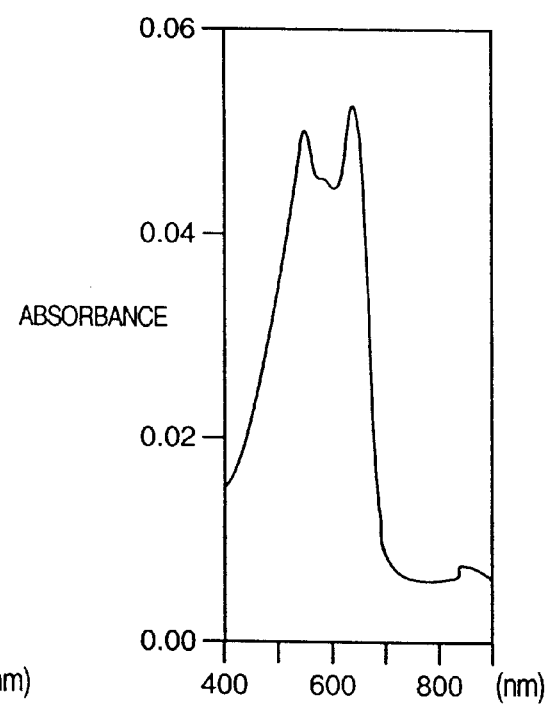
Figure 35C:
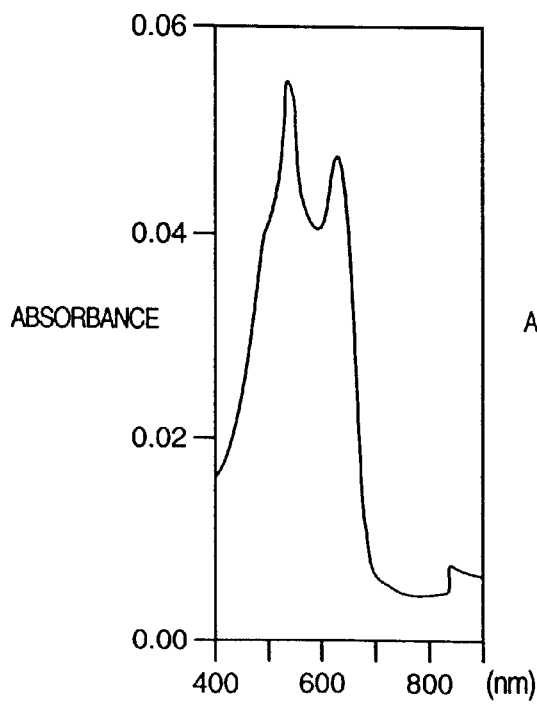
Figure 35D:
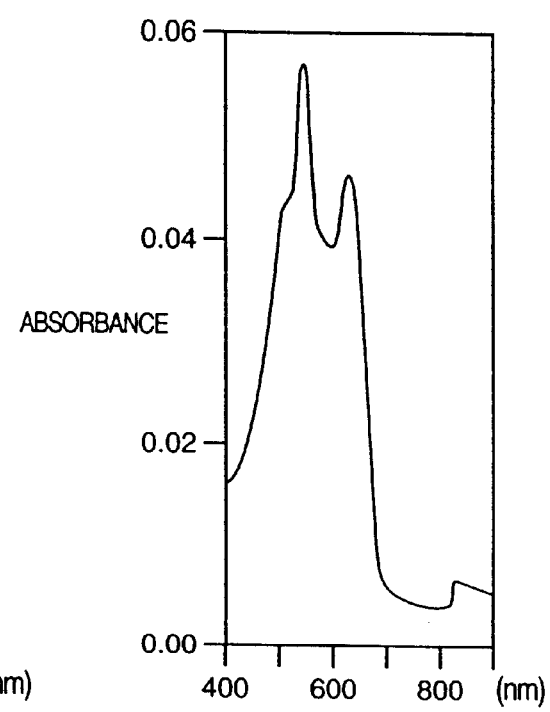

Certain inclusion compounds, or clathrates, such as compounds 1 and 2 in FIG. 34 have been shown to be highly selective sorbents for organic solvent vapors (Ehlen, et al., Angew, Chem. Int. Ed. Engl. Vol. 32, p. 110 [1993]). For example, compound 1 has a pronounced affinity for dioxane and little affinity for butanol, acetone, methanol, 2-propanol, cyclohexane, toluene, and water. Compound 2 on the other hand, shows a pronounced affinity for 1-butanol over the same group of solvents.

The purpose of this example is to show the development of a new class of functional materials that specifically trap small organic compounds and report the entrapment event by a colorimetric change which can be detected visually. These material act as simple color-based sensor devices that detects the presence of compounds such as solvents or other toxic pollutants in air or water streams.

The first step involves the synthesis of lipid diacetylene analogs of compounds 1 and 2 as shown in FIG. 34. In this figure, the enantiometrically pure ester of PDA (pentacosadiynoic acid) 3 is hydroxylated via molybdenum peroxide oxidation to alcohol 4. Diasteriomers are separated and the ester is hydrolyzed to chiral lactate analogs 5 and 6. The ethyl esters are formed and treated with Grignard reagents to give the desired chiral lipid analogs 7 and 8. Variation in the R groups result in a wide variety of new materials in which the specific entrapment capabilities are reviewed.

The monomer-lipid clathrate is ordered and compressed on the water surface using a Langmuir-Blodgett film apparatus. Polymerization of the monolayer by UV irradiation yields the blue colored material as described above. The film is lifted onto a hydrophobized microscope slide. Exposure of these materials to analytes (e.g., 1-butanol or dioxane) produces a colorimetric response.

VII. Detection of Glucose with Hexokinase Ligands

For the colorimetric measurements, the hexokinase modified films, as described above, were placed onto silanized glass cover slides for the purpose of measuring the optical properties. The biosensor coated glass cover slides were placed in glass cuvettes and the UV-Vis spectra of hexokinase modified films were recorded in 0.1 M phosphate buffer (pH 6.5). Measurements taken in this buffer condition were considered background. Addition of glucose, or other sugar substitutes, occurred directly in the cuvettes. FIG. 35 shows the UV-Vis spectra of a hexokinase modified PDA monolayer upon addition of glucose as a function of incubation time, showing (A) background (0.1 M phosphate buffer, pH 6.5); (B) at t=0.02 min after addition of 10.0 mM glucose; (C) at t=30 min after addition of 10.0 mM glucose; and (D) at t=60 min after addition of 10.0 mM glucose.

It is clear that addition of glucose provokes an immediate response as reflected by the increase in absorbance at 550 nm. The response increases with time, reaching its peak at 60 minutes. The colorimetric response (CR), defined above, was 5.2, 13.7, and 17.1% for t=0.02, 30, and 60 minutes, respectively. The color change was irreversible under these conditions.

Figure 36:
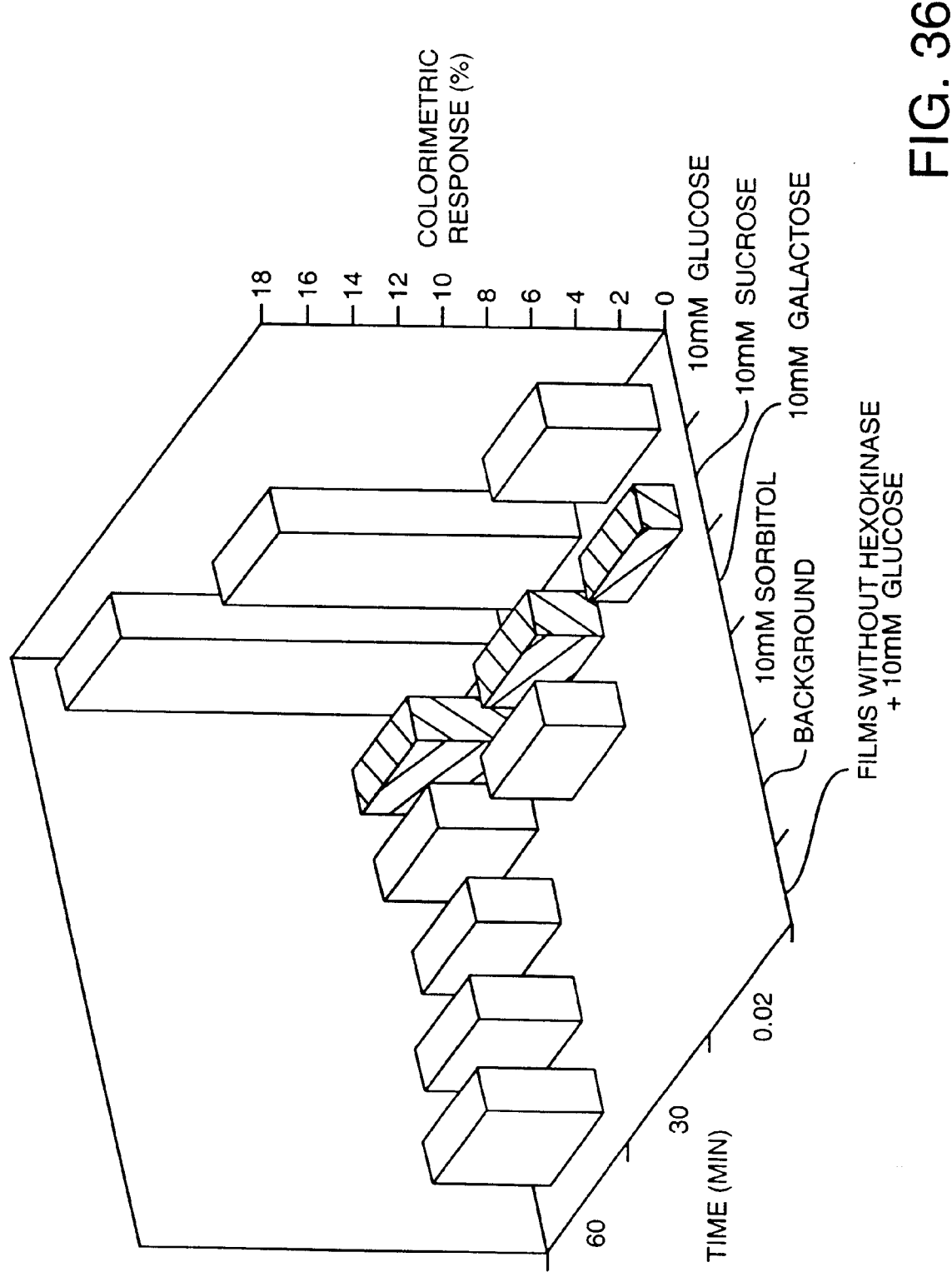
FIG. 36 shows the calorimetric response of hexokinase containing biopolymeric material to a variety of sugars.

The selectivity of the glucose sensor was studied using sugar compounds structurally similar to glucose as shown in FIG. 36. All tests were made in 0.1 M phosphate buffer (pH 6.5). The second to the last column on the right represents the glucose agitation on the PDA monolayers without immobilized hexokinase. The sampling number (n) for the glucose is n=6, while for the rest n=3. Addition of 10.0 mM sorbitol, galactose, and sucrose did not trigger the sensor, suggesting that the sensor is very specific for the sugar glucose. To further examine the mechanism of activation of the sensor, a PDA monolayer without immobilized hexokinase was tested. No significant response was observed, as the CR at t=60 minutes was comparable to the background of the hexokinase-conjugated PDA monolayer. The result demonstrated that glucose by itself cannot induce the color change in the PDA films. The presence of immobilized hexokinase was required to allow the sensor to respond to glucose.

VIII. Detection of Nucleic Acid Hybridization Events

Figure 40:
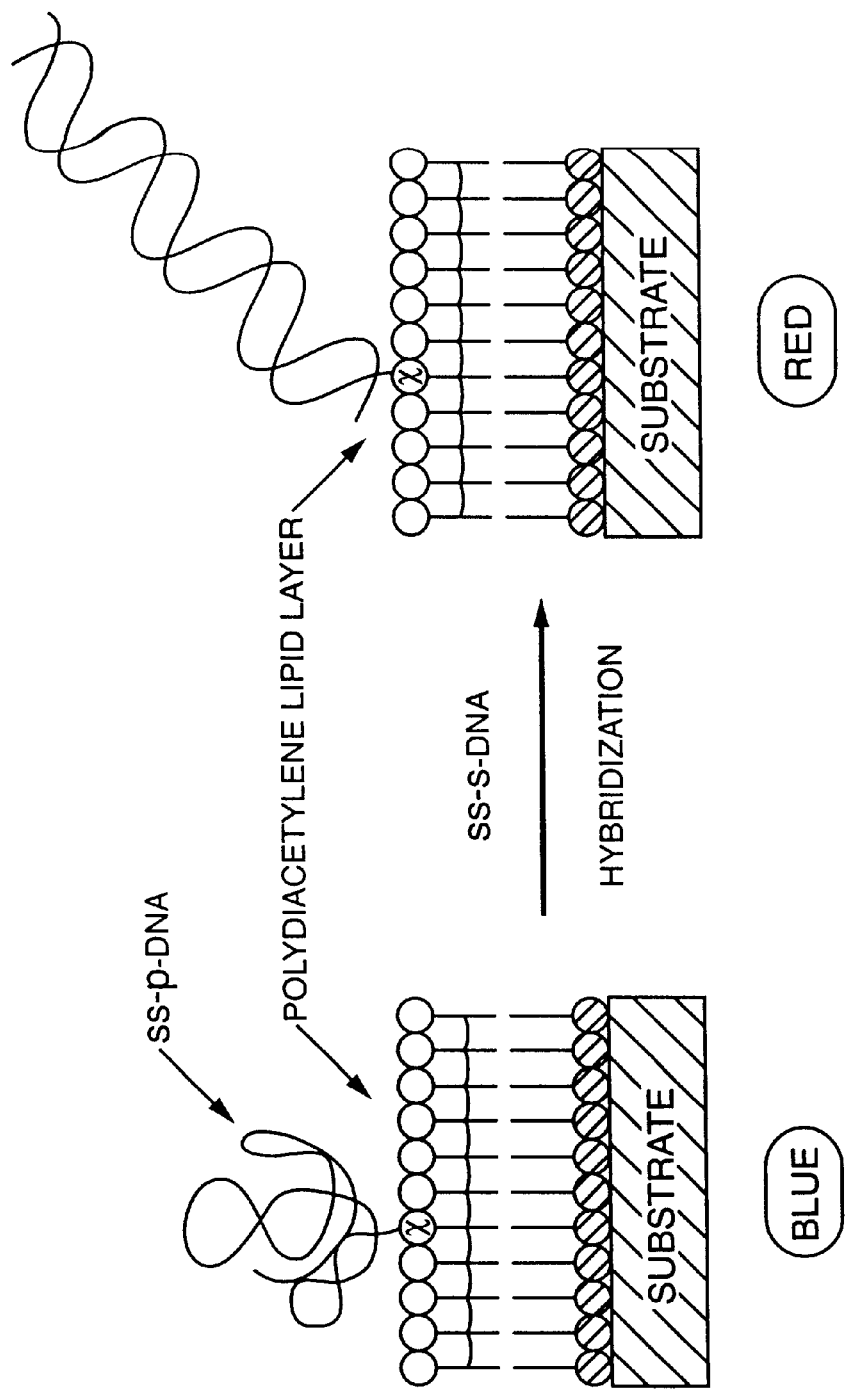

In other embodiments, the materials of the present invention comprise nucleic acid ligands that allow specific detection of DNA hybridization or other nucleic acid interactions via nucleic acid molecular recgnition of a single stranded sample DNA (ss-s-DNA) with single stranded probe DNA (ss-p-DNA), which is covalently attached to the surface of the biopolymeric material of the present invention. With certain biopolymeric materials, a color transition occurs upon analyte binding that can be viewed by simple visual observation or, if desired, by color sensing equipment. The colorimetric detection of DNA hybridization is illustrated schematically in FIG. 40.

IX. Other Examples

The examples provided above demonstrate the broad range of analytes detectable by the present invention, ranging from complex biological organisms (e.g., viruses, bacteria, and parasites) to simple, small organic molecules (e.g., alcohols). A number of other analytes have been successfully detected using ligands linked to biopolymeric material including, but not limited to botulinum neurotoxin detected with ganglioside incorporated PDA (Pan and Charych, Langmuir 13: 1367 [1997]). It is contemplated that numerous ligand types will be linked to self-assembling monomers using standard chemical synthesis techniques known in the art to detect a broad range of analytes. Additionally, numerous other ligand types can be incorporated into the biopolymeric matrix without covalent attachment to self-assembling monomer. These materials allow for the detection of small molecules, pathogens, bacteria, membrane receptors, membrane fragments, volatile organic compounds, enzymes, drugs, and many other relevant materials.

The present invention also finds use as a sensor in a variety of other applications. The color transition of PDA materials is affected by changes in temperature and pH. Thus, the methods and compositions of the present invention find use as temperature and pH detectors.

Ligands can also be used in the present invention when they function as competitive binders to the analyte. For example, by measuring the colorimetric response to an analyte in the presence of a natural receptor for the analyte, one can determine the quantity and/or binding affinity of the natural receptor. Application of competition or inhibition techniques allow the testing of very small, largely unreactive compounds, as well as substances present in very low concentrations or substances that have a small number or single valiancy. One application of this technique finds use as a means for the development and improvement of drugs by providing a screening assay to observe competitive inhibition of natural binding events. The compositions of the present invention further provide means for testing libraries of materials, as the binding of desired material can be calorimetrically observed and the relevant biopolymeric material with its relevant ligand separated from the others by segregating As out a particular polymeric structure.

EXAMPLE 8

Immobilization of Biopolymeric Material

I. Immobilization to Silicon Chips and Gels

The silicon gel or wafers are acid cleaned in 1:1 HCl/methanol, rinsed in water, and placed in concentrated sulfuric acid. After a thorough water rinse, the wafer chips or gel is boiled in doubly distilled deionized water, allowed to cool and dry and then silanized under inert atmosphere in a 2% solution of 3-mercaptopropyl trimethoxysilane prepared in dry toluene. Next, the chips or gels are placed in a 2 mM solution of either GMBS (N-succinimidyl 4-maleimidobutyrate) or EMCS (N-succinimidyl 6-maleimidocaproate) prepared in 0.1 M phosphate buffer (the cross linker is first dissolved in a minimal amount of dimethylformamide). After rinsing with phosphate buffer, the chips are placed in a 0.05 mg/ml solution of the liposomes prepared in pH 8.0 phosphate buffer. Finally, the chips or gels are thoroughly rinsed with, and then stored in, the buffer solution prior to their use. The liposomes should have an —$NH_2$ functionality for the cross-linking with GMBS or EMCS to work.

II. Sol-Gel Entrapment of Biopolymeric Material

A silica sol was prepared by sonicating 15.25 g of tetramethylorthosilicate (TMOS), 3.35 g of water, and 0.22 ml of 0.04 N aqueous hydrochloric acid in a chilled bath until the solution was one phase (approximately 20 minutes). Chilled MOPS buffer solution (50% v/v) was then added to the acidic sol making sure that the solution was well cooled in an ice bath to retard gelation. A variety of materials are appropriate for generating silica sols, including, but not limited to, any tetraalkoxysilane or organically modified silane (e.g. ormosil). Additionally, tetraethylorthosilicate (TEOS), methyltriethoxysilane (MeTEOS), aryl silsesquioxanes, and other metal oxides find use in generating sol-gel glass.

For encapsulating liposomes, a polymerized liposome solution (2.5 ml) (as generated in Example 1) was then mixed into the buffered sol (10 ml) and the mixture poured into plastic cuvettes, applied as a film on a flat surface, or poured into any other desired formation template, sealed with Parafilm, and allowed to gel at ambient temperature. Gelation of the samples occurred within a few minutes resulting in transparent, monolithic solids (18 mm×10 mm×5 mm) in the case of cuvette formed gels and as violet colored monoliths with p-PDA liposomes. Slight shrinkage of aged monoliths was observed due to syneresis.

The encapsulation of other biopolymeric material shapes (i.e., film and other nanostructures) can be conducted as described above. The materials must be generated or sectioned into small (i.e., nanoscopic) sized portions if not already so, and incorporated into a solution to be mixed with the buffered sol.

EXAMPLE 9

Generation of Arrays

In some embodiments, the present invention contemplates the generation of a large palette of polymerizable lipids of different headgroup chemistries to create an array. Lipids containing head groups with carboxylic acid functionalities (imparting a formal negative charge), hydrophilic uncharged hydroxy groups, primary amine functionalities (that may acquire a formal positive charge), amino derivatives (with positive, negative or zwitterionic charge), and hydrophobic groups among others can be generated. In some embodiments of the present invention, the combination of these materials into a single device facilitates the simultaneous detection of a variety of analytes or the discrimination of a desired analytes from background interferants. In some embodiments, biopolymeric materials comprising varying dopant materials are used to provide a different color pattern for each portion of the array.

For example, a large palette of polymerizable lipids of different headgroup chemistries can be generated to create an array. For example, FIG. 37 depicts lipids with various head group chemistries. These may be categorized into five groups based upon their head group functionality. Compounds 2.4 and 2.5 contain carboxylic acid functionalities, imparting a formal negative charge. Compounds 2.6 and 2.7 contain a hydrophilic uncharged hydroxyl group. Compounds 2.8 and 2.9 have primary amine functionalities that may acquire a formal positive charge. The amino acid derivative 2.10 may exist with positive, negative or zwitterionic charge. Compounds 2.11–2.13 have hydrophobic head groups.

Figure 38:
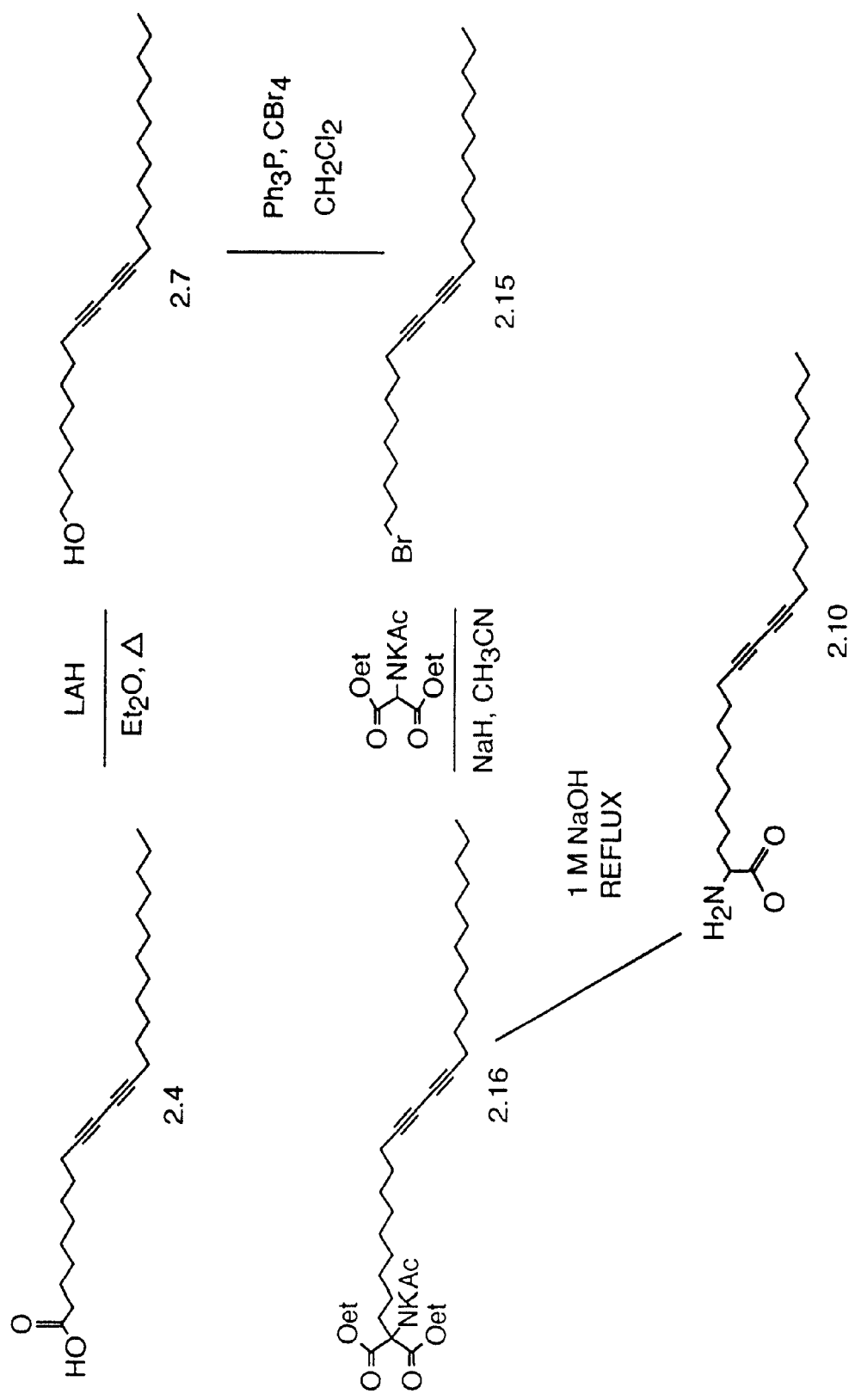
FIG. 38 shows the organic synthesis of compound 2.10 from FIG. 37.

The synthesis of these lipids begins with commercially available PDA (2.4). Synthesis of all but 2.10, 2.12, and 2.13 can be carried out by coupling the respective head group to PDA utilizing the activated N-hyroxysuccinimidyl ester of PDA (NHS-PDA) as described above. The amino acid lipid 2.10 can be prepared in four steps from PDA as shown in FIG. 38, using lithium aluminum hydride and transformation of the alcohol to the corresponding bromide derivative. The bromide is converted to the protected amino acid by reaction with diethyl N-acetimidomalonate in acetonitrile with sodium hydride, followed by deprotection. The fluorinated lipids 2.12 and 2.13 can be prepared by the reaction of pentafluorobenzoyl chloride with amino lipids 2.8 and 2.9.

Materials prepared as above, can be deposited into chambers of a device or immobilized to specific portions of a device. By generating biopolymeric materials with different properties (e.g., analyte or reaction detection capabilities, colors, analytes affinities) within a single apparatus (e.g. a badge), an array is generated with the ability to identify, distinguish, and quantitate a broad range of reactions and analytes.

Figure 46:
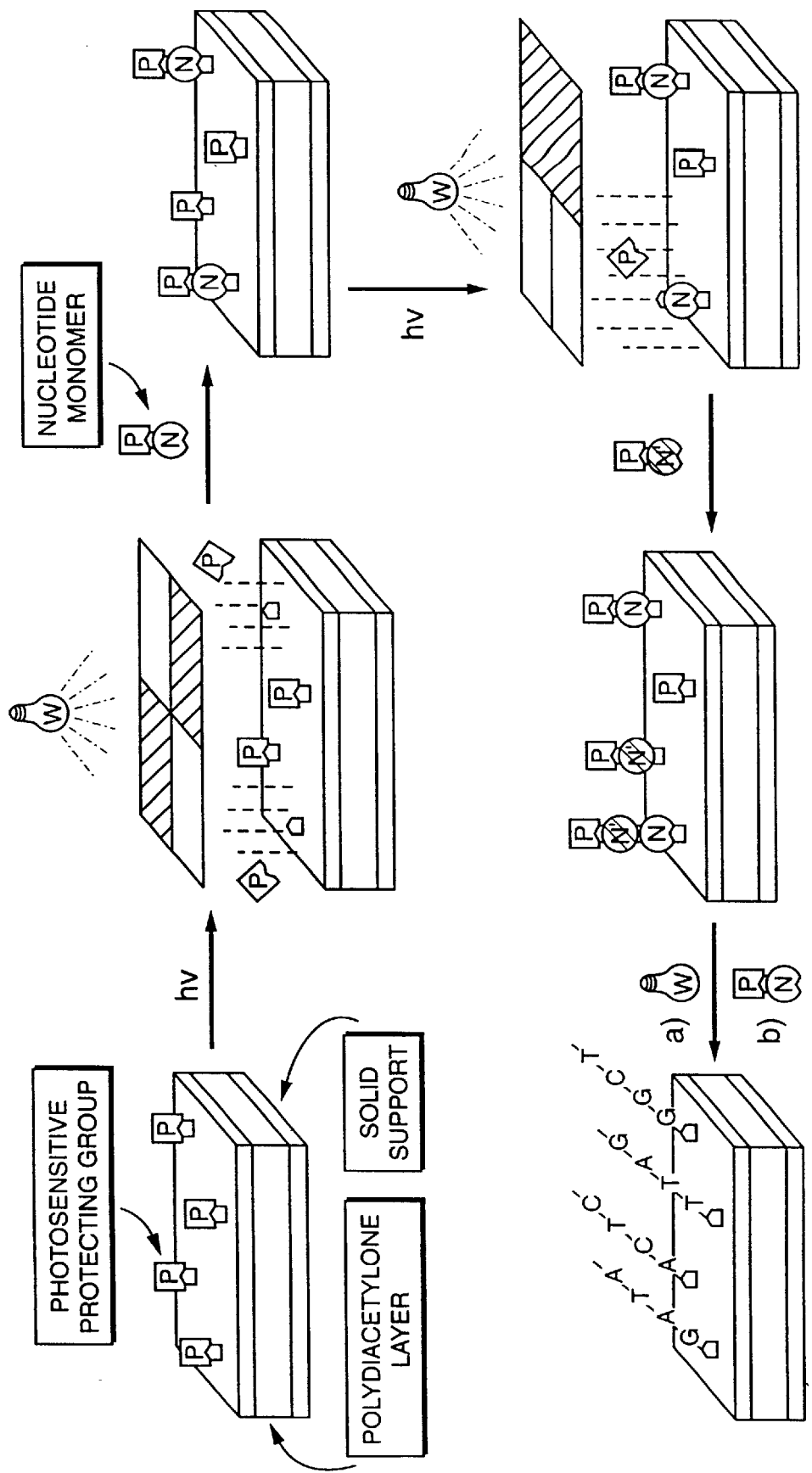

In other embodiments, the construction of a patterned DNA assay automated DNA synthesis is carried out with the growing chain linked to the polydiacetylene bilayer system on solid substrates, as shown in FIG. 46. The activated nucleotide monomers which are added in each cycle carry a photosensitive protecting group at the 5' end. After the coupling reaction, the chain ends (5') are capped with the photosensitive protecting group. By irradiation of the substrate through a mask, only the parts of the substrate that are irradiated are deprotected. Thus, on a single substrate (detector) surface several independent ss-p-DNA sequences can be synthesized in a parallel manner by appropriate choice of masks. This approach will yield a powerful multivalent sensor for the detection of many different ss-s-DNA fragments in one step. The method requires a photosensitive protecting group that is cleaved at a wavelength which does not affect the DNA itself ($\lambda_{abs} \approx 260$ nm) or interfere with the polydiacetylene backbone. Such photosensitive protecting groups are o-nitrobenzlyoxy esters of phosphoric acid ($\lambda_{abs} \approx 340$ nm) and related compounds (See, Greene et al., *Protective Groups in Organic Synthesis*, second ed., John Wiley & Sons, Inc., New York [1991]); Pillai, Synthesis, p. 1 [1980]; and Zehavi, Adv. Carbohydr. Chem. Biochem. 46:179 [1988]).

EXAMPLE 10

Detection of Membrane Rearrangements

I. Phospholipase $A_2$

Biopolymeric liposomes were prepared by probe sonication of a mixture of polymerizable matrix lipid 10,12- tricosadiynoic acid and various mole fractions (0%–40%) of PLA$_2$ substrate lipid (e.g., DMPC) in water, followed by polymerization with 1.6 µJ/cm$^2$ ultraviolet radiation, 254 nm. Analysis by transmission electron microscopy indicated an average vesicle size of approximately 100 mn.

In their initial state, the vesicles appeared deep blue to the naked eye and absorb maximally at around 620 nm. Polymerized vesicles composed of 40% DMPC/60% PDA, 1 mM total lipid, were diluted 1:10 in 50 mM Tris buffer pH 7.0 to a final volume of 0.5 ml in a standard cuvette and the spectrum recorded using a Hewlett Packard Spectrophotometer Model 9153C. Bee venom phospholipase A$_2$ (Sigma) was dissolved in a 10 mM Tris, 150 mM NaCl, 5 mM CaCl$_2$ buffer pH 8.9 to yield a final concentration of 1.4 mg/ml PLA$_2$. 50 µl of this solution was added to the cuvette and the spectrum was recorded after 60 minutes. Upon addition of PLA$_2$ to the DMPC/PDA vesicles, the suspension rapidly turned red (i.e., within minutes) and exhibited a maximum absorption at approximately 540 nm as shown in FIG. 13, described above.

Liposomes containing a range of mole% DMPC were tested for their ability to produce a colorimetric response. Five microliters of 1.4 mg/ml PLA$_2$ was added to 50 µl of DMPC/PDA vesicles (0.1 mM final total lipid concentration). The experiment was carried out in a standard 96-well plate using a Molecular Devices UV Max kinetic microplate reader. The absorption of the vesicle solution was monitored as a function of time at 620 nm and 490 nm wavelengths. The data was then plotted as colorimetric response (CR) versus time to yield the color response curves as shown in FIG. 17, described above.

In order to confirm that biocatalysis was occurring at the DMPC/PDA vesicles, PLA$_2$ activity was independently measured using a labeled lipid analog incorporated into the PDA matrix, allowing simultaneous measurement of product formation and colorimetric response of the vesicles. The analog used was thioester 1,2-bis-(S-decanoyl)-1,2-dithio-sn-glycero-3-phosphocholine (DTPC). Five microliters of 40% DTPC/PDA vesicles diluted with 45 µl 40 mM Tris pH 7.0 and 5 µl of 6 mM DTNB were incubated with 10 µl of 1.4 mg/ml PLA$_2$. The absorbance at 412 nm was monitored over time.

NMR experiments were conducted to ftrther verify the occurrence of interfacial catalysis by PLA$_2$, and provide information of the fate of the enzymatic reaction products. The spectra were taken at a magnetic field of 11.7 Tesla on a Bruker DMX500 NMR spectrometer. The Block-decay pulse sequence was used with 2048 acquisition data points. 40,000 free induction decays were accumulated in each experiment with 2 second recycle delays. 0.1 M phosphoric acid was used as an external reference. FIG. 16 shows the $^{31}$P NMR spectra of A) Mixed DMPC/PDA vesicles, 0.1 mM total lipid; B) the same vesicle suspension after addition of PLA$_2$ (200 ng).

II. Phospholipase C and D

The assays for phospholipase D and C were run under similar conditions as the phospholipase PLA$_2$ assays. In all assays, 1 mM 40% DMPC/ 60% 10,12-tricosadiynoic acid (TRCDA) liposomes were used. Aqueous stock solutions of phospholipase D and C were prepared by dissolving the enzymes at 1 mg/ml concentration in 50 mM Tris, 150 mM NaCl, 5 mM CaCl$_2$ pH 8.9 buffer and 20 mM sodium borate, 150 mM NaCl, 5 mM CaCl$_2$ pH 8.9 buffer, respectively. The assays were then performed by adding 5 µl of liposomes, 45 µl 50 mM Tris pH 7.0 (or 20 mM sodium borate pH 7.0 when testing PLC), and 5 µl of enzyme. Controls for the assays consisted of 5 µl of buffer instead of enzyme. The assays were monitored at 620 nm and 490 nm every two minutes for the first ten minutes, and then every ten minutes for the remaining 50 minutes.

III. Bungarotoxin

Assays were conducted under similar conditions to the experiments described above. Ten microliters of 1 mM 40% DMPC/60% TRCDA liposomes, 35 µl of 50 mM Tris pH 7.4, 15 µl BUTX (Molecular Probes B-3459) were dissolved in 50 mM Tris, 150 mM NaCl, 5 mM CaCl$_2$ pH 7.4 to make a 2 mg/ml solution. Spectra were monitored every 2 minutes for the first 10 minutes of the incubation and every 10 minutes for the remaining 50 minutes. Absorbance at 490 and 620 nm were monitored using a UV max microplate reader.

IV. Inhibitor Screening

Inhibitors were used to block the colorimetric event initiated by PLA$_2$. DMPC/PDA vesicles containing 0.6% MJ33 were polymerized and incubated with 5 µl of 1.4 mg/ml PLA$_2$. Five microliters of unpolymerized liposomes were combined with 40 µl of 50 mM Tris pH 7.0, 5 µl MJ33 (0.006 M dissolved in water), 5 µl of 50 mM Tris, 150 mM NaCl, 5 mM CaCl$_2$ pH 8.9, and incubated for 15 minutes. The liposomes were then polymerized in 96 well plates and absorption spectrum were recorded at 490 nm and 620 nm. Five microliters of PLA$_2$ were added and spectra at specific time intervals were monitored for one hour. For Zn$^{2+}$ inhibition, the enzyme was dissolved in 10 mM Tris, 150 mM NaCl, 0.1 mM ZnCl$_2$ pH 8.9.

EXAMPLE 11

Nucleic Acid-Linked Biopolymeric Materials

In these experiments, oligonucleotides were derivatized to form single stranded probe DNA (ss-p-DNA) for incorporation into biopolymeric liposomes. The liposomes were prepared from a lipid mixture of 95% compound 1 (FIG. 41A) and 5% compound 3 (FIG. 41A), as described above by sonicating a dried film of the lipid mixture in an aqueous medium. This liposome solution was photopolymerized by irradiation with UV light (254 nm), and then either compound 4 (FIG. 41B; [SEQ ID NO:2]) or compound 5 (FIG. 41B) was added to form covalent linkages at the active ester lipid sites of compound 3. This process is illustrated in FIG. 42.

Coupling the α,ω-bisamino ss-p-DNA (i e., compound 5) to the surface of the polymeric liposome potentially creates a more sensitive probe than one generated with compound 4. Although an understanding of the mechanism is not required to practice the present invention and the present invention is not limited to any particular explanation, the possible reasons for this increased sensitivity are as follows. The single stranded DNA forms a coiled structure in solution as known from dissolved polymers. Attaching the coiled ss-p-DNA, compound 5, to the liposome surface resulted in two relatively close linkages. Upon hybridization the double helical DNA elongates and causes, simultaneously at both linkages, conformational changes in the polydiacetylene backbone. This cooperative effect increases the sensitivity of colorimetric detection.

The characteristics of these liposomes, such as size and shape, can be determined from various measurements, including TEM (e.g., freeze fracture method) and light scattering. Raman- and UV/Vis spectroscopy give information about the polymer backbone, whereas FTIR spectroscopy is sensitive for the alkyl chains. Surface topology is revealed under the AFM, and the chemical composition of the surface may be probed by XPS, although the present invention does not require such characterization experiments.

Figure 41A:
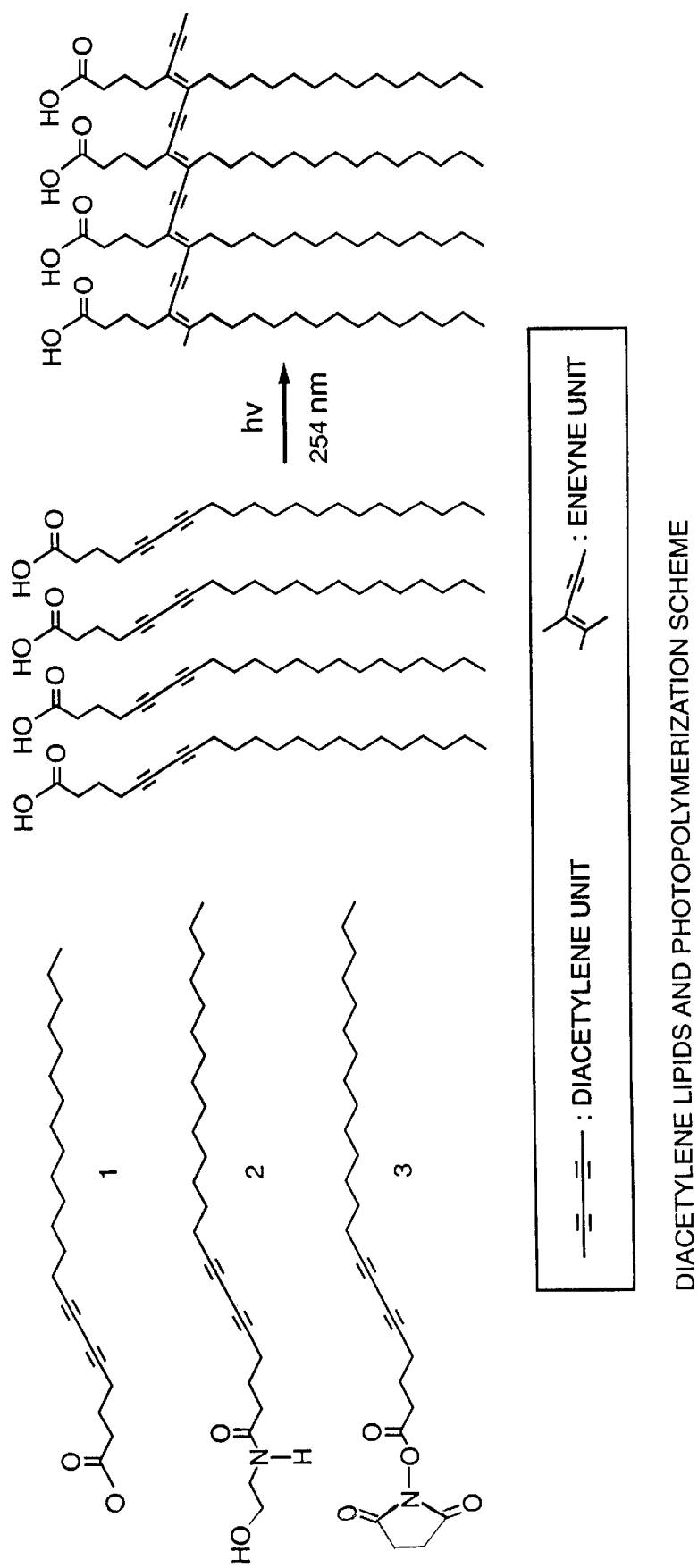
FIG. 41A shows various nucleic acid derivatized biopolymeric materials. Likewise.
Figure 41B:
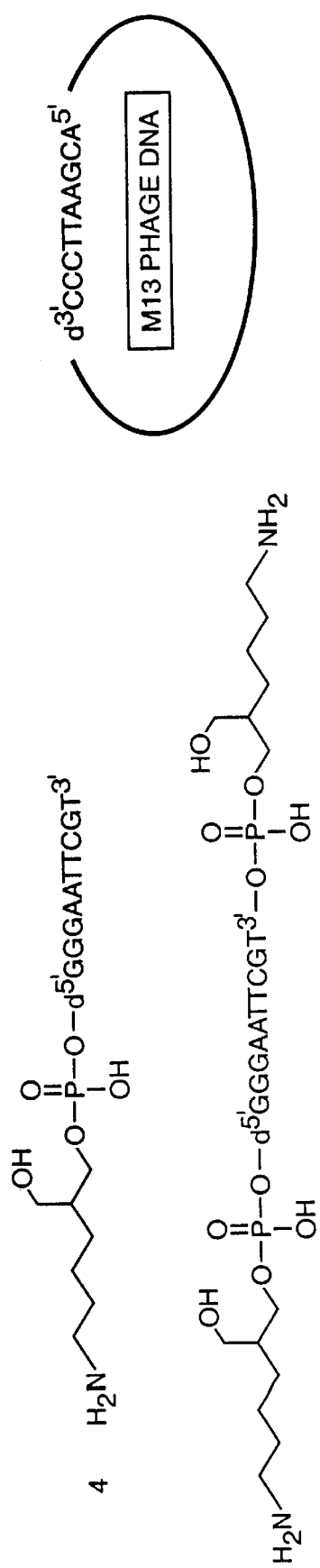
FIG. 41B shows additional nucleic acid derivatized biopolymeric materials. Each of FIGS. 40–50 is described in more detail below.
Figure 42:
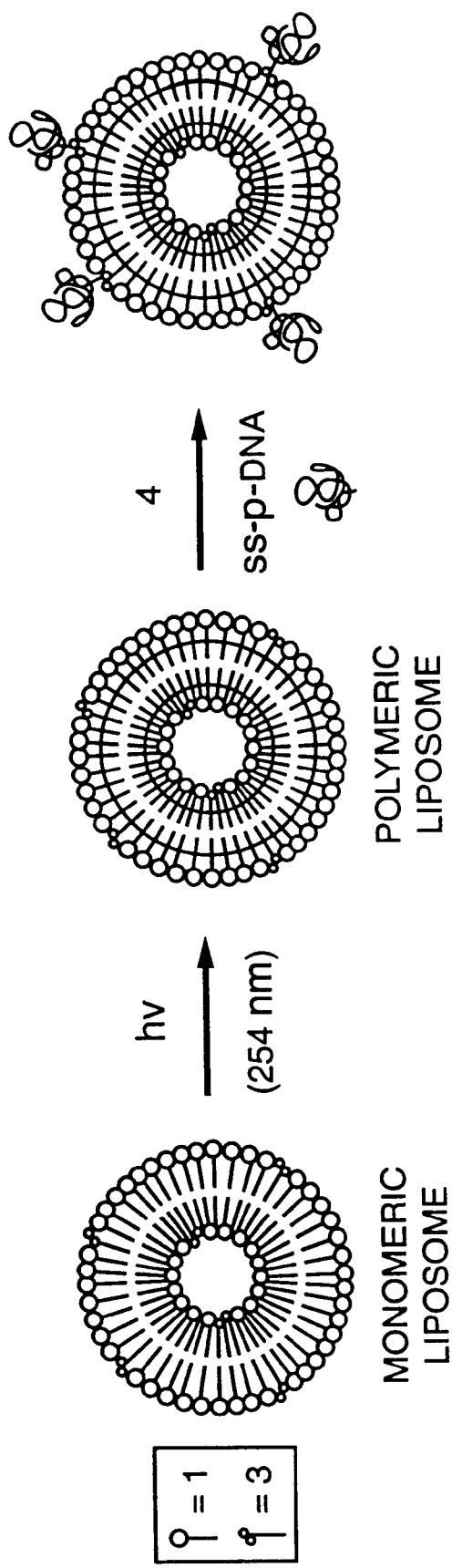

Compound 1 and analogues 2 and 3 of FIG. 41A were used and derivatized to yield the desired functionalizations at the membrane surfaces. FIG. 41A shows the film structure with the conjugated polymer backbone before and after photopolymerization with lipid 1. The oligonucleotide dGG-GAATTCGT (SEQ ID NO:4), complementary to a sequence on the M13 phage DNA, could be derivatized to form the ss-p-DNA compounds 4 and 5 (FIG. 41B), which carry amino groups at the chain ends. These amino groups can react with the active ester lipid, compound 3 (FIG. 41A), in a polydiacetylene film, allowing the attachment of the ss-p-DNA to the liposome or bilayer after photopolymerization. However, it is not intended that the present invention be limited to any particular ss-p-DNA sequences.

Figure 45:
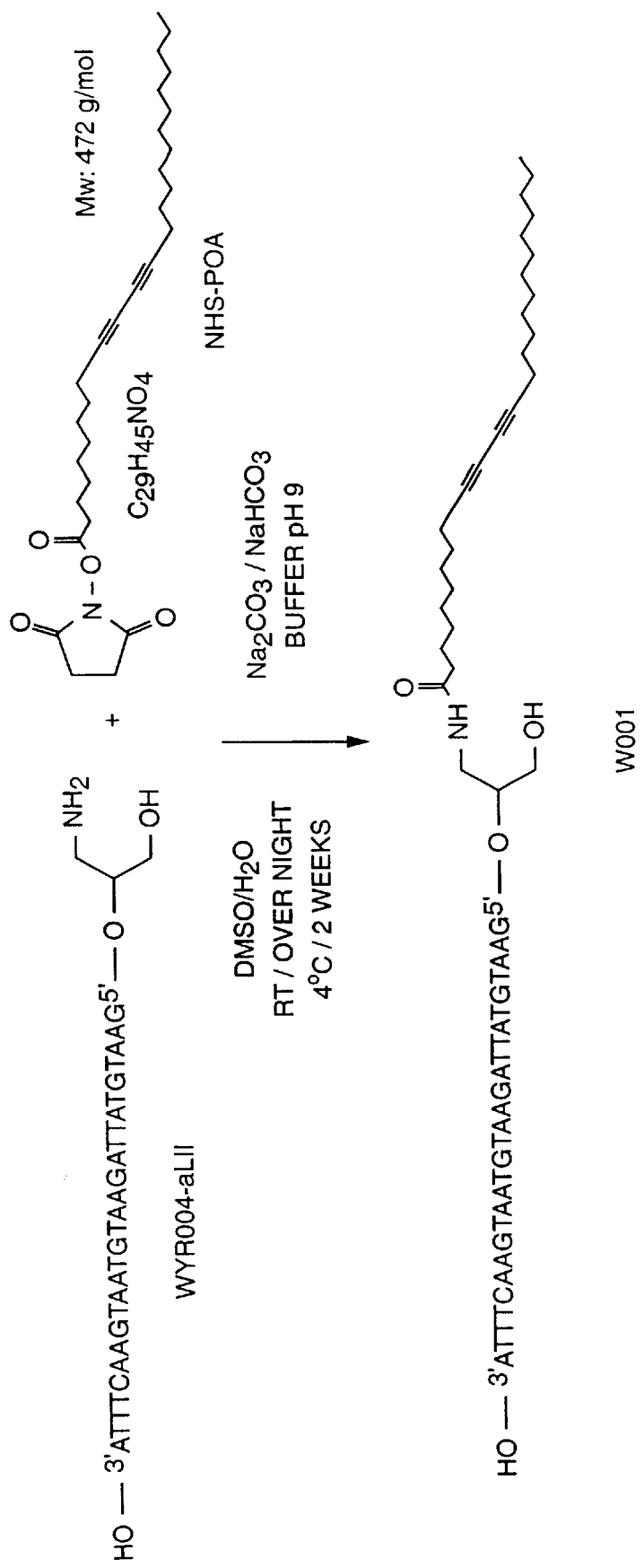

In some experiments, the ODN-lipid conjugate Oligo 1 (hereinafter, "W0001") was obtained by reaction of NHS-PDA with the amino functionalized 27-mer Oligo 1 in DMSO/aqueous buffer medium (pH 9, $Na_2CO_3/NaHCO_3$ buffer, 0.1 M) as shown in FIG. 45. The NHS-PDA dissolved in DMSO partially crashed out of solution when added to the aqueous ODN-buffer solution, but nevertheless the reaction proceeded over a period of two weeks in the cold (i.e., approximately 4° C.). A second attempt to form the amide in a two-phase system (i.e., an amine in water and an acid chloride in an organic solvent), with an aqueous ODN-buffer solution and NHS-PDA dissolved in $CH_2Cl_2$ was unsuccessful. Although an understanding of the mechanism is not necessary to practice the present invention, and the present invention is not limited to any particular mechanism, this failure was probably due to the very strong difference of polarity of both reactants, so that neither of them could cross the phase boundary to come in close enough proximity to react.

Figure 43:
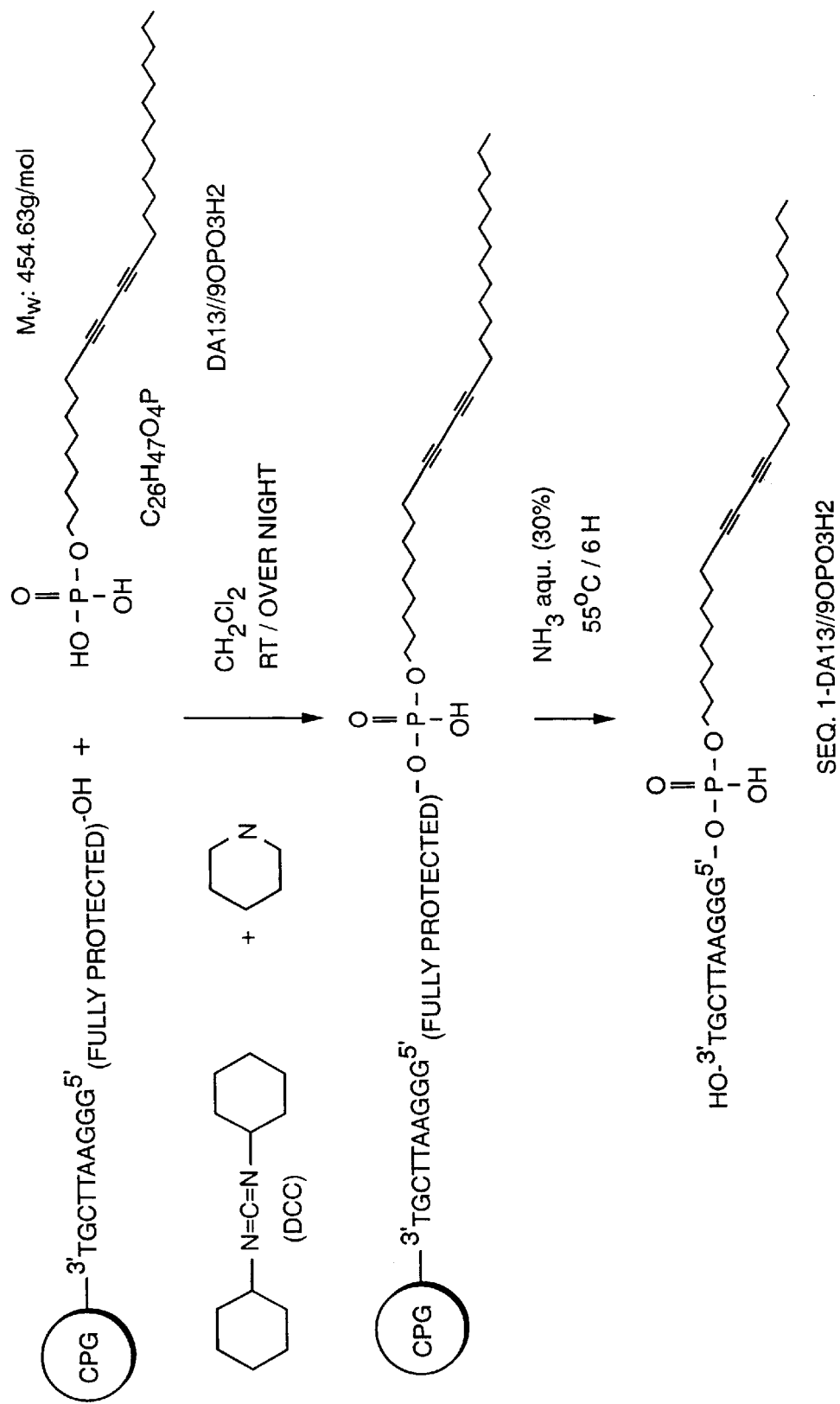

In addition, the primary OH-group of the 5'-terminus was conjugated to a diacetylene lipid with phosphate head group, using DCC as condensation agent and pyridine as base as shown in FIG. 43. The lipid was coupled to the detritylated Oligo 2 (i.e., the lipid-linked oligonucleotide designated as seq.1-DA13//9OPO3H2 in FIG. 43) carrying the nucleobase protecting groups and which was bound to the solid support. The ODN-lipid conjugate was cleaved from the solid support and deprotected with the standard $NH_3$ workup to yield Oligo 2 conjugate.

Large batches of liposomes were prepared during these experiments. Lipids were inially filtered, and the filtered lipid solution was placed in organic solvent. In preferred embodiments of the present invention, the total volume of organic solvent in a liposome solution with a volume of 30–80 ml was less than 5 ml, giving a high concentration of the lipid. The beaker was placed onto a handwarm heat plate and a gentle stream of $N_2$ was passed over the surface of the liquid. After complete evaporation a magnetic stirrbar and the appropriate ammount of $H_2O$ was added. The beaker was then mounted in the sonicator chamber on top of a magnetic stirrer with the sonicator tip resting 1–2 mm above the stirrbar. In preferred embodiments, the liquid was sonicated at 60% output power, with gentle stirring and heating (i.e., with a heat gun) until all solid was dispersed. After the appropriate sonication time (5–30 min) the hot solution was filtered through a 0.8 µm Metricel filter and refrigerated.

The effect of ODN on liposome polymerization was determined with 5% "Oligo 2" (i.e., the lipid-linked oligonucleotide designated as seq.1-DA13//9OPO3H2 in FIG. 43), added to a 1 mM solution of monomeric PDA liposomes, which were incubated for 15 min at room temperature, photopolymerized (1.6 J cm$^{-2}$) and then diluted to 0.1 mM lipid concentration. Based on comparisons between the utilized energy dose and the absorbance at 642 nm (Abs.$_{642}$=0.5 O.D., energy dose=1.6 J cm$^{-2}$) to the polymer absorbance of pure PDA liposomes (Abs.$_{639nm}$= 0.68 O.D., energy dose=0.8 J cm$^{-2}$), it was suggested that the presence of ODN reduced the efficiency of polymerization, due to the strong absorbance of ODN at 254 mn (i.e., the wavelength used for polymerization) although an understanding of the mechanism is not necessary to practice the present invention, and the present invention is not limited to any particular mechanism. Another effect might be the interaction of ODN with the liposome bilayer, which gets distorted, and thus less effectively polymerized. This interaction is also most likely responsible for the shift of the polymer maximum absorbance from 639 to 642 nm. After filtration (i.e., cc30 filtration; the filters used were centricon 30 filters with a molecular cutoff at ~30,000 g mol$^{-1}$ and filtration was achieved by centrifugation), the amount of ODN associated with the liposome phase was drastically reduced and the filtrate contained most of the ODN. After a second filtration step, most of the ODN was removed from the liposome phase. The loss of liposomes by 10–15% due to the filtration procedure, was comparable to that observed using pure liposomes.

ODN loss by cc30 filtration was quantified by subtracting the liposome background from the UV-Vis spectra, to obtain the pure ODN absorbance, reflecting a direct measure of ODN concentration in the liposome phase. By subtracting the volume corrected spectrum of the filtrate (i.e., pure Oligo 2) from the initial liposome-ODN spectrum, a pure liposome "blank" was created which in turn could be used to extract the clean ODN spectra from the retentate spectra. This procedure allowed quantitative values to be obtained for the ODN concentration in the liposome phase, which decreased following an exponential "decay" law, as is reasonable for a dilution series. After two cc30 filtrations, a total of 75% liposomes and 14% ODN were retained. The exact ODN concentration in the retained liposome phase depended on three major factors: i) the dilution of the remaining ODN in the retentate which was diluted following an exponentially declining function; ii) a fraction of the ODN unspecifically bound to the liposomes, with binding in equilibrium with the ODN concentration in the surrounding medium; and iii) the loss of ODN by absorption of liposomes at the filter surface by which ODN gets entrapped in the filter and which was correlated to polymer loss. The last factor becomes particularly important when the ODN is specifically bound to the liposome surface, as is the case with the ODN-lipid conjugates.

In some experiments, PDA liposomes (1 mM concentration) were mixed with 5% "Oligo 3" cccttaagca (SEQ ID NO:3) (the complement of Oligo 2). The liposomes precipitated upon irradiation, which was due to the high salt content in this ODN sample. To improve polymerization yields, the PDA liposomes were diluted to a concentration of 0.1 mM prior to polymerization. After incubating the diluted liposomes with 5% Oligo 2 for 14 h at room temperature and 6 h at 4° C., photopolymerization was achieved with an energy dose as low as 0.3 J cm$^{-2}$ (254 nm) in a comparable yield to pure PDA liposomes. The 10-fold dilution of the ODN-liposome mixture reduced the relative salt concentration and allowed a polymerization yield comparable to pure PDA liposomes and the Oligo 2 sample. This result was in contrast to the 1 mM liposome solution mixed with 5% Oligo 3, whereby the liposomes came out of solution upon irradiation due to high salt concentration. The major differences between Oligo 2 and Oligo 3 are the longer chain length (27-mer versus 10-mer) and the terminal primary amino group. This amino function can be protonated by the PDA acid head group to form a salt pair and the longer chain length should enhance unspecific adsorption at the liposome surface. Both effects lead to a higher ODN retention in the liposome phase. The polymer loss between the first and second filtration was 9%.

In other experiments, I-(3-dimethylaminopropyl)-3-ethylcarbodiimidebydrochloride (EDC) and NHS were added to the ODN/liposome mixture (i.e., PDA of 1 mM and 5% ODN), to produce a covalent attachment of Oligo 1 to the liposome surface. To this mixture 50 $\mu$l of an EDC stock (0.6 mg ml$^{-1}$ EDC.HCl in H$_2$O) and 1 $\mu$l of a NHS stock (0.6 mg ml$^{-1}$ in H$_2$O) were added and incubated for 11 h at room temperature. The monomeric liposome mixture was cc30 filtered/rediluted ($v_r$=1), polymerized (0.3 J cm$^{-2}$) and filtered/diluted again ($v_r$=1).

In yet other experiments, prepolymerized PDA liposomes (0.1 mM)/Oligo 1 (5%) were used. Unpolymerized PDA liposomes (0.1 mM) were cc30 filtered once, rediluted and polymerized (0.3 J cm$^{-2}$) and then incubated with 5% Oligo 1 for 11 h at room temperature. After ODN incubation, the liposomes were filtered twice more, with a polymer loss of 17% per filtration step. In yet other experiments, prepolymerized PDA liposomes (0.1 mM)/Oligo 1 (5%) were used with EDC and NHS-treated. EDC and NHS were added to the liposome surface, and the liposomes were polymerized before incubation with ODN. The PDA liposomes were filtered once in monomeric form, rediluted to 0.1 mM, polymerized (0.3 J cm$^{-2}$) and incubated with 5% Oligo 1, EDC (50 $\mu$l of 0.6 mg ml$^{-1}$ EDC.HCl in H$_2$O) and NHS (1 $\mu$l of 0.6 mg ml$^{-1}$ NHS in H$_2$O) for 11 h at room temperature. After incubation, the ODN-liposome mixture was filtered a second and a third time with a linear polymer loss of 15% and 23%, respectively. Although an understanding of the mechanism is not necessary in order to make and use the present invention, it is suggested that neither EDC/NHS treatment nor polymerization conditions (pre- or postpolymerization) significantly change the ODN retention behavior.

In addition, liposomes were investigated for their ability to covalently bind amino functionalized Oligo 1 on their surface. For this purpose the polymerized liposomes (0.3 J cm$^{-2}$, 0.1 mM) were incubated with 5% Oligo 1 for 11 h at RT, cc30 filtered, and rediluted to the original volume. The cc30 filtration was repeated two more times, and the polymer loss was measured at 640 nm, showing a slight exponential "flattening out." Although an understanding of the mechanism is not required to practice the present invention and the present invention is not limited to any particlar mechanistic explanation, this flattening of polymer loss was most likely due to a more complete coverage of the filter surface with adsorbed liposomes after each filtration step, leaving less free filter surface for further liposome adsorption. The pure ODN spectra were obtained after subtracting the liposome background, which allow calculation of the ODN loss upon filtration. This ODN loss followed essentially the same linear function, indicating that the use of 10% NHS-PDA in liposomes does not improve ODN retention.

Results showed that for the unmodified 10-mers and after three cc30 filtrations, about 70% of polymer (decreases to ~40% at high salt concentration) and 6% ODN were retained. The amino functionalized 27-mer with pure PDA liposomes were only twice cc30 filtered. From the linear relationship between polymer-/ODN-loss and number of filtrations a polymer retention of 50–60% and an ODN retention of 16–32% after three cc30 filtrations can be extrapolated. With the NHS-PDA/PDA (10:90) liposomes only 24% polymer, but 37% ODN, were retained. If the ODN was bound to the liposome surface, the ODN retention was also a function of polymer loss, as ODN is extracted from solution with filter-adsorbed liposomes. This fact complicated the determination of actual ODN concentration relative to liposome concentration, since the precise nature and extent of ODN-liposome interaction was not known. Generally, the relative ODN retention in terms of liposome concentration was higher than the absolute ODN retention (i.e., relative to the total volume of the liposome phase).

To obtain a more specific (i.e., covalent) interaction of ODN with the liposomes, two different ODN-lipid conjugates were synthesized. The monomeric liposomes (0.1 mM, 500 $\mu$l) were incubated with the ODN-lipid conjugates (5%, 8.5 h at room temperature, and 15 h at 4° C.), polymerized (0.3 J cm$^{-2}$) and then three times cc30 filtered/washed (300 $\mu$l H$_2$O each). Before and after this treatment the UV-Vis spectra were taken to quantify polymer- and ODN loss. To 100 $\mu$l of the unfiltered ODN-liposome mixture, an equivalent of unmodified complementary ODN was added to test colorimetric response upon hybridization. UV-Vis spectra of PDA liposomes mixed with Oligo 2 (5%) before and after three cc30 filtrations indicated that the filtrate contained only ODN. Addition of the complementary Oligo 3 at room temperature did not affect the polymer absorption spectrum.

Figure 27:
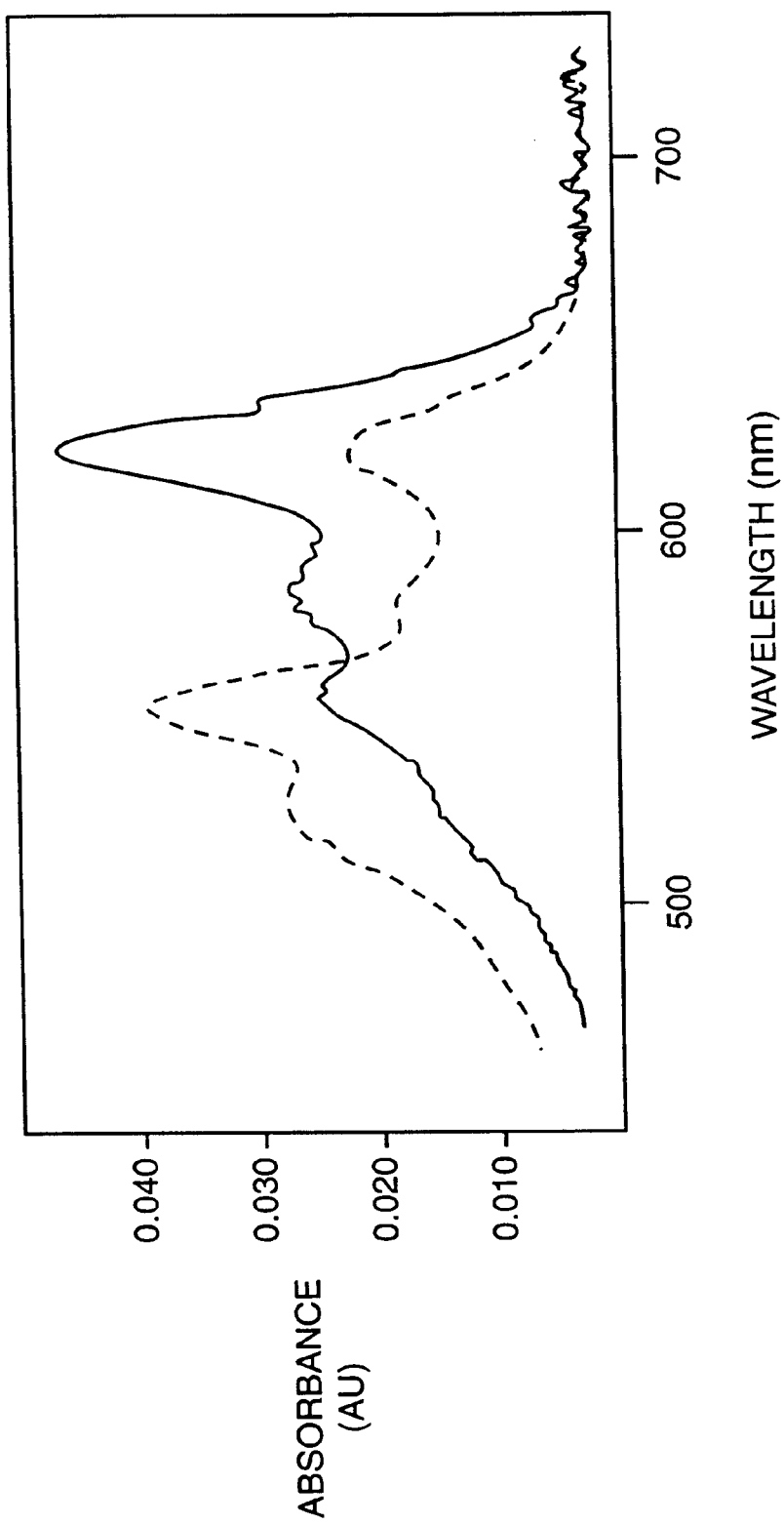
FIG. 27 shows the visible absorption spectrum for sialic-acid containing films before (solid line) and after (dashed line) exposure to influenza virus.
Figure 28:
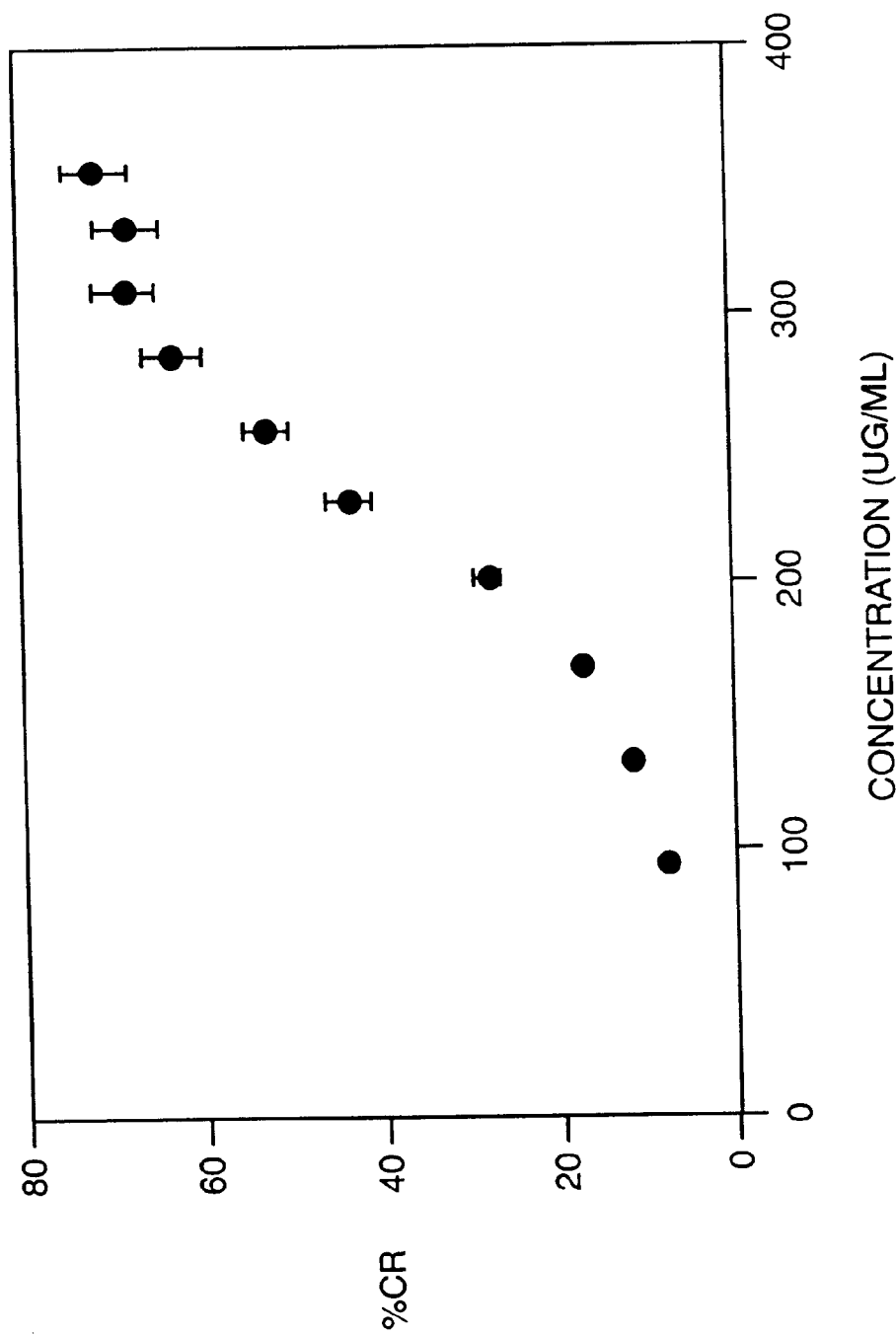
FIG. 28 shows the color transition of ganglioside $G_{M1}$-containing liposomes in response to varying concentrations of cholera toxin.
Figure 29:
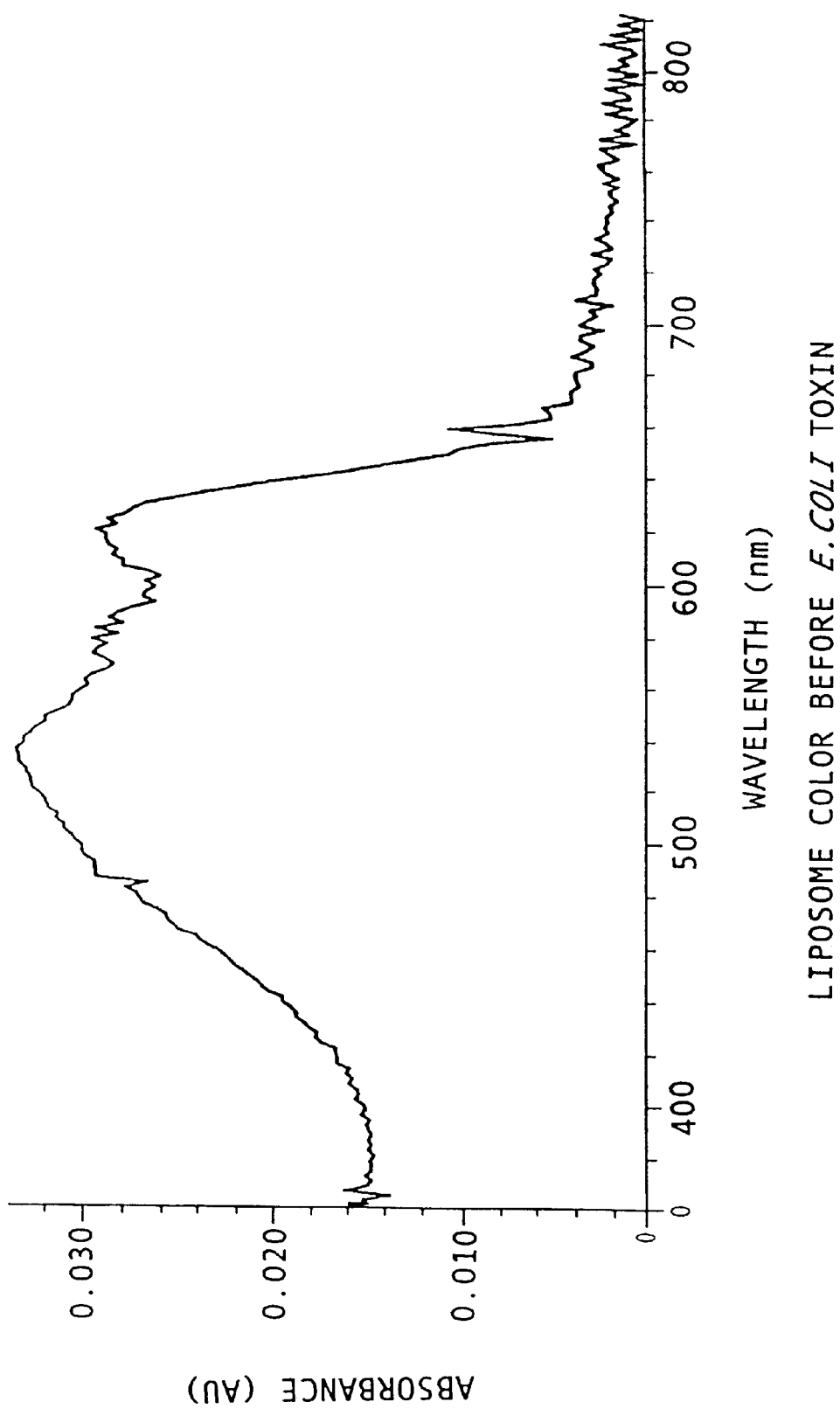
FIG. 29 shows the visible absorption spectrum of the polymeric liposomes containing 5% $G_{M1}$ ligand and 95% 5,7-DCDA.
Figure 30:
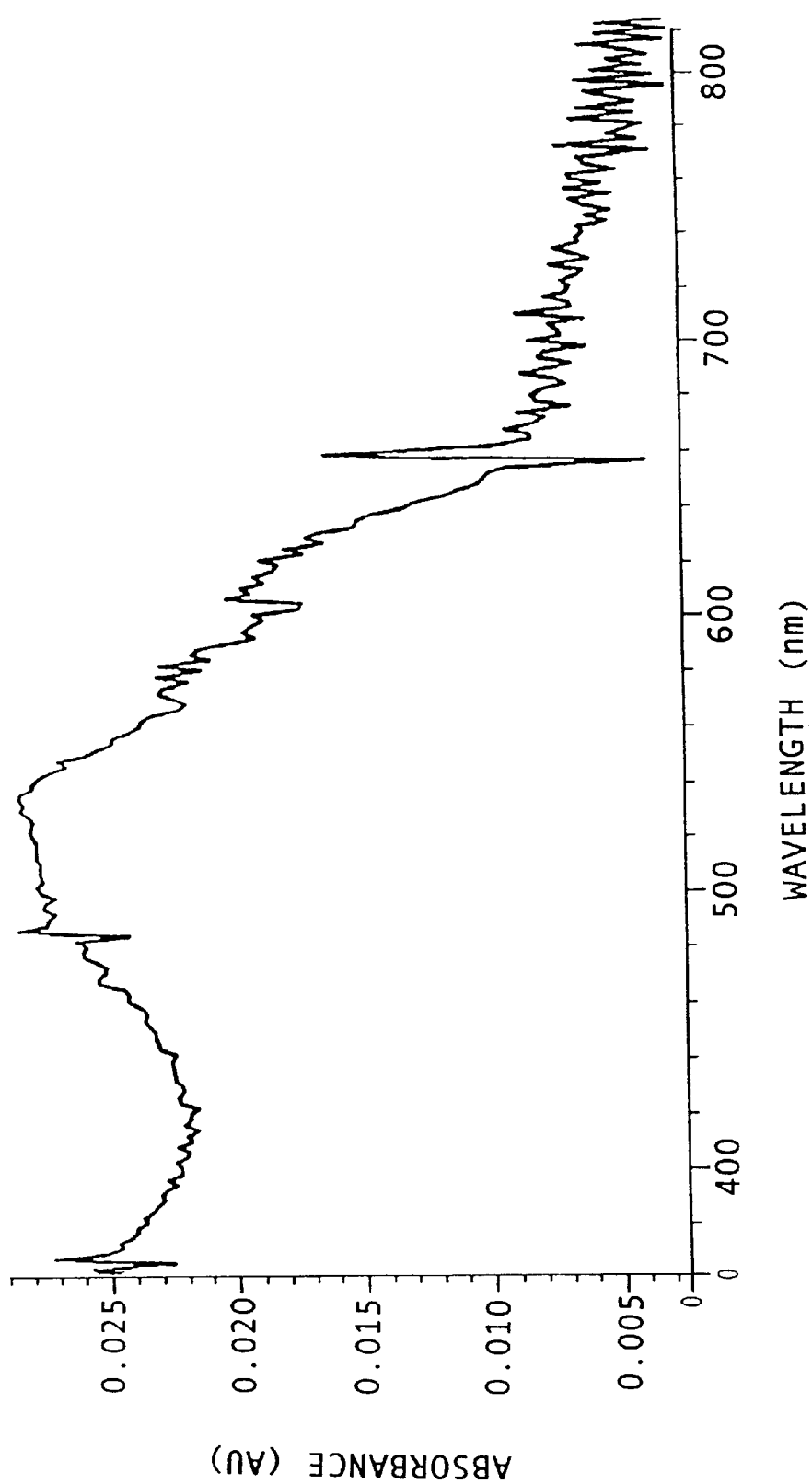
FIG. 30 shows the visible absorption spectrum of the material in FIG. 29 following exposure to E. coli toxin.

In additional experiments, 5% of the Oligo 1 conjugate was mixed with PDA liposomes, and shown to drastically reduce polymerization yield. Although an understanding the mechanism is not necessary to practice the present invention, and the present invention is not limited to a particular mechanism, this reduction in yield was probably due to an insertion of the ODN-lipid tail into the liposome bilayer, causing some disorder in the PDA packing. Addition of an oligonucleotide complementary Oligo 1 (i.e., Oligo 4) slightly increased the red polymer absorbance. About 79% polymer was retained after three filtrations. In one embodiment of the present invention, PDA liposomes (0.1 mM) were incubated with 5% Oligo 4 followed by polymerization (0.3 J cm$^{-2}$), and filtered to give a polymer retention of 39% and an ODN retention of 31% (FIG. 27).

Figure 44A:
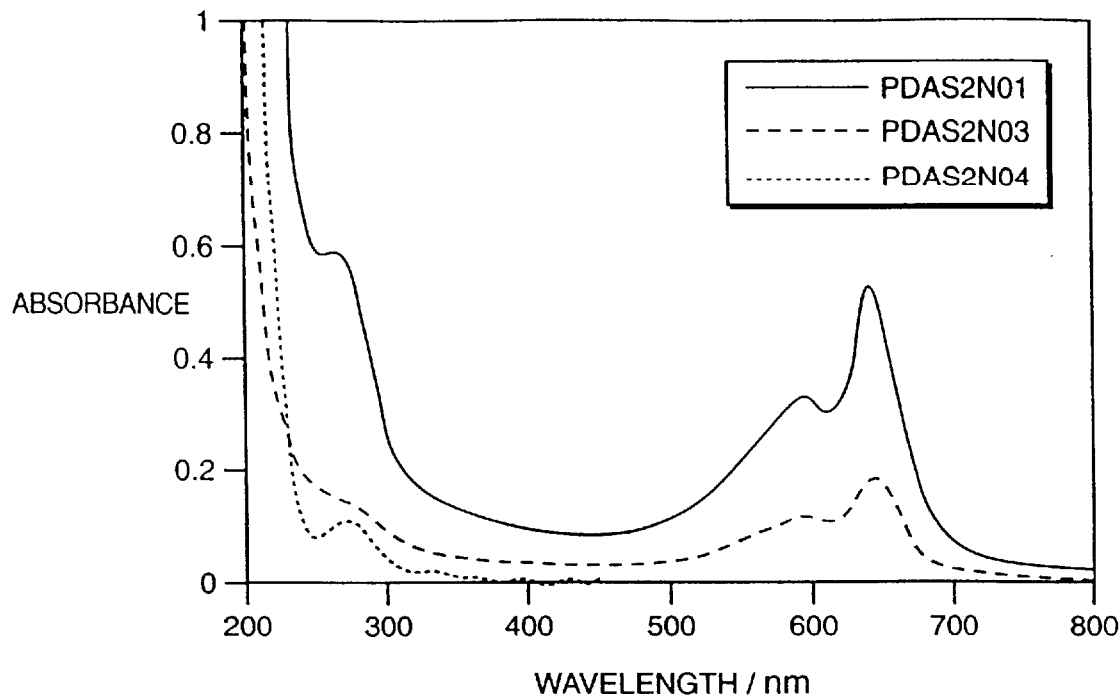
Figure 44B:
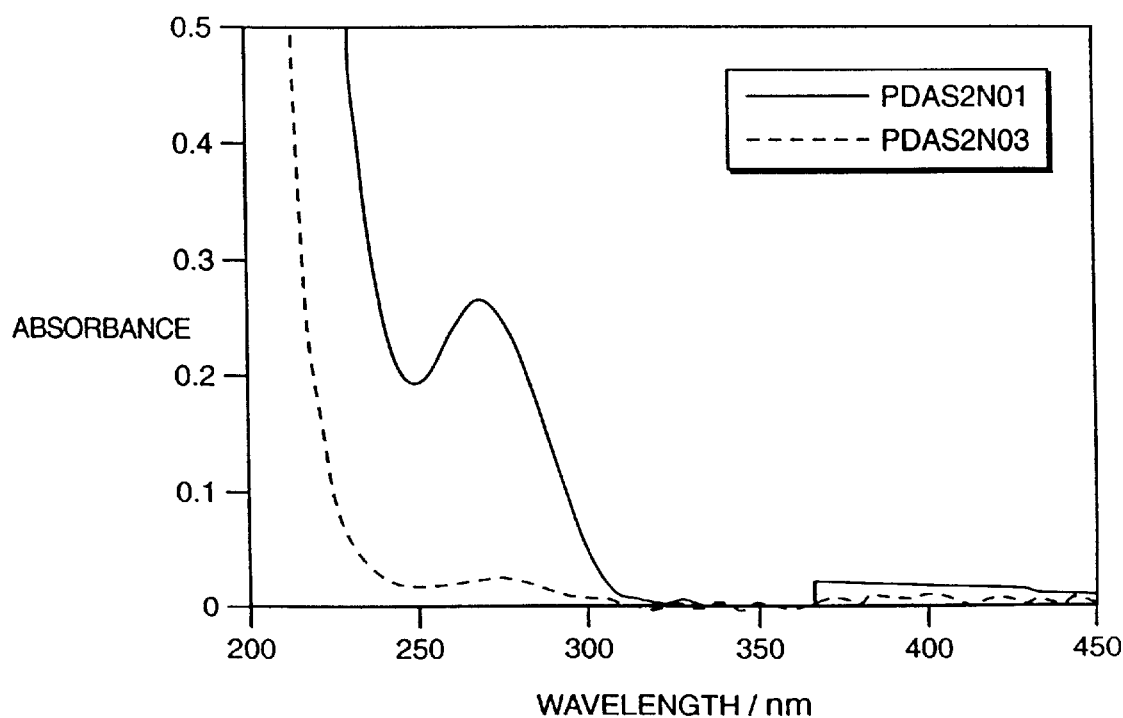

In other experiments, POS liposomes (0.1 mM) made from the monophosphate 10,12-hexacosadiyn-1-ol phosphate (hereinafter, "DA13 liposomes") were incubated with 5% of Oligo 2 lipid, which were then polymerized (0.3 J cm$^{-2}$), and three times cc30 filtered with a 51% polymer retention. Adding an equivalent of the complement Oligo 3 induced a faint increase in the red absorbance, and a subsequent decrease in blue absorbance. From the extracted ODN spectra in shown in FIG. 44, a high ODN retention of 28% was deduced. Although an understanding of the mechanism is not necessary to practice the present invention, and the present invention is not limited to any particular mechanism, mixing 5% Oligo 1 with POS liposomes (0.1 mM) reduced the polymerization yield (0.3 J cm$^{-2}$), probably due to intercalation of ODN-lipids into the POS liposomes. In this case the absorption maximum was even shifted to longer wavelengths, giving the liposomes a greenish tint. Addition of the complement Oligo 4 did not affect the polymer absorbance. After three cc30 filtrations, 76% polymer and 56% ODN were retained.

All samples mixed with their ODN complements were incubated for about 30 min. at 40° C. to induce specific hybridization and color transition, but only the POS liposomes with Oligo 2/Oligo 3 visibly changed color to red.

Synthesis and Hybridization of DNA-PDA Conjugates

Two complementary sequences SEQ ID NO:5 (Oligo 2; SEQ ID NO:5) (5'GGG AAT TCG T3') and SEQ ID NO:3 (Oligo 3; SEQ ID NO:3) (5'ACG AAT TCC C3') were synthesized on an Experdite 8909 nucleic acid synthesis system (PerSeptive Biosystems) by the standard phosphoramidite route.

The general phosphoramidite method is schematically depicted in FIG. 46. In a first step A), the dimethoxytrityl (DMT) group was cleaved at the 5'-end of a solid support bound nucleotide. The solid support was usually controlled pore glass (CPG) which was modified with long chain alkylamino groups to which the nucleotide was bound at the 3'-end of the deoxyribose via a succinyl spacer. The free 5'-OH group was then activated in step B) by tetrazole and coupled with a phosphoramidite, to form the one nucleotide elongated chain. In step C), the unreacted 5'-OH ends was esterified with acetic anhydride to reduce the occurence of failure sequences. In the next step D), the phosphite triester bond was oxidized to the corresponding phosphotriester by iodine in pyridine/$H_2O$. The cycle was then repeated ad libidum with the needed phosphoramidites, until the final sequence is established. By treating the material with aqueous $NH_3$ (30%), cleavage from solid support, and deprotection of the nucleotides, free bioactive DNA was obtained. Removal of protecting groups, salt and small byproducts can usually be achieved by spin column chromatography through Sephadex G-25 or G-50 columns.

Cleavage from CPG and deprotection of DNA may be achieved by a variety of methods. In one method, the column is cut open to retrieve CPG beads, which are transferred into a small screw-capped, teflon-lined container. The CPG beads are treated for 6–8 h at 55° C. with 1 ml conc. $NH_4OH$ (30%), and ammonia is then decanted from the beads. Alternatively, two syringes with 1 ml conc. $NH_4OH$ (30%) are connected to the ends of the column, the ammonium hydroxide solution pushed forth and back for 1.5 h, transferred to a glass vial and heated for 6 h at 55° C. The DNA containing ammonium hydroxide solution is evaporated to dryness by centrifuging (i.e., "speed vac"), and the solid obtained is redissolved in 200 μl $H_2O$.

Figure 47:
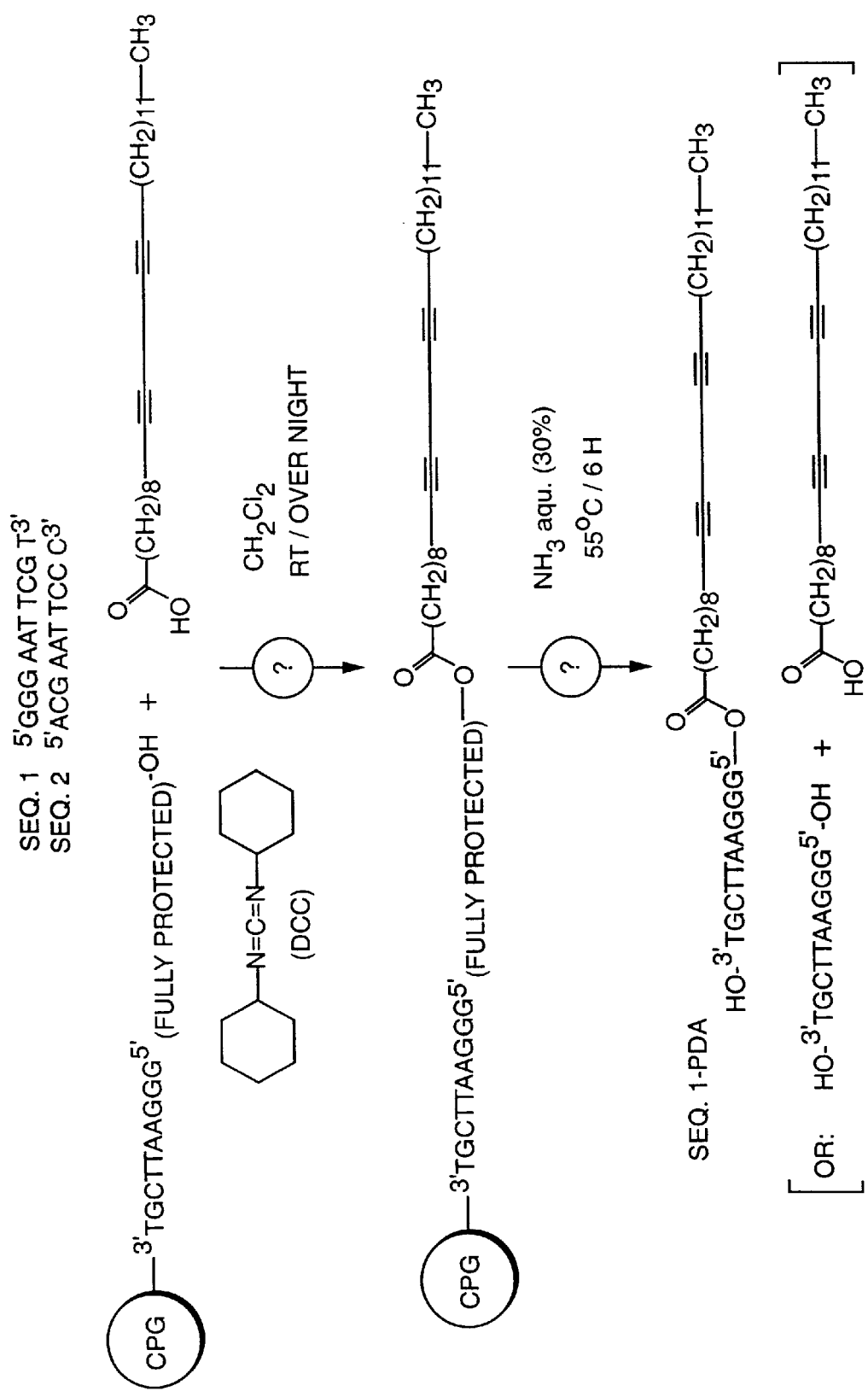
Figure 48:
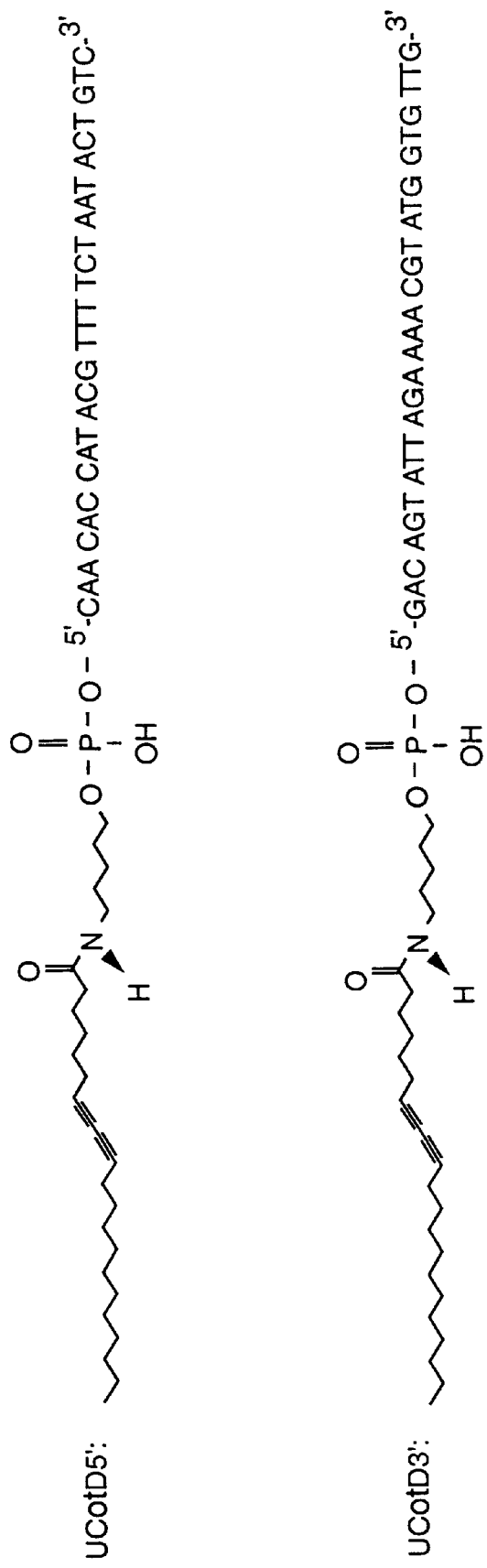

The free 5'-end of the fully protected and polymer support bound SEQ1 was treated with PDA and DCC at room temperature in $CH_2Cl_2$ to obtain the DNA-PDA conjugate. Following this method, the side products (i.e., dicylclohexyl urea) and excessive reagents can be washed from the column prior to DNA cleavage to avoid unnecessary purification steps. The reaction scheme for conjugation of SEQ1 with PDA is illustrated in FIG. 47. Since DNA cleavage from polymer support and removal of protecting groups (benzoyl and iso-butyloyl groups) was achieved by treatment with concentrated ammonia solution (30%) at 55° C. for 6–8 hours the danger of cleaving the DNA-PDA ester bond had to be considered.

Two basic purification procedures, ethanol precipitation and Sephadex G-25 spin column chromatography, were tested to remove any cleaved protecting groups and salts from the 10-mers. With SEQ2, the ethanol precipitation did not work most likely due to the short length of the 10-mer which makes it soluble in ethanol (70%)/$NH_4AcO$. The success of the Sephadex G-25 chromatography could not be directly checked, but it could be shown by UV-Vis spectroscopy that the DNA did come through the column. Gel electrophoresis on a 20% acrylamide gel was performed to elucidate the success of the coupling reaction between SEQ1 and PDA. The gels were stained with ethidium bromide or silver nitrate, and showed that the 10-mers are very insensitive to ethidium bromide. Electrophoresis shows that SEQ1 samples ran slightly faster than SEQ2, and that SEQ1-PDA and SEQ2 formed hybrides that stained well with ethidium bromide.

To check whether free PDA was present in the SEQ1-PDA sample, TLC was employed and stained with silver nitrate as known in the art. This method resulted in strong staining of PDA on silicagel upon heating. This experiment shows that no free PDA could be detected in the SEQ1-PDA samples, although the DNA was not run on silica gel to reveal differences in polarity between SEQ1-PDA and SEQ2. UV-Vis spectra taken from the DNA samples showed the typical nucleo base peak at ~260 nm and a strong absorption at ~200 nm with intensity varying in different samples (most likely due to varying salt concentration).

To check whether diacetylene lipids (i.e., phosphoramidites) could be used in automated DNA synthesis, the stability of PDA against iodine in acetonitrile was tested by dissolving PDA and $I_2$ in acetonitrile at room temperature, and conducting TLC after 5 min. The $I_2$ was used as oxidizing agent in automated DNA synthesis to oxidize the trivalent phosphonium ester to the pentavalent phosphoric acid ester after the nucleobase coupling step (FIG. 33). The TLC showed that PDA readily reacted with $I_2$ (addition) to form a more polar product that does not polymerize upon UV irradiation, suggesting that diacetylenes might not be directly used in the DNA synthesizer.

In one embodiment, Oligo 2 was conjugated with DA13 lipid. A 2 mM DA13 solution (2.5 mL, 5 μmol) in $CH_2Cl_2$/EtOH (95:5) was rotavaped to dryness and redissolved in 1 ml $CH_2Cl_2$ and 1 μl pyridine. To this solution was added 5.2 mg (25 μmol) of DCC, and the mixture was injected into a membrane filter (MemSyn Nucleic Acid Synthesis Device, PerSeptive Biosystems) carrying the detritylated, fully protected Oligo 2. The reaction was left overnight while an insoluble white precipitate formed (most likely pyrophosphates). The liquid was removed and the membrane washed several times with $CH_2Cl_2$, MeOH and $H_2O$. ODN was cleaved from solid support/deprotected by the standard workup (aqueous $NH_3$ 30%, 55° C. for 6 hours) and finally resuspended in 200 μl $H_2O$ to yield raw Oligo 2 conjugate in a concentration of 203.1 pmol $\mu l^{-1}$ (642.6 μg $ml^{-1}$).

In another embodiment of the present invention, Oligo 1 was conjugate with NHS-PDA. A solution of NHS-PDA (6 μl, 0.24 mg, 508 nmol) NHS-PDA solution in $CH_2Cl_2$ (40 mg $ml^{-1}$) was dried and redissolved in 90 μl DMSO. Then, 70 μl Oligo 1 (0.26 μmol $ml^{-1}$) and 10 μl $Na_2CO_3$/$NaHCO_3$ buffer pH 9 (1 M) were added to the solution, causing the NHS-PDA to precipitate. The reaction mixture was kept at room temperature overnight and then stored for two weeks at approximately 4° C. After this period, the mixture was diluted with 1000 μl of $H_2O$ and extracted five times with 500 μl $CH_2Cl_2$ (each time). The aqueous phase was speed-vaced and redissolved in 100 μl $H_2O$ yielding the raw W001 (Oligo 1 conjugate) fraction (150.5 pmol $\mu l^{-1}$, 1304 μg $ml^{-1}$ ODN+NHS). The buffer solution was prepared by mixing aqueous solutions of $Na_2CO_3$ (1 M) and $NaHCO_3$ (1M) in a ratio of 1:8.

Figure 49:
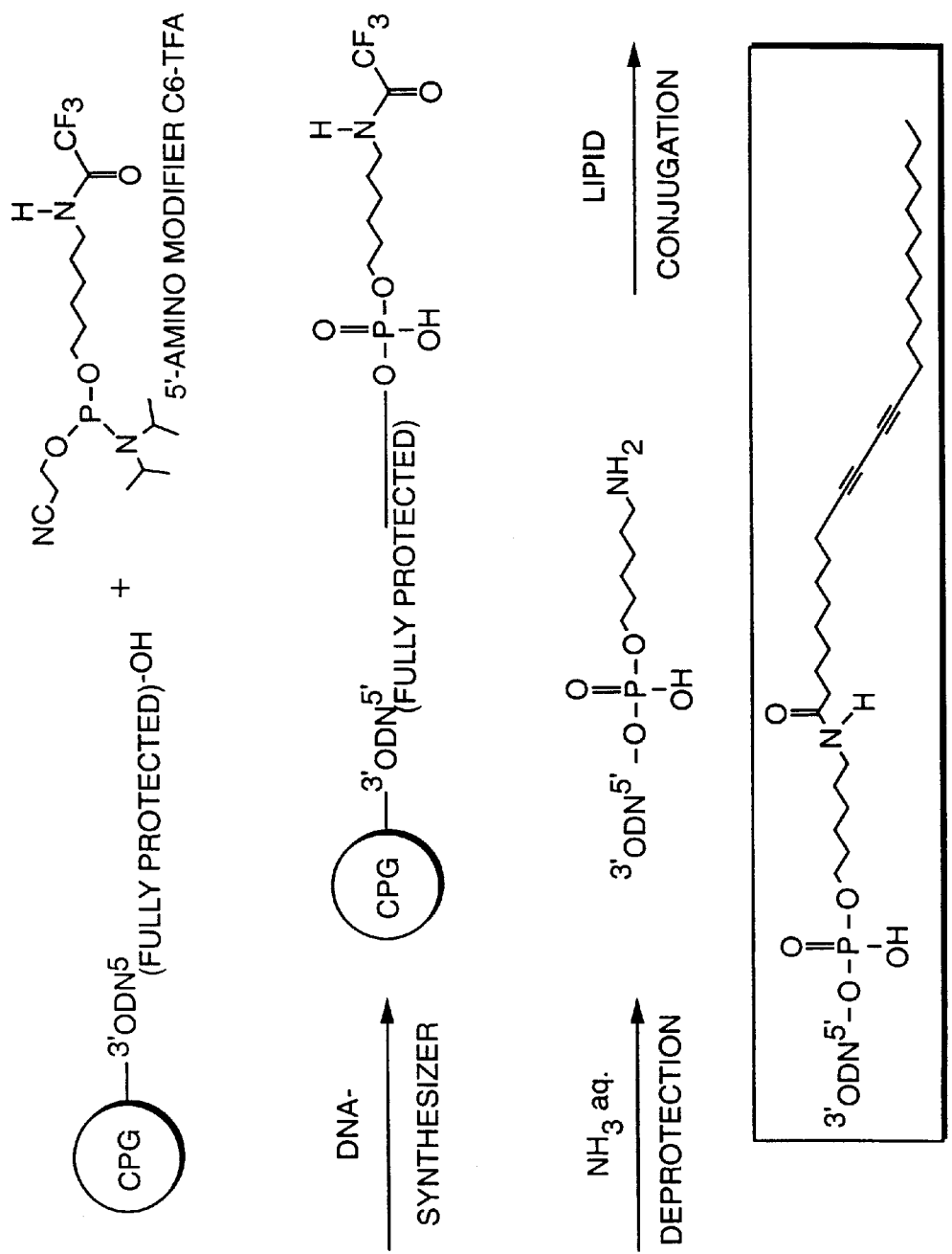

In other experiments, the 27-mer from the *Bacillus globigii* genome UCotD5' and its complementary sequence UCotD3' (shown with a PDA-lipid conjug via an amino linker) were used as shown in FIG. 34. The amino modification on the DNA synthesizer and subsequent lipid conjugation is illustrated in FIG. 49. Modifications in reaction parameters (i.e., prehydration of ODN, DMSO/acetone as solvent for NHS-PDA) increased the yield of ODN-lipid.

Figure 50:
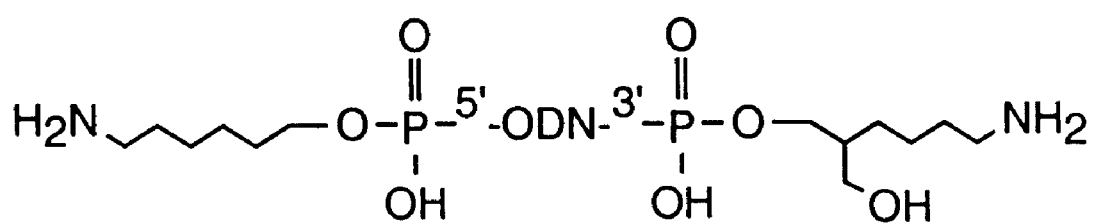

From each sequence an unmodified batch (UNahHsn), a 5' amino modified batch (using 5'-Amino Modifier C6-TFA as in FIG. 49, UNahHsnam), and a bis-amino modified batch (primary amino groups at both ends, UNahHsnam2×) were synthesized. For the bis-amino modified ODN, an amino functionalized solid support was used in the synthesis, resulting in the bifunctional ODN shown in FIG. 50.

In other experiments, NHS-PDA was conjugated with an amino-modified ODN. An amino modified ODN (40–50 nmol) in 200 $\mu$l $H_2O$ was speed-vacuumed to complete dryness, then rehydrated for ~30 min. with 5 $\mu$l $H_2O$, dissolved in 200 $\mu$l DMSO (~10 min. mixing time). To this solution was added 20 $\mu$l of 1M $Na_2$/$NaHCO_3$ buffer, pH 9, and 40 $\mu$l of 0.7 mg NHS-PDA in 40 ml DMSO/acetone (1:1 v/v). After ~24 hours, 400 $\mu$l $H_2O$ were added and extracted five times with 400 $\mu$l $CH_2Cl_2$ each. The aqueous phase was speed-vacuumed and the solid resuspended in 200 $\mu$l $H_2O$. Precipitation with n-butanol was accomplished by adding n-butanol (300 $\mu$l) to ~30 $\mu$l ODN solution. The solution was shaken well and centrifuged at 14000 rpm for 10 minutes. The organic phase was carefully decanted from the pellet, 300 $\mu$l ethanol (100%) was added and spun at 14000 rpm for 5 min. After the ethanol was decanted, the pellet was dryed in the speed-vacuum for ~1 minute.

In addition, [N-(6-aminohexyl)-p-azidobenzoic amido] was synthesized. N-succinimidyl 4-azidobenzoate (250 mg, 0.95 mmol, ABA-NHS) was suspended in 2 ml $CH_2Cl_2$ (water bath cooling), and a solution of 550 mg (4.8 mmol) hexamethylenediamine in 2 ml $CH_2Cl_2$ was added. A white precipitate formed immediately and 4 ml $CH_2Cl_2$ was added and stirred for 30 min. Then ~5 ml $H_2O$ was added, upon which a stable emulsion formed. The organic phase was extracted several times with water, separated from the white solid at the interface and dried. This compound decomposes in solid form at ~18° C. over the period of several weeks, but it is stable in ethanolic solution (1 mM).

To purify the DNA from protecting groups and reaction side products, ethanol precipitation was tested. SEQ2 was redissolved in 400 $\mu$l $H_2O$, followed by addition of 140 $\mu$l aqueous $NH_4AcO$ (7.5 M, pH 5.2) and 1080 $\mu$l EtOH. The solution was stored overnight at ~20° C. and centrifuged at 5° C. for 30 min/14000 r $min^{-1}$ the following day. However, no precipitate was obtained. Further addition of 140 $\mu$l $NH_4AcO$ also did not result in a precipitate.

The solution was concentrated again to 400 $\mu$l (via speed vac), and the DNA concentration was found to be 430 pmol $\mu l^{-1}$/1314 $\mu$g $ml^{-1}$. To remove salts and other side products (e.g., excess PDA), the SEQ2 solution was filtered through 1 ml Sephadex G-25 by spinning for 1 min at 1000 r $min^{-1}$ to obtain the fraction SEQ2 spin c.s.p.B, with a concentration of 221 pmol $\mu l^{-1}$/673 $\mu$g $ml^{-1}$. Running another 200 $\mu$l TE through the column gave a second fraction SEQ2 spin c.s.p.B(TE) with 72 pmol $\mu l^{-1}$/219 $\mu$g $ml^{-1}$. The Sephadex G-25 column itself was prepared just prior to use by clogging the small opening of a 1 ml syringe with hydrophobized glass wool, and filling the column with a suspension of Sephadex G-25 in TE (5 ml per 1 g G-25; TE: 10 mM Tris/HCl+1 mM EDTA, pH 8). The syringe was repeatedly filled and spun for 30 s/1000 r $min^{-1}$ to pack it with a total of 1 ml G-25. Then the column was spun dry for 2-min/1000 r $min^{-1}$.

In one embodiment of the present invention, PDA (7.4 mg, 20 $\mu$mole) was dissolved in 1 ml $CH_2Cl_2$, filtered through a 0.22 $\mu$m Teflon membrane to remove polymerized material. To the filtered PDA was added dicyclohexylcarbodiimide (DCC, 4.1 mg, 20 $\mu$mole). The 0.2 $\mu$m column with detrylated SEQ1 was washed with 2 ml $CH_2Cl_2$, and then the PDA reaction mixture was injected into the column containing SEQ1 by connecting two syringes at both ends of the column, and pushing the mixture several times back and forth. The reaction was allowed to proceed overnight at room temperature. The reaction mixture was removed the following day, and the column was flushed with 2 mL portions of $CH_2Cl_2$ twice, followed by flushing with 2 mL portions of EtOH. To cleave the DNA from the column, 1 ml of conc. $NH_3$ solution (30%) was injected and pushed forth and back several times over the period of 1.5 h. Due to a leak, 0.5 ml of the $NH_3$ solution was lost after 15 min reaction time. After 1.5 h the remaining solution was transferred to a vial with a teflon-lined screw cap, which was sealed and heated for 6 hours at 55° C. The solution was then transferred to an Eppendorf tube and concentrated to dryness in a speed-vac centrifuge. The solid was dissolved in 200 $\mu$l $H_2O$ and divided into the following volumes: i) 50 $\mu$l SEQ1-PDA raw (433 pmol $\mu l^{-1}$/1368 $\mu$g $ml^{-1}$); and ii) 150 $\mu$l SEQ1-PDA raw, with further addition of 50 $\mu$l TE, and desalted through Sephadex G-25 spin column (SEQ1-PDA s.c., 213 pmol $\mu l^{-1}$/672 $\mu$g $ml^{-1}$). Through the spin column another 200 $\mu$l TE was run to wash down remaining DNA (SEQ1-PDA s.c.(TE), 52 pmol $\mu l^{-1}$/163 $\mu$g $ml^{-1}$).

As a general procedure for hybridization, the two complementary DNA strands (i.e., SEQ-PDA and SEQ2) are mixed at 1 $\mu$g (each) in 100 $\mu$l $H_2O$, heated for ~3 min in boiling water and slowly cooled. For example, in one experiment 1 $\mu$l SEQ1-PDA raw (1368 $\mu$g $ml^{-1}$) and 2 $\mu$l SEQ2 spin c.s.p.B (673 $\mu$g $ml^{-1}$) were mixed together in 134 $\mu$l $H_2O$, to give a final concentration of 10 ng $\mu l^{-1}$ (HybA). In another experiment, 1.5 $\mu$l SEQ1-PDA s.c. (672 $\mu$g ml) and 1.5 $\mu$l SEQ2 spin c.s.p.B (673 $\mu$g $ml^{-1}$) were mixted together in 97 $\mu$l $H_2O$, to give a final concentration of 10 ng $\mu l^{-1}$ (HybB). A water bath was heated to boil in a microwave oven, then samples were immersed for 3 min, taken out, and allowed to cool on bench for 20 min at room temperature, and then stored in freezer, at −30° C. Following DNA hydridization, the PDA-DNA conjugate were run on gels for further characterization.

EXAMPLE 12

Colorimetric Detection of HIV-1 Using Nucleic Acid Ligand Hybridization

The following example illustrates the use of materials and methods of the present invention to detect target nucleic acid molecules in a sample suspected of containing nucleic acid associated with HIV-1. In particular, this example illustrates the use of the nucleic acid-linked biopolymeric materials of the present invention to detect the presence of HIV-1 in clinical samples using the methods of the present invention. The procedure described below is a modification of the reverse dot blot procedure described in U.S. Pat. No. 5,599, 662 to Respess (herein incorporated by reference), used to detect HIV-1.

The nucleic acid linked biopolymeric materials of this Example are prepared according to Example 11, except a different nucleic acid ligand sequence (probe) is used. As in Respess, two different 35-mer probes are constructed (termed RAR 1034 and RAR 1037 by Respess). These sequences are synthesized by the standard phosphramidite route as described in Example 11. These 35-mer sequences are amino functionalized and reacted with NHS-PDA as described in Example 11, in order to covalently link these sequences to the biopolymeric material of the present invention (i.e., these sequence serve as the nucleic acid ligands of the present invention). This biopolymeric material is used to detect HIV-1 as described below.

Clinical samples are obtained from subjects suspected of being infected with HIV-1 by taking a blood sample, and isolating the peripheral blood monocytes by the standard Ficoll-Hypaque density gradient method described in Boyum (Boyum, Scan. J. Clin. Lab. Invest., 21 (Suppl.97) :77 [1968]; herein incorporated by reference). Another method involves isolating the white blood cells from the blood sample by direct red blood cell lysis and DNA extraction as described in Casareale et al., (Casareale et al., PCR Meth. Appln., 2;149–153[1992]; herein incorporated by reference).

The next step involves amplifying the target HIV-1 DNA which may be present in the clinical sample. This is done using two 33-mer primers (termed RAR 1032 and RAR 1033 by Respess) using standard PCR methodology. Unlike Respess, however, the present Example does not require the primers to be biotinylated in order to detect the amplified DNA.

Detection of amplified target DNA is then carried out using the nucleic acid-linked biopolymeric material described above. Clinical samples are added to eight-microwell plates containing the biopolymeric material immobilized to the surface of each well for about 30 minutes at 40 degrees Celsius (allowing hybridization to occur). The presence of HIV-1 DNA is indicated by visible color change of the biopolymeric material. No wash step is necessary, as the presence of HIV-1 DNA alone is enough to cause a detectable color change in the biopolymeric material of the present invention. This is contrasted to Respess, which does require a wash step before developing the microwell with the addition of avidin-HRP conjugate (another step not required by the present invention).

As is clear from the above Example, the calorimetric materials and methods of the invention have many advantages for detecting the presence of DNA in a sample. In particular, this method allows the detection of amplified target DNA without the need to label the target DNA. This method also does not require a wash step, nor the addition of a developing solution (e.g., avidin-HRP) in order to detect the presence of target DNA.

EXAMPLE 13

Detection of Chorionic Gonadotropin Hormone

This Example demonstrates the usefulness of the methods and materials of the present invention as applied to a home pregnancy test. In particular, this Example demonstrates the use of the nucleic acid-linked biopolymeric material of the present invention for the detection of human chorionic gonadotropin in urine for early pregnancy diagnosis.

Human chorionic gonadotropin (hCG) is a glycoprotein hormone synthesized by the placenta and released in blood and urine soon after the implantation of a fertilized ovum in the chorionic tissue. As such, the detection of hCG is widely used as a pregnancy indicator in home pregnancy tests (See, U.S. Pat. No. 5,145,789, herein incorporated by reference).

The nucleic acid linked biopolymeric materials of this Example are prepared according to Example 11, except a different nucleic acid ligand is used. The nucleic acid ligand in this Example must have affinity for hCG in order to be useful in a home pregnancy test. One method for identifying such nucleic acid ligands is the SELEX procedure described above. The basic SELEX procedure is described in U.S. Pat. Nos. 5,475,096; 5,270,163; and 5,475,096; and in PCT publications WO 97/38134, WO 98/33941, and WO 99/07724, all of which are herein incorporated by reference. The SELEX procedure allows identification of a nucleic acid molecules with unique sequences, each of which has the property of binding specifically to a desired target analyte or molecule. This procedure was used by Drolet et al (U.S. Pat. No. 5,874,218; herein incorporated by reference) in order to find a nucleic acid ligand that specifically bound to hCG. This nucleic acid sequence is called H-42 RNA by Drolet et al., and can be synthesized by the standard phosphramidite route as described in Example 11, or isolated by employing the SELEX procedure. This hCG specific nucleic acid ligand is amino-functionalized and reacted with NHS-PDA as described in Example 11 in order to covalently link these sequences to the biopolymeric material of the present invention (i.e., these sequence serve as the nucleic acid ligands of the present invention). This biopolymeric material is used to detect hCG for home pregnancy tests as described below.

The biopolymeric material is then immobilized to a solid support, such as nylon filter paper, in order to construct a home pregnancy testing device. An example of such device is described in U.S. Pat. No. 5,145,789 to Corti et al., except the nylon filter paper is produced as described above. Although the device of the present invention is employed in basically the same manner as Corti et al., the biopolymeric material of the present invention changes from one distinct color to another in the presence of urine or blood containing hCG, a feature of the present invention that provides various advantages (e.g., ease of reading), that are lacking in the Corti et al. device. The presence of hCG is detected by hCG binding to the nucleic acid ligands linked to the biopolymeric material of the present invention which causes a color change in biopolymeric material. Thus, the present invention provides an easy to use device that is easy to read and analyze, suitable for point-of-care, and/or home testing.

We claim:

1. A composition comprising one or more biopolymeric materials comprising a plurality of polymerized self-assembling lipid monomers and one or more nucleic acid ligands, wherein binding of an analyte to said nucleic acid ligand causes a conformational change in said polymerized self-assembling lipid monomers, resulting in a color change in said biopolymeric materials.

2. The composition of claim 1, wherein said one or more nucleic acid ligands are capable of binding to said analyte.

3. The composition of claim 1, wherein said one or more nucleic acid ligands are single-stranded nucleic acid sequence.

4. The composition of claim 1, wherein said one or more nucleic acid ligands are linked to said polymerized self-assembling lipid monomers through one or more covalent bonds.

5. The composition of claim 4, wherein said one or more covalent bonds are selected from the group consisting of amine bonds, thiol bonds, and aldehyde bonds.

6. The composition of claim 2, wherein said analyte is selected from the group consisting of nucleic acid molecules, enzymes, pathogens, drugs, receptor ligands, antigens, ions, proteins, hormones, blood components, antibodies, and lectins.

7. The composition of claim 6, wherein said nucleic acid moleules are selected from the group consisting of ribosomal RNA, transfer RNA, messenger RNA, intron RNA, double-stranded RNA, single-stranded RNA, single-stranded DNA, double-stranded DNA, nucleic acid sequences characteristi of human pathogens, nucleic acid sequences characteristic of non-human pathogens, and nucleic acid sequences characteristic of genetic abnormalities.

8. The composition of claim 6, wherein said enzymes are selected from the group consisting of polymerases, nucleases, ligases, telomerases and transcription factors.

9. The composition of claim 6, wherein said pathogens are selected from the group consisting of viruses, bacteria, parasites, and fungi.

10. The composition of claim 1, further comprising one or more dopant materials.

11. The composition of claim 10, wherein said dopant material is selected from the group consisting of surfactants, polysorbate, octoxynol, sodium dodecyl sulfate, polyethylene glycol, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cholesterol, steroids, cerebroside, lysophosphatidylcholine, D-erythroshingosine, sphingomyelin, dodecyl phosphocholine, and N-biotinyl phosphatidylethanolamine.

12. The composition of claim 11, wherein said diacetylene derivatives are selected from the group consisting of sialic acid-derived diacetylene, lactose-derived diacetylene, and amino acid-derived diacetylene.

13. The composition of claim 1, further comprising one or more non-nucleic acid ligands.

14. The composition of claim 13, wherein said one or more non-nucleic acid ligands are selected from the group consisting of carbohydrates, proteins, drugs, chromophores, antigens, chelating compounds, molecular recognition complexes, ionic groups, polymerizable groups, linker groups, electron donors, electron acceptor groups, hydrophobic groups, hydrophilic groups, receptor binding groups, trisaccharides, tetrasaccharides, ganglioside $G_{M1}$, ganglioside $G_{T1b}$, sialic acid, and combinations thereof.

15. The composition of claim 1, wherein said one or more biopolymeric materials comprise biopolymeric films.

16. The composition of claim 1, wherein said one or more biopolymeric materials comprise biopolymeric liposomes.

17. The composition of claim 1, wherein said one or more biopolymeric materials are selected from the group consisting of tubules, braided assemblies, lamellar assemblies, helical assemblies, fiber-like assemblies, solvated rods, and solvated coils.

18. The composition of claim 1, wherein said self assembling monomers comprise diacetylene monomers.

19. The composition of claim 18, wherein said diacetylene monomers are selected from the group consisting of 5,7-docosadiynoic acid, 5,7-pentacosadiynoic acid, 10,12-pentacosadiynoic acid, and combinations thereof.

20. The composition of claim 1, wherein said self-assembling monomers contain head groups selected from the group consisting of carboxylic acid, hydroxyl groups, amine groups, amino acid derivatives, and hydrophobic groups.

21. The composition of claim 1, further comprising a support, and wherein said one or more biopolymeric materials are immobilized to said support.

22. The composition of claim 21, wherein said support is selected from the group consisting of polystyrene, polyethylene, teflon, mica, sephadex, sepharose, polyacrynitriles, filters, glass, gold, silicon chips, and silica.

23. A device comprising said one or more of the biopolymeric materials of claim 1, wherein said one or more biopolymeric materials are immobilized to said device.

* * * * *